United States Patent
Goldenberg et al.

(10) Patent No.: US 7,612,180 B2
(45) Date of Patent: Nov. 3, 2009

(54) HUMANIZED L243 ANTIBODIES

(75) Inventors: David M. Goldenberg, Mendham, NJ (US); Hans J. Hansen, Picayune, MS (US); Zhengxing Qu, Warren, NJ (US); Chein-Hsing Chang, Downington, PA (US)

(73) Assignee: Immunomedics, Inc., Morris Plains, NJ (US)

( * ) Notice: Subject to any disclaimer, the term of this patent is extended or adjusted under 35 U.S.C. 154(b) by 423 days.

(21) Appl. No.: 11/368,296

(22) Filed: Mar. 3, 2006

(65) Prior Publication Data

US 2006/0210475 A1    Sep. 21, 2006

Related U.S. Application Data

(60) Provisional application No. 60/657,695, filed on Mar. 3, 2005.

(51) Int. Cl.
    *C12P 21/08*    (2006.01)
(52) U.S. Cl. .............. 530/387.3; 530/391.7; 530/391.3; 530/388.22
(58) Field of Classification Search .................... None
    See application file for complete search history.

(56) References Cited

U.S. PATENT DOCUMENTS

| | | | |
|---|---|---|---|
| 5,530,101 | A | 6/1996 | Queen et al. |
| 5,585,089 | A | 12/1996 | Queen et al. |
| 5,693,762 | A | 12/1997 | Queen et al. |
| 5,789,554 | A | 8/1998 | Leung et al. |
| 5,859,205 | A * | 1/1999 | Adair et al. .............. 530/387.3 |
| 6,180,370 | B1 | 1/2001 | Queen et al. |
| 6,180,377 | B1 | 1/2001 | Morgan et al. |
| 6,187,287 | B1 | 2/2001 | Leung et al. |
| 6,730,300 | B2 | 5/2004 | Leung et al. |
| 7,022,500 | B1 | 4/2006 | Queen et al. |
| 2003/0103979 | A1 | 6/2003 | Leung et al. |

OTHER PUBLICATIONS

Altomonte et al. "Targeting of HLA-DR molecules transduces agonistic functional signals in cutaneous melanoma." J Cell Physiol. 2004;200:272-276.
Aoudjit et al. "HLA-DR signaling inhibits Fas-mediated apoptosis in A375 melanoma cells." Exp Cell Res. 2004;299:79-90.
ATCC Deposit HB55.
Blancheteau et al. "HLA class II signals sensitize B lymphocytes to apoptosis via Fas/CD95 by increasing FADD recruitment to activated Fas and activation of caspases." Hum Immunol. 2002;63:375-383.
Bridges et al. "Selective in vivo antitumor effects of monoclonal anti-I-A antibody on a B lymphoma." J Immunol. 1987;139:4242-4249.
Brozek et al. "Anti-DR antibodies inhibit in vitro production of human rheumatoid factor." J Clin Lab Immunol. 1990;31:105-109.
Elsasser et al. "HLA class II as potential target antigen on malignant B cells for therapy with bispecific antibodies in combination with granulocyte colony-stimulating factor." Blood 1996;87:3803-3812.
Fu et al. "HLA-DR alpha chain residues located on the outer loops are involved in non-polymorphic and polymorphic antibody-binding epitopes." Hum Immunol. 1994; 39:253-260.
Gussow et al. "Humanization of monoclonal antibodies." Method Enzymol. 203:99-121, (1991).
Kabelitz et al. "Growth inhibition of Epstein-Barr virus-transformed B cells by anti-HLA-DR antibody L243: possible relationship to L243-induced down-regulation of CD23 antigen expression." Cell Immunol. 1989;120:21-30.
Lampson et al. "Two populations of Ia-like molecules on a human B cell line." J. Immunol. (1980) 125:293-299.
Lund et al. "Expression and characterization of truncated forms of humanized L243 IgG1. Architectural features can influence synthesis of its oligosaccharide chains and affect superoxide production triggered through human Fcgamma receptor I." Eur. J. Biochem. Dec. 2000. vol. 267, No. 24, pp. 7246-7257.
Nagy et al. "Fully human, HLA-DR-specific monoclonal antibodies efficiently induce programmed death of malignant lymphoid cells." Nat Med. 2002;8:801-807.
Stein et al. "Characterization of a humanized IgG4 anti-HLA-DR monoclonal antibody that lacks effector cell functions but retains direct antilymphoma activity and increases the potency of rituximab." Blood 2006;108:2736-44.
Vaswani et al. "Humanized antibodies as potential therapeutic drugs." Ann. Allergy Asthma Immunol. 1998;81:105-119.

* cited by examiner

*Primary Examiner*—Eileen B O'Hara
*Assistant Examiner*—F. Pierre VanderVegt
(74) *Attorney, Agent, or Firm*—Richard A. Nakashima

(57) ABSTRACT

Humanized antibodies are provided that specifically bind HLA-DR. The antibodies recognize the epitope recognized by the murine monoclonal antibody L243. Processes for preparing such antibodies, pharmaceutical compositions containing such antibodies, and clinical therapuetic and diagnostic, as well as research-related uses for such antibodies, are provided.

25 Claims, 24 Drawing Sheets

```
GACATCCAGATGACTCAGTCTCCAGCCTCCCTATCTGTGGGAGAAACTGTCACCATCACATGTCGAGCAAGTGAGAATATTTAC
 1                      10                      20                      30
 D  I  Q  M  T  Q  S  P  A  S  L  S  V  S  V  G  E  T  V  T  I  T  C  R  A  S  E  N  I  Y
                                                                     ─────────────────────
                                                                              CDR1

AGTAATTTAGCATGGTATCGTCAGAAACAGGGAAAATCTCCTCAGCTCCTGGTCTTTGCTGCATCAAACTTAGCAGATGGTGTGCCATCA
                        40                      50                      60
 S  N  L  A  W  Y  R  Q  K  Q  G  K  S  P  Q  L  L  V  F  A  A  S  N  L  A  D  G  V  P  S
 ──────────                                            ──────────────────────
                                                                CDR2

AGGTTCAGTGGCAGTGGATCAGGCACACAGTATTCCCTCAAGATCAACAGCCTGCAGTCTGAAGATTTTGGGGATTATTACTGTCAACAT
                        70                      80                      90
 R  F  S  G  S  G  S  G  T  Q  Y  S  L  K  I  N  S  L  Q  S  E  D  F  G  D  Y  Y  C  Q  H

TTTTGGACTACTCCGTGGGCGTTCGGTGGAGGCACCAACCTGGAAATCAAACGT
                        100                     108
 F  W  T  T  P  W  A  F  G  G  G  T  N  L  E  I  K  R
 ─────────────────────────
         CDR3
```

Figure 2:
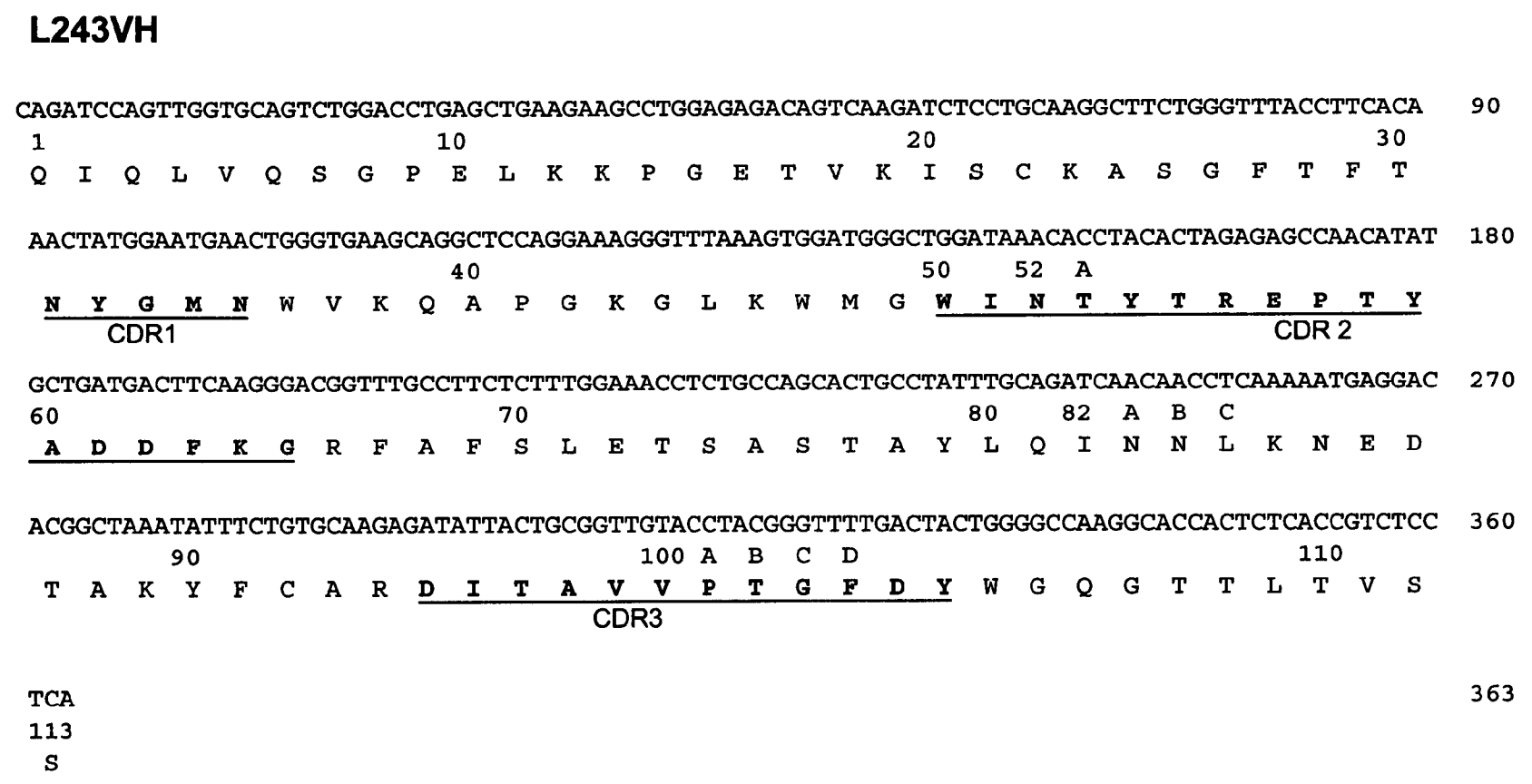

```
CAGATCCAGTTGGTGCAGTCTGGACCTGAGCTGAAGAAGCCTGGAGAGACAGTCAAGATCTCCTGCAAGGCTTCTGGGTTTACCTTCACA    90
  1                                     10                          20                  30
  Q   I   Q   L   V   Q   S   G   P   E   L   K   K   P   G   E   T   V   K   I   S   C   K   A   S   G   F   T   F   T

AACTATGGAATGAACTGGGTGAAGCAGGCTCCAGGAAAGGGTTTAAAGTGGATGGGCTGGATAAACACCTACACTAGAGAGCCAACATAT    180
                    40                          50      52 A                          CDR 2
  N   Y   G   M   N   W   V   K   Q   A   P   G   K   G   L   K   W   M   G   W   I   N   T   Y   T   R   E   P   T   Y
              CDR1

GCTGATGACTTCAAGGGACGGTTTGCCTTCTCTTTGGAAACCTCTGCCAGCACTGCCTATTTGCAGATCAACAACCTCAAAAATGAGGAC    270
  60                          70                          80      82 A B C
  A   D   D   F   K   G   R   F   A   F   S   L   E   T   S   A   S   T   A   Y   L   Q   I   N   N   L   K   N   E   D

ACGGCTAAATATTTCTGTGCAAGAGATATTACTGCGGTTGTACCTACGGGGTTTGACTACTGGGGCCAAGGCACCACTCTCACCGTCTCC    360
                    90                  100 A B C D                          110
  T   A   K   Y   F   C   A   R   D   I   T   A   V   V   P   T   G   F   D   Y   W   G   Q   G   T   T   L   T   V   S
                                              CDR3

TCA    363
113
 S
```

Fig. 3 hL243Vk

```
GACATCCAGCTGACCCAGTCTCCATCATCTCTGAGCGCATCTGTTGGAGATAGGGTCACTATCACTTGTCGAGCAAGTGAGAATATTTAC
 1               10                  20                  30
 D  I  Q  L  T  Q  S  P  S  S  L  S  A  S  V  G  D  R  V  T  I  T  C  R  A  S  E  N  I  Y
                                                              CDR1

AGTAATTTAGCATGGTATCGTCAGAAACCAGGGAAAGCACCTAAACTGCTGGTCTTTGCTGCATCAAACTTAGCAGATGGTGTGCCTTCG
          40                  50                  60
 S  N  L  A  W  Y  R  Q  K  P  G  K  A  P  K  L  L  V  F  A  A  S  N  L  A  D  G  V  P  S
                                              CDR2

CGATTCTCTGGCAGCGGATCTGGACAGATTATACTTTCACCATCAGCTCTCTTCAACCAGAAGACATTGCAACATATTATTGTCAACAT
              70                  80                  90
 R  F  S  G  S  G  S  G  T  D  Y  T  F  T  I  S  S  L  Q  P  E  D  I  A  T  Y  Y  C  Q  H

TTTTGGACTACTCCGTGGGCGTTCGGTGGAGGGACCAAGCTGCAGATCAAACGT
                      100             108
 F  W  T  T  P  W  A  F  G  G  G  T  K  L  Q  I  R  K
 CDR3
```

```
CAGGTGCAACTGCAGCAATCTGGGTCTGAGTTGAAGAAGCCTGGGGCCTCAGTGAAGGTTTCCTGCAAGGCTTCTGGATTTACCTTCACA        90
  1                         10                      20                      30
  Q  V  Q  L  Q  Q  S  G  S  E  L  K  K  P  G  A  S  V  K  V  S  C  K  A  S  G  F  T  F  T

AACTATGGAATGAACTGGGTGAAGCAGGCCCCTGGACAAGGGCTTAAGTGGATGGGCTGGATAAACACCTACACTAGAGAGCCAACATAT        180
                40                      50  52 A
  N  Y  G  M  N  W  V  K  Q  A  P  G  Q  G  L  K  W  M  G  W  I  N  T  Y  T  R  E  P  T  Y
       CDR1                                              CDR 2

GCTGATGACTTCAAAGGGACGGTTTGCCTTCTCCTTGGACACCTCTGTCAGCACGGCATATCTCCAGATCAGCAGCCTAAAGGCTGACGAC        270
  60                      70                      80  82 A B C
  A  D  D  F  K  G  R  F  A  F  S  L  D  T  S  V  S  T  A  Y  L  Q  I  S  S  L  K  A  D  D

ACTGCCGTGTATTTCTGTGCAAGAGATATTACTGCGGTTGTACCTACGGGGTTTTGACTACTGGGGCCAAGGGTCCCTGGTCACCGTCTCC        360
                90                     100 A B C D             110
  T  A  V  Y  F  C  A  R  D  I  T  A  V  V  P  T  G  F  F  D  Y  W  G  Q  G  S  L  V  T  V  S
                            CDR3

TCA                                                                                              363
113
 S
```

Figure 5

```
              1                  10              20                30            40
RF-TS3   -VQLVQSGSELKKPGASVKVSCKASGYTFTSYAMNWVRQA
L243     ····QI···············P·······ET···I········F···N·G···K···
hL343    ····Q······Q·········P················F···N·G···K···
                                   ─────────

50 52A                                         70
RF-TS    PGQGLEWMGWINTNTGNPTYAQGFTGRFVFSLDTSVSTAY
L243     ·······KG·K······Y·RE···DD·K···A···E··A···
hL343    ··········K···············Y·RE···DD·K···A······A···
                    ──────────────────

80 82ABC         90                   100ABCD 102
RF-TS3   LQISSLKADDTAVYYCAREDSNGYKI-FDY
L243     ····NN···NE···K·F······EDSNGYKI-FDY
hL343    ·······················DITAVVPTG···
                              ·······DITAVVPTG···
                              ─────────────────────

103        110  113
NEWM     WGQGSLVTVSS
L243     ····TTL···
hL243    ····TTL···
         ──────────
```

Figure 6

```
                1                   10                  20                  30         40
REIVk           D I Q M T Q S P S S L S A S V G D R V T I T C Q A S Q D I I K Y L N W Y Q Q T P
L243Vk          · · · · · · · · · · · · · A · · V · · E T · · · · · R · · Y S N · A · · R · K Q
hL243Vk         D I Q L · · · · · · · · · · · · · · · · · · · · · R · · Y S N · A · · R · K ·

50                  60                  70         80
REIVk           G K A P K L L I Y E A S N L Q A G V P S R F S G S G S G T D Y T F T I S S L Q P
L243Vk          · · S · Q · · · · V F A · · A D · · · · · · · · · · · · · · · · Q · S L K · N S
hL243Vk         · · · · · · · · · V F A · · A D · · · · · · · · · · · · · · · · · · · · · · · ·

90                  100          108
REIVk           E D I A T Y Y C Q Q Y Q S L P Y T F G Q G T K L Q I T -
L243Vk          · · F G D · · · · · H F W T T · W A · · · · · N · E · K R
hL243Vk         · · F G D · · · · · H F W T T · W A · · · · · · · · I K R
```

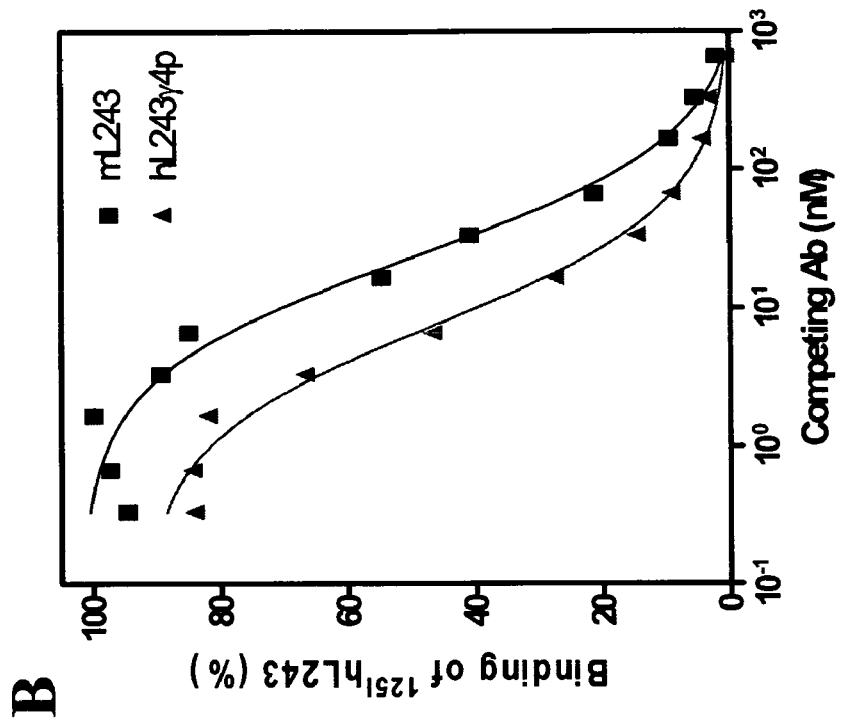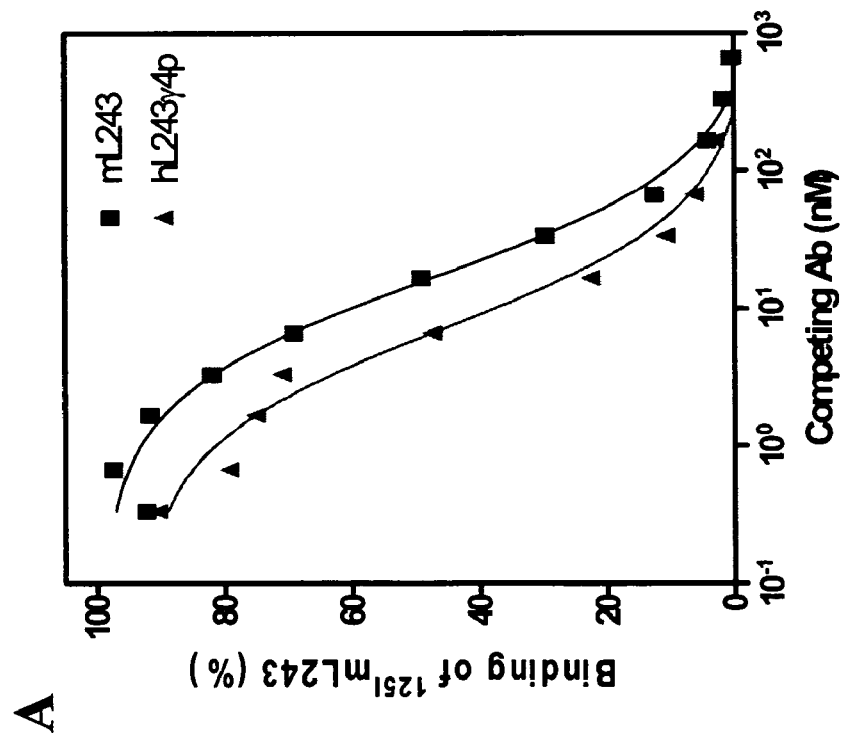
Fig. 8

Fig. 20
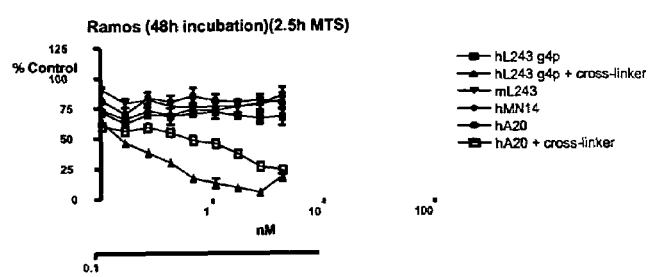
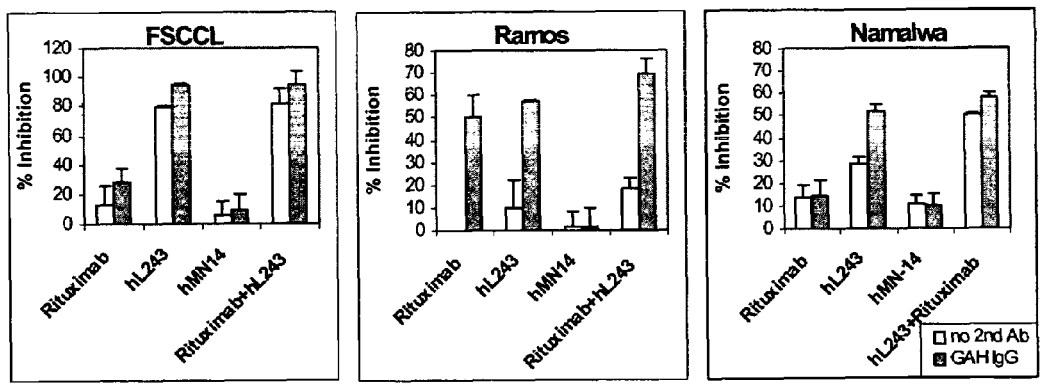

Fig. 21
A
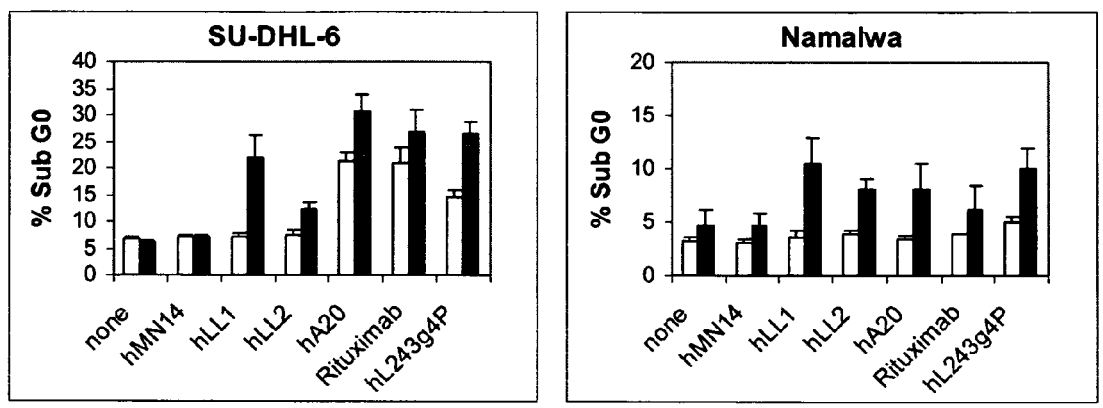
B
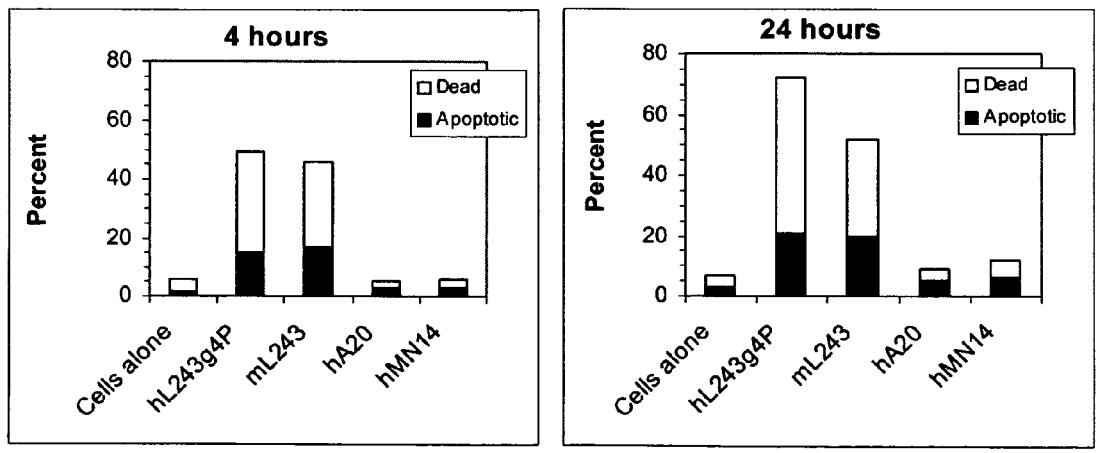

Fig. 23
A
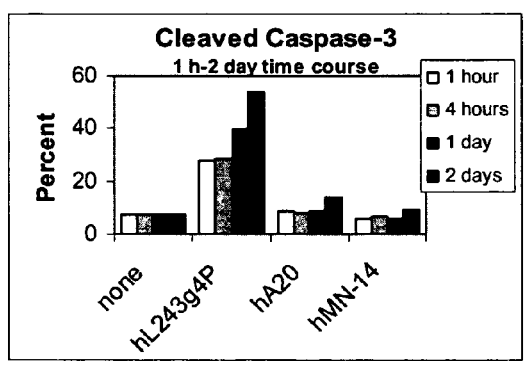
B
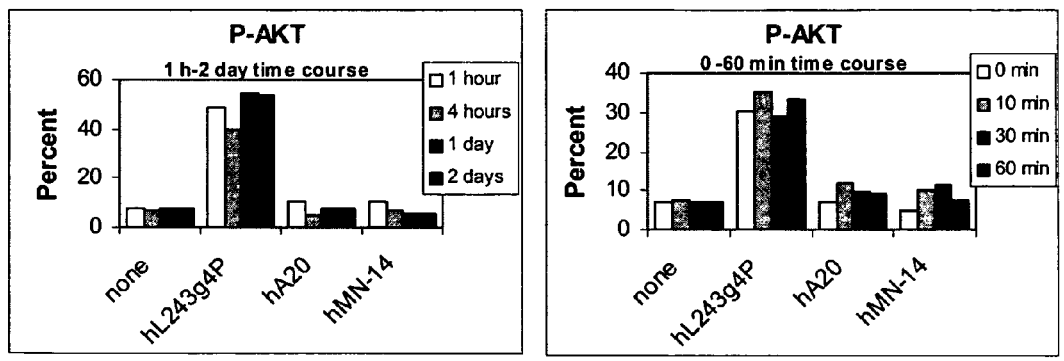

MST: median survival time

SEQUENCE LISTING

<160> NUMBER OF SEQ ID NOS: 25

<210> SEQ ID NO 1
<211> LENGTH: 324
<212> TYPE: DNA
<213> ORGANISM: mouse anti-HLA-DR antibody
<220> FEATURE:
<221> NAME/KEY: CDS
<222> LOCATION: (1)..(321)

<400> SEQUENCE: 1

```
gac atc cag atg act cag tct cca gcc tcc cta tct gta tct gtg gga      48
Asp Ile Gln Met Thr Gln Ser Pro Ala Ser Leu Ser Val Ser Val Gly
 1               5                  10                  15 gaa act gtc acc atc aca tgt cga gca agt gag aat att tac agt aat      96
Glu Thr Val Thr Ile Thr Cys Arg Ala Ser Glu Asn Ile Tyr Ser Asn
             20                  25                  30 tta gca tgg tat cgt cag aaa cag gga aaa tct cct cag ctc ctg gtc     144
Leu Ala Trp Tyr Arg Gln Lys Gln Gly Lys Ser Pro Gln Leu Leu Val
         35                  40                  45 ttt gct gca tca aac tta gca gat ggt gtg cca tca agg ttc agt ggc     192
Phe Ala Ala Ser Asn Leu Ala Asp Gly Val Pro Ser Arg Phe Ser Gly
     50                  55                  60 agt gga tca ggc aca cag tat tcc ctc aag atc aac agc ctg cag tct     240
Ser Gly Ser Gly Thr Gln Tyr Ser Leu Lys Ile Asn Ser Leu Gln Ser
 65                  70                  75                  80 gaa gat ttt ggg gat tat tac tgt caa cat ttt tgg act act ccg tgg     288
Glu Asp Phe Gly Asp Tyr Tyr Cys Gln His Phe Trp Thr Thr Pro Trp
                 85                  90                  95 gcg ttc ggt gga ggc acc aac ctg gaa atc aaa cgt                     324
Ala Phe Gly Gly Gly Thr Asn Leu Glu Ile Lys
            100                 105
```

<210> SEQ ID NO 2
<211> LENGTH: 107
<212> TYPE: PRT
<213> ORGANISM: mouse anti-HLA-DR antibody

<400> SEQUENCE: 2

Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Tyr Ser Asn
             20                  25                  30

Leu Ala Trp Tyr Arg Gln Lys Gln Gly Lys Ser Pro Gln Leu Leu Val
         35                  40                  45

Phe Ala Ala Ser Asn Leu Ala Asp Gly Val Pro Ser Arg Phe Ser Gly
     50                  55                  60

Ser Gly Ser Gly Thr Gln Tyr Ser Leu Lys Ile Asn Ser Leu Gln Ser
 65                  70                  75                  80

Glu Asp Phe Gly Asp Tyr Tyr Cys Gln His Phe Trp Thr Thr Pro Trp
                 85                  90                  95

Ala Phe Gly Gly Gly Thr Asn Leu Glu Ile Lys
            100                 105

<210> SEQ ID NO 3
<211> LENGTH: 363
<212> TYPE: DNA
<213> ORGANISM: Mouse anti-HLA-DR antibody L243
<220> FEATURE:
<221> NAME/KEY: CDS

```
<222> LOCATION: (1)..(360)

<400> SEQUENCE: 3 cag atc cag ttg gtg cag tct gga cct gag ctg aag aag cct gga gag    48
Gln Ile Gln Leu Val Gln Ser Gly Pro Glu Leu Lys Lys Pro Gly Glu
 1               5                  10                  15 aca gtc aag atc tcc tgc aag gct tct ggg ttt acc ttc aca aac tat    96
Thr Val Lys Ile Ser Cys Lys Ala Ser Gly Phe Thr Phe Thr Asn Tyr
             20                  25                  30 gga atg aac tgg gtg aag cag gct cca gga aag ggt tta aag tgg atg   144
Gly Met Asn Trp Val Lys Gln Ala Pro Gly Lys Gly Leu Lys Trp Met
         35                  40                  45 ggc tgg ata aac acc tac act aga gag cca aca tat gct gat gac ttc   192
Gly Trp Ile Asn Thr Tyr Thr Arg Glu Pro Thr Tyr Ala Asp Asp Phe
     50                  55                  60 aag gga cgg ttt gcc ttc tct ttg gaa acc tct gcc agc act gcc tat   240
Lys Gly Arg Phe Ala Phe Ser Leu Glu Thr Ser Ala Ser Thr Ala Tyr
 65                  70                  75                  80 ttg cag atc aac aac ctc aaa aat gag gac acg gct aaa tat ttc tgt   288
Leu Gln Ile Asn Asn Leu Lys Asn Glu Asp Thr Ala Lys Tyr Phe Cys
                 85                  90                  95 gca aga gat att act gcg gtt gta cct acg ggt ttt gac tac tgg ggc   336
Ala Arg Asp Ile Thr Ala Val Val Pro Thr Gly Phe Asp Tyr Trp Gly
            100                 105                 110 caa ggc acc act ctc acc gtc tcc tca                               363
Gln Gly Thr Thr Leu Thr Val Ser
        115                 120

<210> SEQ ID NO 4
<211> LENGTH: 120
<212> TYPE: PRT
<213> ORGANISM: Mouse anti-HLA-DR antibody L243

<400> SEQUENCE: 4

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Phe Thr Phe Thr Asn Tyr
             20                  25                  30

Gly Met Asn Trp Val Lys Gln Ala Pro Gly Lys Gly Leu Lys Trp Met
         35                  40                  45

Gly Trp Ile Asn Thr Tyr Thr Arg Glu Pro Thr Tyr Ala Asp Asp Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Lys Tyr Phe Cys
                 85                  90                  95

Ala Arg Asp Ile Thr Ala Val Val Pro Thr Gly Phe Asp Tyr Trp Gly
            100                 105                 110

Gln Gly Thr Thr Leu Thr Val Ser
        115                 120

<210> SEQ ID NO 5
<211> LENGTH: 324
<212> TYPE: DNA
<213> ORGANISM: humanized mouse antibody
<220> FEATURE:
<221> NAME/KEY: CDS
<222> LOCATION: (1)..(324)

<400> SEQUENCE: 5
```

```
gac atc cag ctg acc cag tct cca tca tct ctg agc gca tct gtt gga        48
Asp Ile Gln Leu Thr Gln Ser Pro Ser Ser Leu Ser Ala Ser Val Gly
1               5                   10                  15 gat agg gtc act atc act tgt cga gca agt gag aat att tac agt aat        96
Asp Arg Val Thr Ile Thr Cys Arg Ala Ser Glu Asn Ile Tyr Ser Asn
                20                  25                  30 tta gca tgg tat cgt cag aaa cca ggg aaa gca cct aaa ctg ctg gtc       144
Leu Ala Trp Tyr Arg Gln Lys Pro Gly Lys Ala Pro Lys Leu Leu Val
            35                  40                  45 ttt gct gca tca aac tta gca gat ggt gtg cct tcg cga ttc tct ggc       192
Phe Ala Ala Ser Asn Leu Ala Asp Gly Val Pro Ser Arg Phe Ser Gly
        50                  55                  60 agc gga tct ggg aca gat tat act ttc acc atc agc tct ctt caa cca       240
Ser Gly Ser Gly Thr Asp Tyr Thr Phe Thr Ile Ser Ser Leu Gln Pro
65                  70                  75                  80 gaa gac att gca aca tat tat tgt caa cat ttt tgg act act ccg tgg       288
Glu Asp Ile Ala Thr Tyr Tyr Cys Gln His Phe Trp Thr Thr Pro Trp
                85                  90                  95 gcg ttc ggt gga ggg acc aag ctg cag atc aaa cgt                       324
Ala Phe Gly Gly Gly Thr Lys Leu Gln Ile Lys Arg
            100                 105
```

<210> SEQ ID NO 6
<211> LENGTH: 108
<212> TYPE: PRT
<213> ORGANISM: humanized mouse antibody

<400> SEQUENCE: 6

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
                20                  25                  30

Leu Ala Trp Tyr Arg Gln Lys Pro Gly Lys Ala Pro Lys Leu Leu Val
            35                  40                  45

Phe Ala Ala Ser Asn Leu Ala Asp Gly Val Pro Ser Arg Phe Ser Gly
        50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Thr Thr Pro Trp
                85                  90                  95

Ala Phe Gly Gly Gly Thr Lys Leu Gln Ile Lys Arg
            100                 105

<210> SEQ ID NO 7
<211> LENGTH: 363
<212> TYPE: DNA
<213> ORGANISM: humanized mouse antibody
<220> FEATURE:
<221> NAME/KEY: CDS
<222> LOCATION: (1)..(363)

<400> SEQUENCE: 7

```
cag gtg caa ctg cag caa tct ggg tct gag ttg aag aag cct ggg gcc        48
Gln Val Gln Leu Gln Gln Ser Gly Ser Glu Leu Lys Lys Pro Gly Ala
1               5                   10                  15 tca gtg aag gtt tcc tgc aag gct tct gga ttt acc ttc aca aac tat        96
Ser Val Lys Val Ser Cys Lys Ala Ser Gly Phe Thr Phe Thr Asn Tyr
                20                  25                  30 gga atg aac tgg gtg aag cag gcc cct gga caa ggg ctt aag tgg atg       144
Gly Met Asn Trp Val Lys Gln Ala Pro Gly Gln Gly Leu Lys Trp Met
            35                  40                  45
```

```
ggc tgg ata aac acc tac act aga gag cca aca tat gct gat gac ttc     192
Gly Trp Ile Asn Thr Tyr Thr Arg Glu Pro Thr Tyr Ala Asp Asp Phe
        50                  55                  60 aag gga cgg ttt gcc ttc tcc ttg gac acc tct gtc agc acg gca tat     240
Lys Gly Arg Phe Ala Phe Ser Leu Asp Thr Ser Val Ser Thr Ala Tyr
 65                  70                  75                  80 ctc cag atc agc agc cta aag gct gac gac act gcc gtg tat ttc tgt     288
Leu Gln Ile Ser Ser Leu Lys Ala Asp Asp Thr Ala Val Tyr Phe Cys
                 85                  90                  95 gca aga gat att act gcg gtt gta cct acg ggt ttt gac tac tgg ggc     336
Ala Arg Asp Ile Thr Ala Val Val Pro Thr Gly Phe Asp Tyr Trp Gly
            100                 105                 110 caa ggg tcc ctg gtc acc gtc tcc tca                                 363
Gln Gly Ser Leu Val Thr Val Ser Ser
        115                 120
```

<210> SEQ ID NO 8
<211> LENGTH: 121
<212> TYPE: PRT
<213> ORGANISM: humanized mouse antibody

<400> SEQUENCE: 8

```
Gln Val Gln Leu Gln Gln Ser Gly Ser Glu Leu Lys Lys Pro Gly Ala
 1               5                  10                  15

Ser Val Lys Val Ser Cys Lys Ala Ser Gly Phe Thr Phe Thr Asn Tyr
                 20                  25                  30

Gly Met Asn Trp Val Lys Gln Ala Pro Gly Gln Gly Leu Lys Trp Met
            35                  40                  45

Gly Trp Ile Asn Thr Tyr Thr Arg Glu Pro Thr Tyr Ala Asp Asp Phe
        50                  55                  60

Lys Gly Arg Phe Ala Phe Ser Leu Asp Thr Ser Val Ser Thr Ala Tyr
 65                  70                  75                  80

Leu Gln Ile Ser Ser Leu Lys Ala Asp Asp Thr Ala Val Tyr Phe Cys
                 85                  90                  95

Ala Arg Asp Ile Thr Ala Val Val Pro Thr Gly Phe Asp Tyr Trp Gly
            100                 105                 110

Gln Gly Ser Leu Val Thr Val Ser Ser
        115                 120
```

<210> SEQ ID NO 9
<211> LENGTH: 108
<212> TYPE: PRT
<213> ORGANISM: homo sapiens

<400> SEQUENCE: 9

```
Val Gln Leu Val Gln Ser Gly Ser Glu Leu Lys Lys Pro Gly Ala Ser
 1               5                  10                  15

Val Lys Val Ser Cys Lys Ala Ser Gly Tyr Thr Phe Thr Ser Tyr Ala
                 20                  25                  30

Met Asn Trp Val Arg Gln Ala Pro Gly Gln Gly Leu Glu Trp Met Gly
            35                  40                  45

Trp Ile Asn Thr Asn Thr Gly Asn Pro Thr Tyr Ala Gln Gly Phe Thr
        50                  55                  60

Gly Arg Phe Val Phe Ser Leu Asp Thr Ser Val Ser Thr Ala Tyr Leu
 65                  70                  75                  80

Gln Ile Ser Ser Leu Lys Ala Asp Asp Thr Ala Val Tyr Tyr Cys Ala
                 85                  90                  95
```

Arg Glu Asp Ser Asn Gly Tyr Lys Ile Phe Asp Tyr
            100                 105

<210> SEQ ID NO 10
<211> LENGTH: 121
<212> TYPE: PRT
<213> ORGANISM: Murinae gen. sp.

<400> SEQUENCE: 10

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Arg Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Lys Tyr Phe Cys
                85                  90                  95

Ala Arg Asp Ile Thr Ala Val Val Pro Thr Gly Phe Asp Tyr Trp Gly
            100                 105                 110

Gln Gly Thr Thr Leu Thr Val Ser Ser
        115                 120

<210> SEQ ID NO 11
<211> LENGTH: 121
<212> TYPE: PRT
<213> ORGANISM: humanized antibody

<400> SEQUENCE: 11

Gln Val Gln Leu Gln Gln Ser Gly Ser Glu Leu Lys Lys Pro Gly Ala
1               5                   10                  15

Ser Val Lys Val Ser Cys Lys Ala Ser Gly Phe Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Arg Glu Pro Thr Tyr Ala Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Asp Ile Thr Ala Val Val Pro Thr Gly Phe Asp Tyr Trp Gly
            100                 105                 110

Gln Gly Ser Leu Val Thr Val Ser Ser
        115                 120

<210> SEQ ID NO 12
<211> LENGTH: 119
<212> TYPE: PRT
<213> ORGANISM: Homo sapiens

<400> SEQUENCE: 12

Val Gln Leu Val Gln Ser Gly Ser Glu Leu Lys Lys Pro Gly Ala Ser
1               5                   10                  15

Val Lys Val Ser Cys Lys Ala Ser Gly Tyr Thr Phe Thr Ser Tyr Ala

-continued

```
                    20                  25                  30
Met Asn Trp Val Arg Gln Ala Pro Gly Gln Gly Leu Glu Trp Met Gly
            35                  40                  45

Trp Ile Asn Thr Asn Thr Gly Asn Pro Thr Tyr Ala Gln Gly Phe Thr
        50                  55                  60

Gly Arg Phe Val Phe Ser Leu Asp Thr Ser Val Ser Thr Ala Tyr Leu
65                  70                  75                  80

Gln Ile Ser Ser Leu Lys Ala Asp Asp Thr Ala Val Tyr Tyr Cys Ala
                85                  90                  95

Arg Glu Asp Ser Asn Gly Tyr Lys Ile Phe Asp Tyr Trp Gly Gln Gly
            100                 105                 110

Ser Leu Val Thr Val Ser Ser
        115
```

<210> SEQ ID NO 13
<211> LENGTH: 107
<212> TYPE: PRT
<213> ORGANISM: homo sapiens

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                  30

Leu Asn Trp Tyr Gln Gln Thr Pro Gly Lys Ala Pro Lys Leu Leu Ile
        35                  40                  45

Tyr Glu Ala Ser Asn Leu Gln Ala Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Gln Ser Leu Pro Tyr
                85                  90                  95

Thr Phe Gly Gln Gly Thr Lys Leu Gln Ile Thr
            100                 105
```

<210> SEQ ID NO 14
<211> LENGTH: 108
<212> TYPE: PRT
<213> ORGANISM: mouse

<400> SEQUENCE: 14

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Arg Gln Lys Gln Gly Lys Ser Pro Gln Leu Leu Val
        35                  40                  45

Phe Ala Ala Ser Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Asp Tyr Tyr Cys Gln His Phe Trp Thr Thr Pro Trp
                85                  90                  95

Ala Phe Gly Gly Gly Thr Asn Leu Glu Ile Lys Arg
            100                 105
```

<210> SEQ ID NO 15
<211> LENGTH: 108
<212> TYPE: PRT
<213> ORGANISM: humanized mouse

<400> SEQUENCE: 15

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Arg Gln Lys Pro Gly Lys Ala Pro Lys Leu Leu Val
        35                  40                  45

Phe Ala Ala Ser Asn Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Thr Thr Pro Trp
                85                  90                  95

Ala Phe Gly Gly Gly Thr Lys Leu Gln Ile Lys Arg
            100                 105

<210> SEQ ID NO 16
<211> LENGTH: 175
<212> TYPE: DNA
<213> ORGANISM: humanized mouse

<400> SEQUENCE: 16
ggtctgagtt gaagaagcct ggggcctcag tgaaggtttc ctgcaaggct tctggattta      60
ccttcacaaa ctatggaatg aactgggtga agcaggcccc tggacaaggg cttaagtgga     120
tgggctggat aaacacctac actagagagc caacatatgc tgatgacttc aaggg         175

<210> SEQ ID NO 17
<211> LENGTH: 168
<212> TYPE: DNA
<213> ORGANISM: humanized mouse

<400> SEQUENCE: 17
acccttggcc ccagtagtca aacccgtag gtacaaccgc agtaatatct cttgcacaga      60
aatacacggc agtgtcgtca gcctttaggc tgctgatctg agatatgcc gtgctgacag     120 aggtgtccaa ggagaaggca aaccgtccct tgaagtcatc agcatatg                 168

<210> SEQ ID NO 18
<211> LENGTH: 38
<212> TYPE: DNA
<213> ORGANISM: humanized mouse

<400> SEQUENCE: 18
gtggtgctgc agcaatctgg gtctgagttg aagaagcc                             38

<210> SEQ ID NO 19
<211> LENGTH: 38
<212> TYPE: DNA
<213> ORGANISM: humanized mouse

<400> SEQUENCE: 19
tgaggagacg gtgaccaggg acccttggcc ccagtagt                             38

<210> SEQ ID NO 20
<211> LENGTH: 155

```
<212> TYPE: DNA
<213> ORGANISM: humanized mouse

<400> SEQUENCE: 20
tccatcatct ctgagcgcat ctgttggaga tagggtcact atcacttgtc gagcaagtga      60
gaatatttac agtaatttag catggtatcg tcagaaacca gggaaagcac ctaaactgct     120
ggtctttgct gcatcaaact agcagatgg tgtgc                                 155

<210> SEQ ID NO 21
<211> LENGTH: 159
<212> TYPE: DNA
<213> ORGANISM: humanized mouse

<400> SEQUENCE: 21
cagcttggtc cctccaccga acgcccacgg agtagtccaa aaatgttgac aataatatgt      60
tgcaatgtct tctggttgaa gagagctgat ggtgaaagta taatctgtcc cagatccgct     120
gccagagaat cgcgaaggca caccatctgc taagtttga                            159

<210> SEQ ID NO 22
<211> LENGTH: 38
<212> TYPE: DNA
<213> ORGANISM: humanized mouse

<400> SEQUENCE: 22
gacattcagc tgacccagtc tccatcatct ctgagcgc                              38

<210> SEQ ID NO 23
<211> LENGTH: 31
<212> TYPE: DNA
<213> ORGANISM: humanized mouse

<400> SEQUENCE: 23
ccggcagatc tgcagcttgg tccctccacc g                                     31

<210> SEQ ID NO 24
<211> LENGTH: 47
<212> TYPE: DNA
<213> ORGANISM: mouse

<400> SEQUENCE: 24
ccgcggtcac atggcaccac ctctcttgca gcttccacca agggccc                    47

<210> SEQ ID NO 25
<211> LENGTH: 33
<212> TYPE: DNA
<213> ORGANISM: mouse

<400> SEQUENCE: 25
ccggccgtcg cactcattta cccagagaca ggg                                   33
```

HUMANIZED L243 ANTIBODIES

CROSS REFERENCE TO RELATED APPLICATIONS

This application claims the benefit under 35 U.S.C. §119 (e) of provisional U.S. patent application Ser. No. 60/657,695 filed on Mar. 3, 2005. The aforementioned application is hereby incorporated by reference in its entirety for all purposes.

FIELD

The present invention relates to humanized antibodies directed to an epitope recognized by murine monoclonal antibody L243. In one embodiment, the present invention relates to compositions and methods for preparing and using such antibodies. In particular, the present invention provides for a humanized monoclonal antibody, hL243, that is specific for the human leucocyte antigen (HLA) encoded in the D region of the HLA gene cluster of the major histocompatibility complex (MHC), otherwise known as HLA-DR. The antibody inhibits proliferation of HLA-DR+ cells and induces expression and release of TNF molecules.

BACKGROUND

In humans, the major histocompatibility complex (MHC) is the human leucocyte antigen (HLA) gene cluster on chromosome 6, which is divided into regions termed D, B, C, and A. The D region contains genes for Class II proteins, which are involved in cooperation and interaction between cells of the immune system. The D region has been implicated in many diseases including most autoimmune diseases.

One antibody, L243 (hereafter mL243) is a murine IgG2a anti-HLA-DR antibody. This antibody may be of potential use in the treatment of diseases such as autoimmune diseases by targeting the D region of the mouse HLA gene. mL243 demonstrates potent suppression of in vitro immune function and is monomorphic for all HLA-DR. However, problems exist with the administration of mouse antibodies to human patients, such as the induction of a human anti-mouse antibody (HAMA) response. A need exists for antibodies with the antigenic specificity of mL243, that may be administered to human subjects

SUMMARY

One embodiment of the present invention provides for a recombinant humanized antibody molecule having specificity for the epitope recognized by the murine monoclonal antibody mL243. This epitope can be an antigenic determinant dependent on the DR-α chain. In accordance with this embodiment, the antibody may be a humanized CDR-grafted antibody.

For example, in one embodiment, the humanized antibody molecule having specificity for the epitope recognized by the murine monoclonal antibody mL243 has an antigen binding site wherein at least one of the complementarity determining regions (CDRs) of the variable domain is derived from the mouse monoclonal antibody mL243 (MAb L243) and the remaining immunoglobulin-derived parts of the humanized antibody molecule are derived from a human immunoglobulin or an analogue thereof. In one particular embodiment of the present invention, all three heavy and light chain CDRs of a humanized antibody are derived from mAb mL243. In another embodiment of the present invention, the humanized antibody molecule may be conjugated to an effector or a reporter molecule.

In one example, the present invention provides for a humanized L243 antibody having a heavy chain variable domain where the CDR1, CDR2, and CDR3 regions and one or more framework residues 27, 38, 46, 68 and 91 of the variable domain are from the mouse monoclonal antibody mL243 heavy chain and the remainder of the immunoglobulin framework domains are from one or more human heavy chains. In accordance with this example, the antibody may bind to at least one epitope of HLA-DR on HLA-DR+ cells, and increases killing of the cells. In one particular embodiment, cell killing may be increased where neither cytotoxic addends nor immunological effector mechanisms are needed for the killing.

In another embodiment of the present invention, a humanized L243 antibody may include a light chain variable domain where the CDR1, CDR2, and CDR3 regions and one or more framework residues 37, 39, 48 and 49 of the variable domain are from the mouse monoclonal antibody mL243 light chain and the remainder of the immunoglobulin framework domains are from one or more human light chains. In accordance with this embodiment, the antibody may bind to at least one epitope of HLA-DR on HLA-DR* cells, and increases killing of the cells. In one particular embodiment, cell killing may be increased where neither cytotoxic addends nor immunological effector mechanisms are needed for the killing.

In another embodiment of the present invention, a humanized L243 antibody may include a heavy chain variable domain and a light chain variable domain, where the CDR1, CDR2, and CDR3 regions and one or more framework residues 27, 38, 46, 68 and 91 of the heavy chain variable domain are from the mouse monoclonal antibody mL243 heavy chain and the remainder of the immunoglobulin heavy chain framework domains are from one or more human heavy chains. In accordance with this embodiment, a humanized L243 antibody may include a heavy chain variable domain and a light chain variable domain where the CDR1, CDR2, and CDR3 regions and one or more framework residues 37, 39, 48 and 49 of the light chain variable domain are from the mouse monoclonal antibody mL243 light chain and the remainder of the immunoglobulin light chain framework domains are from one or more human light chains. In addition, the antibody may bind to at least one epitope of HLA-DR on HLA-DR+ cells, and increases killing of the cells. In one particular embodiment, cell killing may be increased where neither cytotoxic addends nor immunological effector mechanisms are needed for the killing.

In one embodiment of the present invention, any one of the antibodies as described supra may be used in a pharmaceutical composition. In accordance with this embodiment, a pharmaceutical composition including one or more antibodies described herein may contain further therapeutic agents as described below.

In addition, one embodiment in the present invention provides for nucleic acid molecules that encode one or more of the disclosed antibody compositions, conjugates and fusion proteins as described infra. Expression vectors and host cells containing these nucleic acids may also be included.

In accordance with these embodiments, methods for making the antibodies such as the use of host cells cultured in a suitable growth medium for generating the antibodies may be included.

In one embodiment of the present invention, one or more of the disclosed antibodies of the invention may be used in a pharmaceutical composition for therapeutic and/or diagnostic purposes. For example, one or more antibodies may be administered in a therapeutic or pharmaceutical composition to a subject in need of such a treatment (e.g. a subject having an immune disease such as an autoimmune disease).

In a more particular embodiment of the present invention, the humanized L243 antibody has a heavy chain variable domain having the sequence shown in FIG. 4 and/or a light chain variable domain having the sequence shown in FIG. 3.

In another embodiment, a pharmaceutical composition may further contain one or more additional binding molecules which specifically bind to one or more antigens selected from the group consisting of CD4, CDS, CDS, CD14, CD15, CD19, CD20, CD21, CD22, CD23, CD25, CD30, CD33, CD37, CD38, CD40, CD40L, CD46, CD52, CD54, CD66 (a,b,c,d), CD74, CD80, CD126, CD138, CD154, B7, MUC1, MUC2, MUC3, MUC4, MUC16, la, HM1.24, tenascin, VEGF, EGFR, CEA, CSAp, ILGF, placental growth factor, Her2/neu, carbonic anhydrase IX, IL-6, S100, MART-1, TRP-1, TRP-2, gp100, amyloid and combinations thereof, where the additional binding molecule is given before, with, or after any pharmaceutical composition disclosed herein containing a humanized L243 antibody composition and/or a delivery vehicle for the antibody.

In one embodiment, a pharmaceutical composition for administering to a subject in need of such a treatment may contain a humanized L243 antibody and one or more peptides, lipids, polymeric carriers, micelles, nanoparticles, or combinations thereof, and one or more effectors.

One or more of the disclosed methods of the present invention may be used to treat a disease including but not limited to B cell non-Hodgkin lymphomas, B cell acute and chronic lymphoid leukemias, Burkitt lymphoma, Hodgkin lymphoma, hairy cell leukemia, acute and chronic myeloid leukemias, T cell lymphomas and leukemias, multiple myeloma, Waldenstrom's macroglobulinemia, carcinomas, melanomas, sarcomas, gliomas, and skin cancers. The carcinomas may be selected from the group consisting of carcinomas of the oral cavity, gastrointestinal tract, pulmonary tract, breast, ovary, prostate, uterus, urinary bladder, pancreas, liver, gall bladder, skin, and testes. In addition, one or more of the disclosed methods may be used to treat an autoimmune disease, for example acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

In one embodiment, a pharmaceutical composition of the present invention may be use to treat a subject having leukemia, such as chronic lymphocytic leukemia, acute lymphocytic leukemia, chronic myeloid leukemia or acute myeloid leukemia.

In one embodiment, a pharmaceutical composition of the present invention may be use to treat a subject having a metabolic disease, such amyloidosis, or a neurodegenerative disease, such as Alzheimer's disease. In addition, a pharmaceutical composition of the present invention may be use to treat a subject having an immune-dysregulatory disorder.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the present invention will become apparent to those skilled in the art from this detailed description.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein FIG. 1 (also SEQ ID NO:1 and SEQ ID NO:2) illustrates an exemplary DNA encoding and amino acid sequences of VK of the mouse anti-HLA-DR antibody L243. The putative CDR regions are underlined and indicated. Nucleotide residues are numbered sequentially. Kabat's Ig molecule numbering is used for amino acid residues. The numbering for the residues with a letter (on top) is the number of preceding residues plus the letter, e.g., the number for T following N52 is 52A; the numbers for N, N and L following 82 are 82A, 82B and 82C, respectively.

FIG. 2 (also SEQ ID NO:3 and SEQ ID NO:4) illustrates an exemplary DNA encoding and amino acid sequences of VH of the mouse anti-HLA-DR antibody L243. The putative CDR regions are underlined and indicated. Nucleotide residues are numbered sequentially. Kabat's Ig molecule numbering is used for amino acid residues as described above.

FIG. 3 (also SEQ ID NO:5 and SEQ ID NO:6) illustrates an exemplary DNA and amino acid sequences of humanized L243 VR. The bold and underlined sections of the amino acid sequences indicate the CDRs as defined by the Kabat numbering scheme.

FIG. 4 (also SEQ ID NO:7 and SEQ ID NO:8) illustrates an exemplary DNA and amino acid sequences for humanized L243 VH. The bold and underlined sections of the amino acid sequences indicate the CDRs as defined by the Kabat numbering scheme.

FIG. 5 (also SEQ ID NO:9, SEQ ID NO:10, SEQ ID NO:11 and SEQ ID NO:12) illustrates an exemplary amino acid sequence alignment of human RF-TS3 and NEWM (framework 4), murine L243, and hL243 VH chain. Dots indicate the residues in L243 and its humanized version are identical to the corresponding residues in RF-TS3 or NEWM. Dashes represent gaps introduced to aid the alignment. Boxes represent the CDR regions. Both N- and C-terminal residues (underlined) of hL243 are fixed by the staging vector used. Therefore, the corresponding terminal residues of L243 are not compared with that of the human VH sequence.

FIG. 6 (also SEQ ID NO:13, SEQ ID NO:14 and SEQ ID NO:15) illustrates an exemplary amino acid sequence alignment of human REI, murine L243, and hL243 VK chains. Dots indicate the residues in L243 that are identical to the corresponding residues in REI. Dashes represent gaps introduced to aid the alignment. Boxes represent the CDR regions. Both N- and C-terminal residues (underlined) of hL243 are fixed by the staging vector used. Therefore, the corresponding terminal residues of L243 are not compared with that of the human sequence. Kabat's numbering scheme is used.

FIG. 7A, Raji cells, preincubated with a saturated concentration of mL234 (for blocking cell surface antigen ("Ag") sites) or without, were resuspended in PBS containing 1% BSA and 10 μg/ml of purified hL243 and incubated for 1 h at 4° C. After washing, the cells were resuspended in PBS containing 1% BSA and PE-labeled goat anti-human IgG, Fc fragment specific antibody. After further incubation at 4° C. for 30 min, the cells were counted in a Guava PCA. (FIG. 7A) shows specific binding of hL243 to Raji human lymphoma cells (red trace), which was blocked by preincubation of the cells with mL243 (blue trace). (FIG. 7B) is a negative binding control, performed with anti-CEA antibody (hMN-14) in place of hL243 under identical conditions.

FIGS. 8A and 8B illustrate an exemplary Ag-binding affinities comparing hL243γ4P and mL243 in a competitive cell surface binding assay. A constant amount (100,000 cpm, ~10 uCi/ug) of $^{125}$I-labeled mL234 (FIG. 8A) or hL243γ4P (FIG. 8B) was mixed with varying concentrations (0.2-700 nM) of unlabeled hL243γ4P (▲) or mL2343 (■). The mixtures were added to Raji cells and incubated at room temperature for 2 h. The cells were washed to remove unbound antibodies and the radioactivity associated with the cells was counted. hL243γ4P and mL234 were shown to compete with each other for binding to cell surface Ag. In both cases, hL243γ4P appeared to bind to Raji cells more strongly than mL243.

FIG. 16A illustrates anti-proloferative effects of single mAbs and FIG. 16B illustrates anti-proloferative effects of mixtures of MAbs on Namalwa human B-cell lymphomas cells.

FIGS. 20A and 20B illustrate anti-proliferative effects of hL243γ4P on several cell lines disclosed herein. FIG. 20A illustrates MTT studies and FIG. 20B illustrates $^3$H-thymidine uptake assays. Note: In axis label of B. hL243 refers to the γ4P form.

FIGS. 21A and 21B illustrate induction of apoptosis dead cells are represented by clear and apoptotic cells are illustrated in solid. FIG. 21A illustrates measurement of Sub G0 DNA in SU-DHL-6 and Namalwa cells and FIG. 21B illustrates Annexin V/7-ADD at 4 and 24 hours. Cells used had 97% viability prior to treatment.

FIGS. 23A and 23B illustrate a cleaved caspase-3 (FIG. 23A) and P-AKT (FIG. 23B) time course studies in Daudi cells.

DETAILED DESCRIPTION

Figure 7:
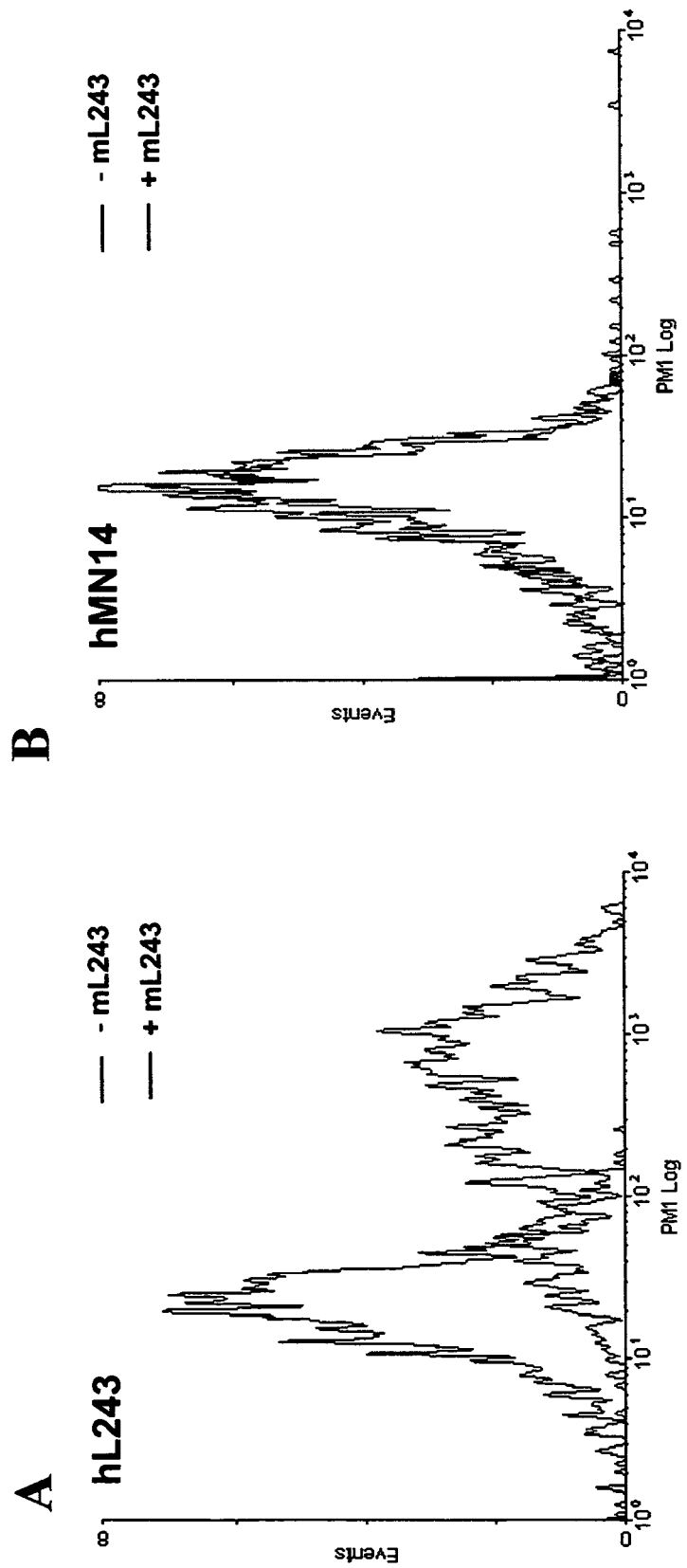
FIGS. 7A and 7B illustrate an exemplary antigen-binding specificity of hL243.

In the following section, several methods are described to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description in order to prevent unnecessary masking of the various embodiments.

In one embodiment of the present invention humanized mouse antibodies are provided that bind to HLA-DR. In one particular embodiment, humanized mL243 antibodies may be provided that bind to HLA-DR but that have reduced immunogenicity compared to the corresponding murine antibodies. In accordance with this embodiment, the antibodies may inhibit proliferation of cells (or induce cell killing) expressing HLA-DR molecules, such as lymphoma cells. Alternatively, antibodies discloses herein may be used to bind to a target molecule and increase the likelihood of cell killing. Pharmaceutical compositions containing the antibodies and methods of treating diseases associated with proliferation of HLA-DR$^+$ cells are provided.

mL243 is a monoclonal antibody previously described by Lampson & Levy (J. Immunol. (1980) 125 293). The amino acid sequences of the light and heavy chain variable regions of the antibody are shown in FIGS. 1 and 2 (also SEQ. ID. 1 and 2 respectively). mL243 has been deposited at the American Type Culture Collection, Rockville, Md., under Accession number ATCC HB55.

In the description that follows, a number of terms may be used and the following definitions are provided to facilitate understanding of the present invention.

Unless otherwise specified, "a" or "an" means "one or more".

As used herein the specification, "subject" or "subjects" may include but are not limited mammals such as humans or mammals for example dogs, cats, ferrets, rabbits, pigs, horses, or cattle.

"Antibody-dependent cell mediated cytotoxicity" or "ADCC" is a cell-mediated reaction in which nonspecific cytotoxic cells that express Fc receptors (natural killer cells, neutrophils, and macrophages) recognize bound antibody on target cells and subsequently cause lysis of the target cells. The primary cells for mediating ADCC are the natural killer cells (express the FcDRIII only) and monocytes (express FcDRI, FcDRII and FcDRIII).

"Complement-dependent cytotoxicity" or "CDC" refers to the lysing of a target in the presence of complement. The complement activation pathway is initiated by the binding of the first component of the complement system (Clq) to a molecule (e.g., an antibody) complexed with a cognate antigen.

The "Fc receptor" or "FcR" is used to describe a receptor that binds to the Fc region of an antibody. Both CDC and ADCC require the Fc portion of a MAb and the effect of ADCC can be augmented by increasing the binding affinity for FcγR (IgG Fc receptors) on effector cells (Shinkawa, et al., *J. Biol. Chem.* 278: 3466-3473, 2003; Shields et al., *J. Biol Chem.* 211: 26733-26740, 2002; Shields et al, *J. Biol. Chem.* 276: 6591-6604, 2002; Davies et al., *Biotechnol. Bioeng.* 74: 288-294,2001; and Umana et al., *Nature Biotechnol.* 176-180, 1999). An "effector cell" refers to any type of cell that is capable of carrying out effector cell function(s). It is well known that effector cells having different specialized immune fictions can be distinguished from one another on the basis of their differential expression of a wide variety of cell surface antigens, such as many of the antigens described herein to which binding domain polypeptides can specifically bind. Effector cells include but are not limited to any cell that is capable of directly mediating an activity which is a component of immune system function, including cells having such capability naturally or as a result of genetic engineering. An effector cell comprises a cell surface receptor for an immunoglobulin, such as a receptor for an immunoglobulin constant region and including the class of receptors commonly referred to as "Fc receptors" (FcR). Cells that are capable of mediating ADCC are examples of effector cells. Other examples include natural killer (NK) cells, tumor-infiltrating T lymphocytes (TIL), cytotoxic T lymphocytes (CTL), and granulocytic cells such as cells that comprise allergic response mechanisms. Effector cells can also affect cells of hematopoietic origins including cells at various stages of differentiation within myeloid and lymphoid lineages and which may (but need not) express one or more types of functional cell surface FcR, such as T lymphocytes, B lymphocytes, NK cells, monocytes, macrophages, dendritic cells, neutrophils, basophils, eosinophils, mast cells, platelets, erythrocytes, and precursors, progenitors (e.g., hematopoietic stem cells), quiescent, activated and mature forms of such cells. Other effector cells may include cells of non-hematopoietic origin that are capable of mediating immune functions, for example, endothelial cells, keratinocytes, fibroblasts, osteoclasts, epithelial cells and other cells. Immune effector cells may also include cells that mediate cytotoxic or cytostatic events, or endocytic, phagocytic, or pinocytotic events, or that effect induction of apoptosis, or that effect microbial immunity or neutralization of microbial infection, or cells that mediate allergic, inflammatory, hypersensitivity and/or autoimmune reactions.

An antibody that "inhibits growth" is one that inhibits the growth of diseased cells in vitro and/or in vivo. By inhibiting the growth of diseased cells, the percentage of cells in S phase is reduced. Preferred percentage of growth inhibition by an antibody of the present invention can be greater than 20%, preferably greater than 50% at an antibody concentration of about 0.5 μg/mL-20 μg/mL in vitro, and at a dose in adult patients of about 0.5 mg/kg-15 mg/kg.

An "antibody" as used herein refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. The term "antibody" also includes "humanized" antibodies and even fully human antibodies that can be produced by phage display, gene and chromosome transfection methods, as well as by other means. This term also includes monoclonal antibodies, polyclonal antibodies, multivalent antibodies, multispecific antibodies (e.g., bispecific antibodies).

An "immunogenic response" or "antigenic response" is one that results in the production of antibodies directed to a compound after the appropriate cells have been contacted therewith. The compound that is used to elicit an immunogenic response is referred to as an immunogen or antigen. The antibodies produced in the immunogenic response specifically bind the immunogen used to elicit the response.

The compound that is used to elicit an immunogenic response is referred to as an immunogen or antigen. An "epitope" or "antigenic determinant" is an area on the surface of an immunogen that stimulates a specific immune response directed to the epitope. In proteins, particularly denatured proteins, an epitope is typically defined and represented by a contiguous amino acid sequence. However, in the case of nondenamred proteins, epitopes also include structures, such as active sites, that are formed by the three-dimensional folding of a protein in a manner such that amino acids from separate portions of the amino acid sequence of the protein are brought into close physical contact with each other.

Naturally occurring (wild type) antibody molecules are Y-shaped molecules consisting of four polypeptide chains, two identical heavy chains and two identical light chains, which are covalently linked together by disulfide bonds. Both types of polypeptide chains have constant regions, which do not vary or vary minimally among antibodies of the same class (i.e., IgA, IgM, etc.), and variable regions. The variable regions are unique to a particular antibody and comprise a recognition element for an epitope. The carboxy-terminal regions of both heavy and light chains are conserved in sequence and are called the constant regions (also known as C-domains). The amino-terminal regions (also known as V-domains) are variable in sequence and are responsible for antibody specificity. The antibody specifically recognizes and binds to an antigen mainly through six short complementarity-determining regions (CDRs) located in their V-domains.

Each light chain of an antibody is associated with one heavy chain, and the two chains are linked by a disulfide bridge formed between cysteine residues in the carboxy-terminal region of each chain, which is distal from the amino terminal region of each chain that constitutes its portion of the antigen binding domain. Antibody molecules are further stabilized by disulfide bridges between the two heavy chains in an area known as the hinge region, at locations nearer the carboxy terminus of the heavy chains than the locations where the disulfide bridges between the heavy and light chains are made. The hinge region also provides flexibility for the antigen-binding portions of an antibody.

The antigen-binding specificity of an antibody can be determined by its variable regions located in the amino terminal regions of the light and heavy chains. The variable regions of a light chain and associated heavy chain form an "antigen binding domain" that recognizes a specific epitope; an antibody thus has two antigen binding domains. The antigen binding domains in a wildtype antibody are directed to the same epitope of an immunogenic protein, and a single wildtype antibody is thus capable of binding two molecules of the immunogenic protein at the same time. Thus, a wildtype antibody is monospecific (i.e., directed to a unique antigen) and divalent (i.e., capable of binding two molecules of antigen).

"Polyclonal antibodies" are generated in an immunogenic response to a protein having many epitopes. A composition (e.g., serum) of polyclonal antibodies thus includes a variety of different antibodies directed to the same and to different epitopes within the protein. Methods for producing polyclonal antibodies are known in the art (see, e.g., Cooper et al., Section III of Chapter 11 in: *Short Protocols in Molecular Biology*, 2nd Ed., Ausubel et al., eds., John Wiley and Sons, New York, 1992, pages 11-37 to 11-41).

"Antipeptide antibodies" (also known as "monospecific antibodies") are generated in a humoral response to a short (typically, 5 to 20 amino acids) immunogenic polypeptide that corresponds to a few (preferably one) isolated epitopes of the protein from which it is derived. A plurality of antipeptide antibodies includes a variety of different antibodies directed to a specific portion of the protein, i.e., to an amino acid sequence that contains at least one, preferably only one, epitope. Methods for producing antipeptide antibodies are known in the art (see, e.g., Cooper et al., Section III of Chapter 11 in: *Short Protocols in Molecular Biology*, 2nd Ed., Ausubel et al., eds., John Wiley and Sons, New York, 1992, pages 11-42 to 11-46).

A "monoclonal antibody" is a specific antibody that recognizes a single specific epitope of an immunogenic protein. In a plurality of a monoclonal antibody, each antibody molecule is identical to the others in the plurality. In order to isolate a monoclonal antibody, a clonal cell line that expresses, displays and/or secretes a particular monoclonal antibody is first identified; this clonal cell line can be used in one method of producing the antibodies of the present invention. Methods for the preparation of clonal cell lines and of monoclonal antibodies expressed thereby are known in the art (see, for example, Fuller et al., Section II of Chapter 11 in: *Short Protocols in Molecular Biology*, 2nd Ed., Ausubel et al., eds., John Wiley and Sons, New York, 1992, pages 11-22 to 11-11-36).

A "naked antibody" is an intact antibody molecule that contains no further modifications such as conjugation with a toxin, or with a chelate for binding to a radionuclide. The Fc portion of the naked antibody can provide effector functions, such as complement fixation and ADCC (antibody dependent cell cytotoxicity), which set mechanisms into action that may result in cell lysis. See, e.g., Markrides, Therapeutic inhibition of the complement system, *Pharmacol. Rev.* 50:59-87, 1998. In one embodiment, the therapeutic action of an antibody may require the effector functions of the Fc region (see, e.g., Golay et al, Biologic response of B lymphoma cells to anti-CD20 monoclonal antibody rituximab in vitro: CD55 and CD59 regulate complement-mediated cell lysis, *Blood* 95: 3900-3908, 2000).

In another embodiment, the Fc portion may not be needed or in some instances desired for a therapeutic treatment of a subject. In accordance with this embodiment, other mechanisms, such as apoptosis, may be invoked. Vaswani and Hamilton, Humanized antibodies as potential therapeutic drugs. *Ann. Allergy Asthma Immunol.* 81: 105-119,1998.

An "antibody fragment" is a portion of an intact antibody such as F(ab')a, F(ab)2, Fab', Fab, Fv, sFv and the like. Regardless of structure, an antibody fragment binds with the same antigen that is recognized by the full-length antibody. For example, an anti-CD20 monoclonal antibody fragment binds with an epitope of CD20. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

Antibody fragments produced by limited proteolysis of wildtype antibodies are called proteolytic antibody fragments. These include, but are not limited to, the following:"F(ab')$_2$ fragments" are released from an antibody by limited exposure of the antibody to a prpteolytic enzyme, e.g., pepsin or ficin. An F(ab')2 fragment comprises two "arms," each of which comprises a variable region that is directed to and specifically binds a common antigen. The two Fab' molecules are joined by interchain disulfide bonds in the hinge regions of the heavy chains; the Fab' molecules may be directed toward the same (bivalent) or different (bispecific) epitopes.

"Fab' fragments" contain a single anti-binding domain including an Fab and an additional portion of the heavy chain through the hinge region.

"Fab'-SH fragments" are typically produced from F(ab')2 fragments, which are held together by disulfide bond(s) between the H chains in an F(ab')2 fragment. Treatment with a mild reducing agent such as, by way of non-limiting example, beta-mercaptoethylamine, breaks the disulfide bond(s), and two Fab' fragments are released from one F(ab')$_2$ fragment. Fab'-SH fragments are monovalent and monospecific.

"Fab fragments" (i.e., an antibody fragment that contains the antigen-binding domain and comprises a light chain and part of a heavy chain bridged by a disulfide bond) are produced by papain digestion of intact antibodies. A convenient method is to use papain immobilized on a resin so that the enzyme can be easily removed and the digestion terminated. Fab fragments do not have the disulfide bond(s) between the H chains present in an F(ab')2 fragment.

"Single-chain antibodies" are one type of antibody fragment. The term single chain antibody is often abbreviated as "scFv" or "sFv." These antibody fragments are produced using molecular genetics and recombinant DNA technology. A single-chain antibody consists of a polypeptide chain that comprises both a VH and a VL domains which interact to form an antigen-binding site. The VH and VL domains are usually linked by a peptide of 10 to 25 amino acid residues.

The term "single-chain antibody" further includes but is not limited to a disulfide-linked Fv (dsFv) in which two single-chain antibodies (each of which may be directed to a different epitope) linked together by a disulfide bond; a bispecific sFv in which two discrete scFvs of different specificity is connected with a peptide linker; a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes).

"Complementary determining region peptides" or "CDR peptides" are another form of an antibody fragment. A CDR peptide (also known as "minimal recognition unit") is a peptide corresponding to a single complementarity-determining region (CDR), and can be prepared by constructing genes encoding the CDR of an antibody of interest. Such genes are prepared, for example, by using the polymerase chain reaction to synthesize the variable region from RNA of antibody-producing cells. See, for example, Larrick et al, *Methods: A Companion to Methods in Enzymology* 2:106, 1991.

In "cysteine-modified antibodies," a cysteine amino acid is inserted or substituted on the surface of antibody by genetic manipulation and used to conjugate the antibody to another molecule via, e.g., a disulfide bridge. Cysteine substitutions or insertions for antibodies have been described (see U.S. Pat. No. 5,219,996). Methods for introducing Cys residues into the constant region of the IgG antibodies for use in site-specific conjugation of antibodies are described by Stimmel et al. (*J. Biol. Chem* 275:330445-30450, 2000).

A "humanized antibody" is a recombinant protein used to reduce the amount of non-human protein in which the CDRs from an antibody from one species; e.g., a rodent antibody, heavy and light variable chains of the rodent antibody are exchanged for some human heavy and light variable domains for example using protein engineering techniques. The constant domains of the antibody molecule are derived from those of a human antibody. See Gussow and Seemann, Humanization of monoclonal antibodies, *Method Enzymol.* 203:99-121, 1991 and Vaswani and Hamilton, *Ann. Allergy Asthma Immunol.* 81:105-119, 1998.

Production of Antibody Fragments

Some embodiments of the claimed methods and/or compositions may concern antibody fragments. Such antibody fragments may be obtained by pepsin or papain digestion of whole antibodies by conventional methods. For example, antibody fragments may be produced by enzymatic cleavage of antibodies with pepsin to provide a 5S fragment denoted $F(ab')_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. Nos. 4,036,945; 4,331,647; Nisonoff et al., 1960, Arch. Biochem. Biophys., 89:230; Porter, 1959, Biochem. J., 73:119; Edelman et al., 1967, Methods in Enzymology, page 422 (Academic Press), and Coligan et al. (eds.), 1991, Current Protocols in Immunology, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as *E. coli*. The recombinant host cells synthesize a single polypeptide chain with a linker peptide bridging the two V domains. Methods for producing sFvs are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, Monoclonal Antibodies:Production, Engineering and Clinical Application, pages 166-179 (Cambridge University Press); Birch et al., (eds.), 1995, Monoclonal Antibodies: Principles and Applications, pages 137-185 (Wiley-Liss, Inc.)

In one embodiment, the humanized antibody may be linked to an effector or reporter molecule. For example, a macrocycle for chelating a heavy metal atom, or a toxin such as ricin, may be attached to the humanized antibody by a covalent bridging structure. Alternatively, the procedure of recombinant DNA technology may be used to produce a humanized antibody molecule in which the Fc fragment, Cu3 or Cn2 domain of a complete antibody molecule has been replaced by or has attached thereto by peptide linkage a functional non-immunoglobulin protein such as an enzyme or toxin molecule.

In another embodiment of the present invention, the humanized antibody may include a complete antibody molecule, having full length heavy and light chains; a fragment thereof, such as a Fab, Fab', F(ab')2, or Fv fragment; a single chain antibody fragment, e.g. a single chain Fv, a light chain or heavy chain monomer or dimer; multivalent monospecific antigen binding proteins comprising two, three, four or more antibodies or fragments thereof bound to each other by a connecting structure; or a fragment or analogue of any of these or any other molecule with the same specificity as MAb mL243. In one particular embodiment, the antibody may include a complete antibody molecule, having full length heavy and light chains.

Humanized L243 Antibodies

Chimeric and Humanized Antibodies

A chimeric antibody is a recombinant protein in which the variable regions of a human antibody have been replaced by the variable regions of, for example, an anti-L243 mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844. )

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990).

In another embodiment, an antibody may be a human monoclonal antibody. Such antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994).

In one embodiment, the humanized antibody may include the CDR region sequences of mL243 within human antibody framework sequences and with human antibody constant region sequences. More particularly, the humanized antibodies may include a heavy chain variable domain (VH) containing the mL243 VH residues at all of CDR1 (31 to 35), CDR2 (50 to 65) and CDR3 (95 to 102). In another embodiment, the CDRs of the light chain variable domain (VL) correspond to mL243 VL residues at all of CDR1 (24 to 34) CDR2 (50 to 56) and CDR3 (89 to 97). In another particular embodiment of the invention, other murine L243 VH residues retained in the humanized design are at one or more of the following positions: F27, K38, K46, A68 and F91. Similarly the murine L243 residues in the VL retained in the humanized design are at one or more of the following positions: R37, K39, V48, F49, and G100.

Further details for humanizing antibody sequences, while retaining the antigenic specificity of the original non-human antibody, are disclosed for example in U.S. patent application Ser. No. 09/988,013 filed Nov. 16, 2001, the entire text of which is incorporated herein by reference In one embodiment, the present invention further provides a CDR-grafted humanized antibody heavy chain having a variable region domain comprising acceptor frameworks derived from a human heavy chain of subgroup I and the antigen binding regions derived from the mL243 donor where the framework comprises mL243 donor residues at one or more of positions F27, K38, K46, A68 and F91. See FIGS. 3 and 4 respectively.

In one embodiment of the present invention a CDR-grafted humanized antibody light chain may be provided having a variable region domain comprising acceptor frameworks derived from a human kappa light chain of subgroup I and mL243 donor antigen binding regions where the framework comprises mL243 donor residues at one or more of positions R37, K39, V48, F49, and G100.

In the CDR-grafted humanized antibody molecule of embodiments of the present invention, the remaining non-L243 immunoglobulin derived (acceptor) portions may be derived from any suitable human immunoglobulin, provided that the humanized antibody can fold such that it retains the ability to specifically bind HLA-DR. Preferably the type of human framework (FR) used is of the same/similar class/type as the donor antibody.

In one embodiment of the invention, the human frameworks may be chosen to maximize homology with a donor antibody sequence particularly at positions spatially close or adjacent to the CDRs. In accordance with this embodiment, the frameworks (i.e., FR1-4) of the humanized L243 VH or VL may be derived from a combination of human antibodies. Examples of human frameworks which may be used to construct CDR-grafted antibodies are LAY, POM, TUR, TEI, KOL, NEWM, REI, RF and EU; preferably human RF-TS3 FRI-3 and NEWM FR4 are used for the heavy chain and REI FR1-4 is used for the light chain. The V domain residue numbering system used herein is described in Kabat et al, (1991), Sequences of Proteins of Immunological Interest, 5th Edition, United States Department of Health and Human Services. See FIG. 5 for a comparative ammo acid sequence alignment of human RF-TS3 (FR 1-3 and NEWM FR4), mL243, and hL243 VH chain. See FIG. 6 for a comparative amino acid sequence alignment of human REI, mL243, and hL243 VL chain.

The light and heavy chain variable domains of the humanized antibody molecule may be fused to human light or heavy chain constant domains as appropriate-(the term "heavy chain constant domains include hinge regions unless specified otherwise). The human constant domains of the humanized antibody molecule, where present, may be selected with regard to the proposed function of the antibody. In one embodiment, the human constant domains may be selected based on the lack of effector functions. The heavy chain constant domains fused to the heavy chain variable region may be those of human IgA (a1 or a2 chain), IgG (71,72, j3>, or y4 chain) or IgM (u chain). Preferably a human y chain is used. The light chain constant domains which may be fused to the light chain variable region include human lambda and kappa chains.

In one particular embodiment of the present invention, a yl chain is used. In yet another particular embodiment of the present invention, a γ4 chain is used. The use of the y4 chain may be in some cases may increase the tolerance of an hL243 in subjects (decreased side effects and infusion reactions, greater tolerance, etc.).

In one embodiment, analogues of human constant domains may be used. These include but are not limited to those constant domains containing one or more additional amino acids than the corresponding human domain or those constant domains wherein one or more existing amino acids of the corresponding human domain has been deleted or altered. Such domains may be obtained, for example, by oligonucleotide directed mutagenesis.

As used herein, the term altered when used in conjunction with the ability of an antibody to fix complement indicates a decrease in the ability of antibody to fix complement compared to the starting unaltered antibody. Altering an appropriate amino acid alters the ability of an antibody to fix complement. As used herein the phrase 'substantially' reduce complement fixation denotes that human complement fixation is preferably less than or equal to 30%, more preferably less than or equal to 20%, and is most preferably less than or equal to 10% of the level seen with wild type antibody.

Altered complement fixing ability may be produced by techniques that are well known in the art, for example, deleting residues, inserting a glycosylation site at a suitable position in the molecule, or exchanging lower hinge regions of antibodies of different isotypes.

Preparation of Genes Encoding HL243 Antibodies

Any standard technique of molecular biology known in the art may be used to prepare DNA sequences coding for the antibodies according to the present invention. For example, DNA sequences may be synthesised completely or in part using oligonucleotide synthesis techniques. Site-directed mutagenesis and polymerase chain reaction (PCR) techniques may be used as appropriate. Suitable processes include the PCR strand overlap procedure and PCR mutagenesis as described in for example "PCR Technology Principles and Applications for DNA Amplification" (1989), Ed. H. A. Erlich, Stockholm Press, N.Y., London, and oligonucleotide directed mutagenesis (Kramer et al, Nucleic. Acid. Res. 12 9441 (1984)).

Any standard techniques of molecular biology may also be used to prepare DNA sequences coding for CDR-grafted products. For example, DNA sequences may be synthesized completely or in part using oligonucleotide synthesis techniques. Site-directed mutagenesis and polymerase chain reaction (PCR) techniques may be used as appropriate. Oligonucleotide directed synthesis (Jones et al (1986) Nature 321 522-525) and oligonucleotide directed mutagenesis of a pre-existing variable domain region (Verhoeyen et al (1988) Science 23 1534-1536) may be used. Enzymatic filling-in of gapped oligonucleotides using T4 DNA polymerase (Queen et al (1989) Proc. Natl. Acad. Sci. USA 86 10029-10033) may also be used. Any suitable host cell/expression vector system may be used for expression of the DNA sequences coding for the chimeric or CDR-grafted heavy and light chains. A "recombinant host" may be any prokaryotic or eukaryotic cell that contains either a cloning vector or expression vector. This term also includes those prokaryotic or eukaryotic cells, as well as transgenic animals, that have been genetically engineered to contain the cloned gene(s) in the chromosome or genome of the host cell or cells. Bacteria, e.g. *E. coli*, and other microbial systems may be used advantageously in particular for expression of antibody fragments, e.g., Fv, Fab and Fab' fragments and single chain antibody fragments, e.g. single chain Fvs. Eukaryotic hosts, e.g. mammalian cell expression systems, may also be used to obtain antibodies according to the present invention, particularly for production of larger chimeric or CDR-grafted antibody products. Suitable mammalian host cells include myeloma cells, such as Sp2/0 and NSO cells, as well as Chinese Hamster Ovary (CHO) cells, hybridoma cell lines, and other mammalian cells useful for expressing antibodies.

An "expression vector" as used herein is a DNA molecule including the genes of interest that are expressed in a host cell.

Typically, gene expression is placed under the control of certain regulatory elements, including constitutive or inducible promoters, tissue-specific regulatory elements and enhancers. Such a gene is said to be "operably linked to" the regulatory elements. In further aspects, on embodiment also includes DNA sequences coding for the heavy and light chains of the antibodies of the present invention, cloning and expression vectors containing these DNA sequences, host cells transformed with these DNA sequences and processes for producing the heavy or light chains and antibody molecules comprising expressing these DNA sequences in a transformed host cell.

DNA coding for human immunoglobulin sequences may be obtained by any means known in the art. For example, amino acid sequences of preferred human acceptor frameworks, such as -LAY, POM, KOL, REI, EU, TUR, TEI, RF and NEWM, are widely available. Similarly, the consensus sequences for human light and heavy chain subgroups also available. The skilled artisan is aware that multiple codon sequences may encode the same amino acid and that in various embodiments, the disclosed nucleic acid sequences may be substituted with an alternative sequence that encodes the same sequence of amino acids. The skilled artisan is also aware that, depending on the species of origin for a cell line used to express a protein from a nucleic acid sequence, the codon usage may be optimized to enhance expression in the selected species. Such species preferred codon frequencies are well known in the art.

In one embodiment, the antibody disclosed herein may be a complete antibody, or as explained above, a fragment thereof, a monomer or dimer or a multivalent monospecific antigen binding protein. Thus, further to one aspect of the present invention, a multivalent monospecific antigen binding protein may be provided comprising two, three, four or more antibodies fragments thereof bound to each other by a connecting structure, which protein is not a natural immunoglobulin, each of said antibodies or fragments having a specificity for the epitope recognized by murine MAb L243, said antigen binding protein being optionally conjugated with an effector or reporter molecule.

In accordance with these embodiments, each antibody or fragment may be a humanized antibody or a fragment thereof, as defined above, and a multivalent monospecific antigen binding protein may be a humanized multivalent monospecific antigen binding protein. Non-humanized, e.g., murine, multivalent monospecific antigen binding proteins, however, may be contemplated and an embodiment may extend to these where applicable.

In one particular embodiment, a multivalent antigen binding protein may provide two, three or four antibodies or fragments thereof bound to each other by a connecting structure. In a another embodiment, a process for producing the humanized antibody may include: i) producing in an expression vector a DNA sequence which encodes an antibody heavy or light chain including a variable domain wherein at least one of the CDRs of the variable domain may be derived from the mL243 MAb and the remaining unmunoglobulin-derived parts of the antibody chain are derived from a human immunoglobulin; ii) producing in an expression vector a DNA sequence which encodes a complementary antibody light or heavy chain including a variable domain, wherein at least one of the CDRs of the variable domain is derived from the MAb mL243 and the remaining immunoglobulin-derived parts of the antibody chain may be derived from a human immunoglobulin; iii) transfecting a host cell with the aforementioned DNA sequences; and iv) culturing the transfected cell line to produce the humanized antibody molecule.

Production of Recombinant hL243 in a Host Cell

In one embodiment, a host cell line used to produce recombinant hL243 may be transfected with two vectors, the first vector containing the DNA sequence encoding the light chain-derived polypeptide, and the second vector containing the DNA sequence encoding the heavy chain derived polypeptide. Preferably the vectors are identical except in so far as the coding sequences and selectable markers are concerned, so as to ensure as far as possible that each polypeptide chain is equally expressed. Transfection may be conducted by any technique known to those skilled in the art. See for example Maniatis et al (1982) (Molecular Cloning, Cold Spring Harbor, N.Y.) and Primrose and Old (1980) (Principles of Gene Manipulation, Blackwell, Oxford). One particular technique for transfection may be electroporation. Other examples include calcium phosphate mediated transfection, cationic-lipid mediated transfection, and the like. In one alternative embodiment, a single vector may be used, the vector including the DNA sequences encoding both light chain- and heavy chain-derived polypeptides, and a selectable marker.

General Methods for the Production of Recombinant Fusion Proteins Containing Antibody Fragments Nucleic acid sequences encoding antibody fragments that recognize specific epitopes can be obtained by techniques that are well known in the art. For example, hybridomas secreting antibodies of a desired specificity can be used to obtain antibody-encoding DNA that can be prepared using known techniques, for example, by PCR or by traditional cDNA cloning techniques. Alternatively, Fab' expression libraries or antibody phage display libraries can be constructed to screen for antibody fragments having a desired specificity.

The nucleic acid encoding the antibody fragment can then be ligated, directly or via a sequence that encodes a peptide spacer, to nucleic acid encoding either the DDD or the AD. Methods of producing nucleic acid sequences encoding these types of fusion proteins are well known in the art and are further discussed in the following Examples.

In another embodiment, additional amino acid residues may be added to either the N- or C-terminus of the modular subunit composed of A/DDD or B/AD, where the exact fusion site may depend on whether the DDD or the AD are attached to the N- or C-terminus (or at an internal position). The additional amino acid residues may comprise a peptide tag, a signal peptide, a cytokine, an enzyme (for example, a pro-drug activating enzyme), a hormone, a toxin, a peptide drug, a membrane-interacting peptide, or other functional proteins.

Proteins or peptides may be synthesized, in whole or in part, in solution or on a solid support in accordance with conventional techniques. Various automatic synthesizers are commercially available and can be used in accordance with known protocols. See, for example, Stewart and Young, (1984, *Solid Phase Peptide Synthesis*, 2d. ed., Pierce Chemical Co.); Tam et al., (1983, *J. Am. Chem. Soc.*, 105:6442); Merrifield, (1986, *Science,* 232: 341-347); and Barany and Merrifield (1979, *The Peptides*, Gross and Meienhofer, eds., Academic Press, New York, pp. 1-284). Short peptide sequences, usually from about 6 up to about 35 to 50 amino acids, can be readily synthesized by such methods. Alternatively, recombinant DNA technology may be employed wherein a nucleotide sequence which encodes a peptide of interest is inserted into an expression vector, transformed or transfected into an appropriate host cell, and cultivated under conditions suitable for expression.

Methods for producing recombinant proteins in a desired host cell are well known in the art. To facilitate purification, the stably tethered structures may contain suitable peptide tags, such as the FLAG sequence or the poly-HIS sequence, to facilitate their purification with a relevant affinity column.

In one embodiment, the Fv fragments may include $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as *E. coli*. The recombinant host cells synthesize a single polypeptide chain with a linker peptide bridging the two V domains. Methods for producing sFvs are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, Monoclonal Antibodies: Production, Engineering and Clinical Application, pages 166-179 (Cambridge University Press); Birch et al., (eds.), 1995, Monoclonal Antibodies Principles and Applications, pages 137-185 (Wiley-Liss, Inc.)

Suitable host cells or cell lines for the expression of the constituent subunits of the stably tethered structures of are known to one skilled in the art. The use of a human host cell would enable any expressed molecules to be modified with human glycosylation patterns. However, there is no indication that a human host cell is essential or preferred for the disclosed methods Bi-Specific Antibodies and Conjugates In certain embodiments, the L243 ligands disclosed herein may be used in combination with another molecule attached to the ligand. Attachment may be either covalent or non-covalent. In some embodiments, a L243 ligand may be attached to a bi-specific antibody, i.e., an antibody that has two different binding sites, one for the L243 ligand and another for a disease-related target antigen. Any disease or condition relating to angiogenesis, cancer, metastasis or cell motility may be targeted, including but not limited to, primary cancer, metastatic cancer, hyperplasia, rheumatoid arthritis, inflammatory bowel disease, Crohn's disease, ulcerative colitis, sarcoidosis, asthma, edema, pulmonary hypertension, formation and development of tumor tissue, psoriasis, diabetic retinopathy, macular degeneration, corneal graft rejection, neovascular glaucoma, myocardial angiogenesis, plaque neovascularization, restenosis, neointima formation after vascular trauma, telangiectasia, hemophiliac joints, angiofibroma, fibrosis associated with chronic inflammation, lung fibrosis, deep venous thrombosis and wound granulation. Methods for construction and use of bi-specific and multispecific antibodies are disclosed, for example, in U.S. Patent Application Publication No. 20050002945, filed Feb. 11, 2004, the entire text of which is incorporated herein by reference.

Where the bi-specific antibody is targeted in part against a tumor-associated antigen, it is anticipated that any type of tumor and any type of tumor antigen may be so targeted. Exemplary types of tumors that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid, non-Hodgkin's lymphoma, ovarian cancer, pancreatic cancer, glioma, melanoma, liver cancer, prostate cancer, and urinary bladder cancer. Preferred are tumors that have constitutive expression of L243, or which can be stimulated to produce L243.

A variety of recombinant methods can be used to produce bi-specific antibodies and antibody fragments. For example, bi-specific antibodies and antibody fragments can be produced in the milk of transgenic livestock. (See, e.g., Colman, A., Biochem. Soc. Symp., 63: 141-147, 1998; U.S. Pat. No. 5,827,690, each incorporated herein by reference.) Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow alpha-lactoglobulin gene, the sheep beta-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

Pre-Targeting

One strategy for use of bi-specific antibodies includes pre-targeting methodologies, in which an effector molecule, such as an anti-angiogenic or anti-tumor ligand, is administered to a subject after a bi-specific antibody has been administered. The bi-specific antibody, which would include a binding site for an L243 ligand and one for the diseased tissue, localizes to the diseased tissue and increases the specificity of localization of the effector L243 ligand to the diseased tissue (U.S. Patent Application No. 20050002945). Because the effector molecule may be cleared from circulation much more rapidly than the bi-specific antibody, normal tissues may have a decreased exposure to the effector molecule when a pretargeting strategy is used than when the effector molecule is directly linked to the disease targeting antibody. Pretargeting methods have been developed to increase the target:background ratios of detection or therapeutic agents. Examples of pre-targeting and biotin/avidin approaches are described, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077,499; 09/597,580; 10/361,026; 09/337,756; 09/823,746; 10/116,116; 09/382,186; 10/150,654; 6,090,381; 6,472,511; 10/114,315; U.S. Provisional Application No. 60/386,411; U.S. Provisional Application No. 60/345,641; U.S. Provisional Application No. 60/3328,835; U.S. Provisional Application No. 60/426,379; U.S. Ser. Nos. 09/823,746; 09/337,756; and U.S. Provisional Application No. 60/342,103, all of which are incorporated herein by reference.

In certain embodiments, bispecific antibodies and targetable constructs may be of use in treating and/or imaging normal or diseased tissue and organs, for example using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference. Additional methods are described in U.S. application Ser. No. 09/337,756 filed Jun. 22, 1999 and in U.S. application Ser. No. 09/823,746, filed Apr. 3, 2000.

Therapeutic and Diagnostic Uses of hL243

In another embodiment, the present invention also provides therapeutic and diagnostic compositions containing the antibodies of embodiments of the invention. Such compositions can include an antibody according to the invention together with a pharmaceutically acceptable excipient, diluent or carrier, e.g., for in vivo use.

A "therapeutic agent" is a molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, enzymes, nucleases, hormones, immunomodulators, oligonucleotides, interference RNA, chelators, boron compounds, photoactive agents or dyes and radioisotopes.

A "diagnostic/detection agent" is a molecule or atom which is administered linked to or conjugated to an antibody moiety, i.e., antibody or antibody fragment, or subfragment, and is useful in diagnosing or detecting a disease by locating the cells containing the antigen. Useful diagnostic/detection agents include, but are not limited to, radioisotopes, dyes (such as with the biotin-streptavidin complex), contrast agents, fluorescent compounds or molecules and enhancing agents (e.g. paramagnetic ions) for magnetic resonance imaging (MRI), and particles or liposomes as examples of agents used for ultrasound imaging. Ultrasound enhancing agents are disclosed in United States Patent Applications US20040219203A1 and US20050014207A1, and, are thus, incorporated in their entirety by reference. Preferred are gas-filled liposomes. See Maresca, G. et al., *Eur J. Radiol. Suppl* 2 S171-178 (1998); Demos, Sm. Et al. *J. Drug Target* 5 507-518 (1998); and Unger, E. et al., *Am J. Cardiol.* 81 58G-61G (1998). Alternatively, a bispecific antibody may be used to target the liposome. In one such embodiment, the liposome is a gas-filled liposome with a bivalent DTPA-peptide covalently attached to the outside surface of the liposome lipid membrane. United States Patent Application US20040018557A1 discloses such liposomes, and is incorporated in its entirety by reference.

U.S. Pat. No. 6,331,175 describes MRI technique and the preparation of antibodies conjugated to a MRI enhancing agent and is incorporated in its entirety by reference. In one particular method, diagnostic/detection agents may be selected from the group consisting of radioisotopes, enhancing agents for use in magnetic resonance imaging, ultrasound agents, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates can be coupled to the antibodies using standard chemistries. The chelate may be linked to the antibody by a group which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659 to Hawthorne, entitled "Antibody Conjugates", issued Apr. 25, 1989, the disclosure of which is incorporated herein in its entirety by reference. In a another particular embodiment, useful metal-chelate combinations may include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$CU, $^{M}$Cu, $^{18}$F, $^{m}$In, $^{67}$Ga; $^{68}$Ga, $^{""""}$Tc, $^{94m}$Tc, $^{H}$C, $^{13}$N, $^{15}$O, $^{76}$Br, $^{97}$Zr, for radio-imaging. The same chelates, when complexed with non-radioactive metals, such as manganese, iron and gadolinium may be useful for MRI, when used along with any antibodies disclosed herein. Macrocyclic chelates such as NOTA, DOT A, and TETA are of use with a variety of metals and radiometals, most particularly with radionuclides of gallium, yttrium and copper, respectively. Such metal-chelate complexes can be stabilized by tailoring the ring size to the metal of interest. Other ring-type chelates such as macrocyclic polyethers, which are of interest for stably binding nuclides, such as $^{223}$Ra for RAIT, are encompassed by embodiments herein.

Examples of therapeutic agents include but are not limited to antibodies, antibody fragments, drugs, including chemotherapeutic agents, toxins, enzymes, enzyme-inhibitors, nucleases, hormones, hormone antagonists, immunomodulators, cytokines, chelators, boron compounds, uranium atoms, photoactive agents and radionuclides.

Useful diagnostic/detection agents include, but are not limited to, radioisotopes, dyes (such as with the biotin-streptavidin complex), radiopaque materials (e.g., iodine, barium, gallium, and thallium compounds and the like), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic/detection agents are selected from the group consisting of radioisotopes for nuclear imaging, intraoperative and endoscopic detection; enhancing agents for use in magnetic resonance imaging or in ultrasonography; radiopaque and contrast agents for X-rays and computed tomography; and fluorescent compounds for fluoroscopy, including endoscopic fluoroscopy.

Chemotherapeutic agents, for the purpose of this disclosure, include all known chemotherapeutic agents. Known chemotherapeutic agents include but are not limited to the taxanes, nitrogen mustards, ethylenimine derivatives, alkyl sulfonates, nitrosoureas, triazenes, folic acid analogs, pyrimidine analogs, purine analogs, antisense oligonucleotides, antagonists or inhibitors of transcription factors, interference RNAs, alkaloids, antibiotics, enzymes, platinum coordination complexes, COX-2 inhibitors, apoptotic agents, substituted urea, methyl hydrazine derivatives, adrenocortical suppressants, or antagonists. In a more particular embodiment, the chemotherapeutic agents may include steroids, progestins, estrogens, antiestrogens, or androgens. In another particular embodiment, the chemotherapy agents may include actinomycin, azaribine, anastrozole, azacytidine, bleomycin, bryostatin-1, busulfan, carmustine, Celebrex, chlorambucil, cisplatin, irinotecan (CPT-11), carboplatin, cladribine, cyclophosphamide, cytarabine, dacarbazine, docetaxel, dacarbazine, dactinomycin, daunorubicin, dexamethasone, diethylstilbestrol, doxorubicin, ethinyl estradiol, estramustine, etoposide, floxuridine, fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, methotrexate, mitoxantrone, mithramycin, mitomycin, mitotane, oxaliplatin, phenyl butyrate, prednisone, procarbazine, paclitaxel, pentostatin, semustine streptozocin, SN-38, tamoxifen, taxanes, taxol, testosterone propionate, thalidomide, thioguanine, thiotepa, teniposide, topotecan, uracil mustard, vinblastine, vinorelbine or vincristine.

Some suitable chemotherapeutic agents are described in Remington's Pharmaceutical Sciences 19th Ed. (Mack Publishing Co. 1995). Other suitable chemotherapeutic agents, such as experimental drugs, are known to those of skill in the art.

In one embodiment of the present invention, a toxin may include but is not limited to ricin, abrin, ribonuclease, DNase I, Staphylococcal enterotoxin-A, pokeweed antiviral protein, gelonin, diphtherin toxin, *Pseudomonas* exotoxin, or *Pseudomonas* endotoxin.

In one embodiment of the present invention, enzymes are also useful therapeutic agents and may be selected from the group including but not limited to malate dehydrogenase, Staphylococcal nuclease, delta-V-steroid isomerase, yeast alcohol dehydrogenase, a-glycerophosphate dehydrogenase, triose phosphate isomerase, horseradish peroxidase, alkaline phosphatase, asparaginase, glucose oxidase, p-galactosidase, ribonuclease, urease, catalase, glucose-6-phosphate dehydrogenase, glucoamylase and acetylcholinesterase.

As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18 and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor", and erythropoietin and thrombopoietin. Examples of suitable immunomodulator moieties include IL-2, IL-6, IL-10, IL-12, IL-18, IL-21, interferon-γ, TNF-α, and the like. Alternatively, subjects can receive invention compositions and a separately administered cytokine, which can be administered before, concurrently or after administration of compositions disclosed herein. Embodiments of the present invention may include compositions conjugated to a immunomodulator.

A cytokine, for the purposes of this disclosure, include any cytokines including but not limited to IL-1, IL-2, IL-3, IL-6, IL-10, IL-12, IL-18, IL-21, interferon-α, interferon-β, and interferon-γ. It may also be a colony stimulating factor, such as GM-CSF, G-CSF, erythropoietin, thrombopoietin, and the like.

Additionally, a chelator may include but is not limited to DTPA, DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody composite. It is contemplated herein that fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), Photodynamic Therapy of Tumors and Other Diseases (Libreria Progetto, 1985); van den Bergh, *Chem. Britain* 22:430, 1986). Moreover, it is contemplated that monoclonal antibodies coupled with photoactivated dyes for achieving phototherapy may be used for diagnostic or therapeutic purposes herein. Mewe/a/., *J. Immunol.* 130: 1473, 1983; *idem., Cancer Res.* 45: 4380, 1985; Oseroff et al., *Proc. Natl. Acad. Sci. USA* 83: 8744, 1986; *idem., Photochem. Photobiol.* 46: 83,1987; Hasan et al., *Prog. Clin. Biol. Res.* 288: 471, 1989; Tatsuta et al., *Lasers Surg. Med.* 9: 422, 1989; Pelegrin et al., *Cancer* 67: 2529,1991. However, these earlier studies did not include use of endoscopic therapy applications, especially with the use of antibody fragments or subfragments. Thus, contemplated herein in one embodiment is the therapeutic use of immunoconjugates comprising photoactive agents or dyes. Thus, the present therapeutic methods may include the therapeutic use of immunoconjugates comprising photoactive agents or dyes. Endoscopic methods of detection and therapy are described in U.S. Pat. Nos. 4,932,412; 5,525,338; 5,716,595; 5,736,119; 5,922,302; 6,096,289; and 6,387,350, which are incorporated herein by reference in their entirety.

In one embodiment of the present invention, a nuclide may be used. In one particular embodiment radionuclides that have useful diagnostic or therapeutic properties, such as indium-111 or yttrium-90, respectively are contemplated herein. Other useful nuclides include, but are not limited to, F-18, P-32, Sc-47, Cu-62, Cu-64, Cu-67, Ga-67, Ga-68, Y-86, Y-90, Zr-89, Tc-99m, Pd-109, Ag-111, In-111, I-123, I-125, I-131, Sm-153, Gd-155, Gd-157, Th-161, Lu-177, Re-186, Re-188, Pt-197, Pb-212, Bi-212, Bi-213, Ra-223, Ac-225, As-72, As-77, At-211, Au-198, Au-199, Bi-212, Br-75, Br-76B, C-11, Co-55Co, Dy-166, Er-169, F-18, Fe-52, Fe-59, Ga-67, Ga-68, Gd-154-158, Ho-166, I-120, I-121, I-124, In-110, In-111, M194, Lu-177, Mn-51, Mn-52, Mo-99, N-13, O-15, P-32, P-33, Pb-211, Pb-212, Pd-109, Pm-149, Pr-142, Pr-143, Rb-82, Re-189, Rh-105, Sc-47, Se-75, Sr-83, Sr-89, Th-161, Tc-94, Tc-99, Y-86, Y-90 or Zr-89. For example, suitable diagnostic radionuclides include but are not limited to In-110, In-111, Lu-177, F-18, Fe-52, Cu-62, Cu-64, Cu-67, Ga-67, Ga-68, Y-86, Zr-89, Tc-94m, Tc-94, Tc-99m, I-120, I-123, I-124, I-125, I-131, Gd-154-158, P-32, C-11, N-13, O-15, Re-186, Re-188, Mn-51, Mn-52m, Co-55, As-72, Br-75, Br-76, Rb-82m, Zr-89 and Sr-83. A typical diagnostic radionuclide emits particles and/or positrons having between 25-10,000 keV.

Additionally, suitable therapeutic radionuclides include, but are not limited to In-111, Lu-177, Bi-212, Bi-213, At-211, Cu-62, Cu-64, Cu-67, Y-90, I-125, I-131, P-32, P-33, Sc-47, Ag-111, Ga-67, Pr-142, Sm-153, Th-161, Dy-166, Ho-166, Re-186, Re-188, Re-189, Pb-212, Ra-223, Ac-225, Fe-59, Se-75, As-77, Sr-89, Mo-99, Rh-105, Pd-109, Pr-143, Pm-149, Er-169, Ir-194, Au-198, Au-199, Ac-225 and Pb-211. A typical therapeutic cation emits particles and/or positrons having between 20-10,000 keV.

Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119,1-125, Ho-161, Os-189m and Ir-192. Decay energies of useful Auger-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are referably 2,000-10,000 keV, more preferably 3,000-8,000 keV, and most preferably 4,000-7,000 keV.

Other useful therapeutic agents include metals, such as those as part of a photodynamic therapy, and nuclides, such as those valuable in therapies based on neutron capture procedures. Specifically, zinc, aluminum, gallium, lutetium and palladium are useful for photodynamic therapy and B-10, Gd-157 and U-235 are useful for neutron capture therapy.

In one embodiment, metals may be used as diagnostic agents, including those for magnetic resonance imaging techniques. These metals include, but are not limited to: Gadolinium, manganese, iron, chromium, copper, cobalt, nickel, dysprosium, rhenium, europium, terbium, holmium and neodymium. In order to load an antibody component with radioactive metals or paramagnetic ions, it may be necessary to react it with a reagent having a long tail to which are attached a multiplicity of chelating groups for binding the ions. For example such a tail may be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. In addition, chelates may be coupled to the peptide antigens using standard chemistries. The chelate can be linked to the antibody by a group which enables formation of a bond to the molecule with minimal loss of immunoreactivity and minimal aggregation and/or internal cross-linking. Other, methods and reagents for conjugating chelates to antibodies are disclosed in U.S. Pat. No. 4,824,659 to Hawthorne, entitled "Antibody Conjugates," issued Apr. 25, 1989, the disclosure of which is incorporated herein in its entirety by reference. In one particular embodiment, useful metal-chelate combinations may include but are not limited to 2-benzyl-DTPA and its monomethyl and cyclohexyl analogs, used with diagnostic isotopes in the general energy range of 20 to 2,000 keV. The same chelates, when complexed with non-radioactive metals, such as manganese, iron and gadolinium, are useful for MRI, when used along with the antibodies of embodiments disclosed herein. Macrocyclic chelates such as NOTA, DOTA, and TETA may be of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed by embodiments herein.

In one embodiment of the invention, therapeutically useful immunoconjugates may be obtained by conjugating photoactive agents or dyes to an antibody composite. Fluorescent and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al., eds., *Photodynamic Therapy of Tumors and Other Diseases* (Libreria Progetto 1985); van den Bergh, *Chem, Britain* 22: 430,1986). Moreover, monoclonal antibodies have been coupled with photoactivated dyes for achieving phototherapy. Mew et al., *J. Immunol.* 130: 1473, 1983; idem., *Cancer Res.* 45: 4380, 1985; Oseroff et al., *Proc. Natl Acad. Sci. USA* 83: 8744, 1986; idem., *Photochem. Photobiol* 46:83, 1987; Hasan et al., *Prog, Clin. Biol. Res.* 288: 471, 1989; Tatsuta et al., *Lasers Surg. Med.* 9: 422, 1989; Pelegrin et al, *Cancer* 67: 2529, 1991. However, these earlier studies did not include use of endoscopic therapy applications, especially with the use of antibody fragments or subfragments. Thus, in one embodiment of the present invention contemplates the therapeutic use of immunoconjugates comprising photoactive agents or dyes.

Paramagnetic ions suitable for use in embodiments of the present invention include but are not limited to chromium (III), manganese(II), iron(III), iron(II), cobalt(II), nickel(II), copper(II), neodymium(HI), samarium(III), ytterbium(III), gadolinium(III), vanadium(II), terbium(III), dysprosium (III), holmium(III) and erbium(III), with gadolinium being particularly preferred.

Ions useful in other contexts, such as X-ray imaging, include but are not limited to lanthanum(III), gold(III), lead (II), and especially bismuth(III). Fluorescent labels include rhodamine, fluorescein and renographin. Rhodamine and fluorescein are often linked via an isothiocyanate intermediate. Radiopaque and contrast materials are used for enhancing X-rays and computed tomography, and include iodine compounds, barium compounds, gallium compounds, thallium compounds, etc. Specific compounds include barium, diatrizoate, ethiodized oil, gallium citrate, iocarmic acid, iocetamic acid, iodamide, iodiparmde, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride. Thus, in another embodiment, a therapeutic, pharmaceutical or diagnostic composition comprising an antibody disclosed herein, in combination with a pharmaceutically acceptable excipient, diluent or carrier may be provided.

In another embodiment of the present invention, a process for the preparation of a therapeutic, pharmaceutical or diagnostic composition comprising admixing an antibody disclosed herein together with a pharmaceutically acceptable excipient, diluent or carrier may be provided.

The antibodies and compositions may be for administration in any appropriate form and amount according to the therapy in which they are employed.

In one embodiment, the therapeutic, pharmaceutical or diagnostic composition may take any suitable form for administration, and, preferably is in a form suitable for parenteral administration, e.g. by injection or infusion, for example by bolus injection or continuous infusion. Where the product is for injection of infusion, it may take the form of a suspension, solution or emulsion in an oily or aqueous vehicle and it may contain formulatory agents such as suspending, preservative, stabilising and/or dispersing agents. Alternatively, the antibody or composition may be in dry form, for reconstitution before use with an appropriate sterile liquid.

I is contemplated herein that therapeutic and diagnostic uses may comprise administering an effective amount of an antibody according to embodiments disclosed herein to a human subject. The exact dose to be administered will vary according to the use of the antibody and on the age, sex and condition of the patient but may typically be varied from about 0.1 mg to 1000 mg, for example from about 1 mg to 500 mg. The antibody may be administered as a single dose or in a continuous manner over a period of time. Doses may be repeated as appropriate.

In one example, the antibodies and compositions disclosed herein may be used for administration in any appropriate form and amount according to the therapy in which they are employed. The dose at which the antibody is administered depends on the nature of the condition to be treated and on whether the antibody is being used prophylactically or to treat an existing condition. The dose will also be selected according to the age and conditions of the patient. A therapeutic dose of the antibodies accordingly may be, for example, between preferably 0.1-25 mg/kg body weight per single therapeutic dose and most preferably between 0.1-10 mg/kg body weight for single therapeutic dose.

In one embodiment, any antibody disclosed herein may be formulated in accordance with conventional practice for administration by any suitable route and may generally be in a liquid form (e.g., a solution of the antibody in a sterile physiologically acceptable buffer) for administration by, for example, an intravenous, intraperitoneal, subcutaneous, or intramuscular route.

An "immunoconjugate" contemplated herein is an antibody, fusion protein, or fragment thereof conjugated to at least one therapeutic and/or diagnostic/detection agent. The diagnostic/detection agent may include a radionuclide or non-radionuclide, a contrast agent (such as for magnetic resonance imaging, computed tomography or ultrasound), and the radionuclide can be a gamma-, beta-, alpha-, Auger electron-, or positron-emitting isotope.

As used herein, the term "antibody fusion protein" is a recombinantly produced antigen-binding molecule in which two or more of the same or different natural antibody, single-chain antibody or antibody fragment segments with the same or different specificities are linked. Valency of the fusion protein indicates the total number of binding arms or sites the fusion protein has to an antigen or epitope; i.e., monovalent, bivalent, trivalent or multivalent. The multi valency of the antibody fusion protein means that it can take advantage of multiple interactions in binding to an antigen, thus increasing the avidity of binding to the antigen. Specificity indicates how many different antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one antigen. Monospecific, multivalent fusion proteins have more than one binding site for an epitope but only bind with the same epitope on the same antigen, for example a diabody with two binding sites reactive with the same antigen. The fusion protein may include a multivalent or multispecific combination of different antibody components or multiple copies of the same antibody component. The fusion protein may additionally include a therapeutic gent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

In another embodiment, selective linkage may be achieved by using a heterobifunctional linker such as maleimide-hydroxysuccinimide ester. Reaction of the ester with an antibody or fragment can derivatize amine groups on the antibody or fragment, and the derivative can then be reacted with, e.g., an antibody Fab fragment having free sulfhydryl groups (or, a larger fragment or intact antibody with sulthydryl groups appended thereto by, e.g., Traut's Reagent). Such a linker is less likely to crosslink groups in the same antibody and improves the selectivity of the linkage.

In one particular embodiment, antibodies or fragments disclosed herein may be linked at sites remote from the antigen binding sites. This can be accomplished by, e.g., linkage to cleaved interchain sulfydryl groups, as noted above. Another method involves reacting an antibody having an oxidized carbohydrate portion with another antibody which has at lease one free amine function. This results in an initial Schiff base (imine) linkage, which is preferably stabilized by reduction to a secondary amine, e.g., by borohydride reduction, to form the final product. Such site-specific linkages are disclosed, for small molecules, in U.S. Pat. No. 4,671,958, and for larger addends in U.S. Pat. No. 4,699,784.

The interchain disulfide bridges of the an F(ab')2 fragment having target specificity can be reduced with cysteine, avoiding light-heavy chain linkage, to form Fab'-SH fragments. The SH group(s) can be activated with an excess of bis-maleimide linker (1,1'-15 (methylenedi-4,1-phenylene)bis-malemide).

In on embodiment, hL243 antibodies disclosed herein, as well as other binding molecules with different specificities may be used in combination therapy. For example, the multispecific antibodies may include at least one binding site to an epitope recognized by the murine monoclonal antibody mL243, or antigen, and at least one binding site to another epitope recognized by the murine monoclonal antibody mL243, or another antigen. In addition, multivalent antibodies (including multiple binding sites to the same epitope or antigen), or the antibodies may be both multivalent and multispecific.

In one particular embodiment, a binding molecule may be a fusion protein. In one more particular embodiment, the fusion protein may contain four or more Fvs or Fab's of a humanized, chimeric, human or murine L243 antibodies or fragment as described herein. In another embodiment, an antibody fusion protein may contain one or more Fvs or Fab's of the mAbs or fragments of a humanized, chimeric, human or murine L243 MAb or fragment as described herein. In accordance with these embodiments, one or more Fvs or Fab's from antibodies specific for another antigen that is specific for a cell marker other than an HLA antigen may be included. For example, the non-HLA antigen may include a tumor marker selected from a B-cell lineage antigen, (e.g., CD19, CD20, or CD22 for the treatment of B-cell malignancies). In another example, the non-HLA antigen may also be expressed on other cells that cause other types of malignancies, such as S100 in melanoma, etc. Further, the cell marker may be a non-B-cell lineage antigen, such as selected from the group consisting of HLA-DR, CD30, CDS3, CD52, CD66, MUC1 and TAC.

In one embodiment, an L243 antibody disclosed herein may be combined with other antibodies and used to treat a subject having or suspected of developing a disease. In accordance with this embodiment, an L243 antibody or composition thereof may be combined with an anticancer monoclonal antibody such as a humanized monoclonal antibody (e.g. hA20 (CD20 Mab)) and used to treat cancer. In a more particular embodiment, an HLA-DR antibody of L243 may be combined with an anticancer monoclonal antibody (e.g. hA20) and used to treat a subject having of suspected of developing a disease. It is contemplated herein that an hL243 antibody may be used as a separate antibody composition in combination with one or more other separate antibody compositions, as well as, used as a bi-functional antibody for example one of hL243 and the other another of hA20. In accordance with this embodiment, the hL243 antibody may be the HLA-DR of hL243. In another particular embodiment, the disease may include targetin a B-cell malignancy disease in a subject having such a disease. The B-cell malignancy may consist of indolent forms of B-cell lymphomas, aggressive forms of B-cell lymphomas, chronic lymphatic leukemias, acute lymphatic leukemias, Waldenstrom's macroglobulinemia, and multiple myeloma. There are also non-malignant B-cell disorders and related diseases, such as many autoimmune and immune dysregulatory diseases, including septicemia and septic shock among immune dysregulatory diseases (see also U.S. Provisional Application No. 60/634, 076 filed on Dec. 8, 2004, by Goldenberg and Hansen,and incorporated herein in its entirety). In particular, the compositions described herein are particularly useful for treatment of various autoinmmune dieases, as well as indolent forms of B-cell lymphomas, aggressive forms of B-cell lymphomas, chronic lymphatic leukemias, acute lymphatic leukemias, multiple myeloma, and Waldenstrom's macroglobulinemia, as well as other hematopoietic malignancies, such as acute and chronic myeloid leukemias and T-cell leukemias and lymphomas. For example, the hL243 antibody components and immunoconjugates can be used preferably to treat both indolent and aggressive forms of non-Hodgkin's lymphoma and lymphoid leukemias.

Tumor-associated antigens that may be targeted include, but are not limited to, A3, antigen specific for A33 antibody, BrE3-antigen, CD1, CD1a, CD3, CD5, CD15, CD19, CD20, CD21, CD22, CD23, CD25, CD30, CD45, CD74, CD79a, CD80, HLA-DR, NCA 95, NCA90, HCG and its subunits, CEA (CEACAM-5), CEACAM-6, CSAp, EGFR, EGP-1, EGP-2, Ep-CAM, Ba 733, HER2/neu, hypoxia inducible factor (HIF), KC4-antigen, KS-1-antigen, KS 1-4, Le-Y, macrophage inhibition factor (MIF), MAGE, MUC1, MUC2, MUC3, MUC4, PAM-4-antigen, PSA, PSMA, RS5, S100, TAG-72, p53, tenascin, IL-6, IL-8, insulin growth factor-1 (IGF-1), Tn antigen, Thomson-Friedenreich antigens, tumor necrosis antigens, VEGF, 17-1A-antigen, an angiogenesis marker (e.g., ED-B fibronectin), an oncogene marker, an oncogene product, and other tumor-associated antigens. Recent reports on tumor associated antigens include Mizukami et al., (2005, *Nature Med.* 11:992-97); Hatfield et al., (2005, *Curr. Cancer Drug Targets* 5:229-48); Vallbohmer et al. (2005, *J. Clin. Oncol.* 23:3536-44) and Ren et al. (2005, *Ann. Surg.* 242:55-63), each incorporated herein by reference.

In addition, another embodiment of the present invention may include bispecific or multispecific antibodies for preparing immunoconjugates and compositions. In accordance with these embodiments, L243 antibodies or fragments or antibody fusion proteins thereof may be linked to an antibody or antibody fragment specific for a cancer marker substance, an epitope on the surface of an infectious disease organism, or a noxious substance in the blood or other body fluids. The bispecific and multispecific antibodies may be useful for inducing clearance of a variety of noxious substances. For example, a bispecific antibody may have one or more specificities for a noxious substance, such as a pathogenic organism, and one or more specificities for HLA-DR, the HLA class-II invariant chain (Ii). The HLA class-II invariant chain (li) is described in detail in U.S. Ser. No. 09/314,135, filed on May 19, 1999, entitled "Therapeutic Using a Bispecific Antibody," which is herein incorporated in its entirety by reference.

In another embodiment, the immunoconjugates and compositions disclosed herein may also include a L243 multivalent antibody. In accordance with this embodiment, a multivalent target binding protein may be constructed by association of a first and a second polypeptide. The first polypeptide may include a first single chain Fv molecule covalently linked to a first immunoglobulin-like domain that preferably is an immunoglobulin light chain variable region domain. The second polypeptide may include a second single chain Fv molecule covalently linked to a second immunoglobulin-like domain that preferably is an immunoglobulin heavy chain variable region domain. Each of the first and second single chain Fv molecules forms a target binding site, and the first and second immunoglobulin-like domains associate to form a third target binding site.

In an alternative embodiment, a humanized, chimeric or human L243 monoclonal antibody may be used to produce antigen specific diabodies, triabodies, and tetrabodies. For example, the monospecific diabodies, triabodies and tetrabodies may bind selectively to targeted antigens and as the number of binding sites on the molecule increases, the affinity for the target cell increases and a longer residence time is observed at the desired location. For diabodies, the two chains comprising the VH polypeptide of the humanized L243 mAb connected to the VK polypeptide of the humanized L243 mAb by a five amino acid residue linker can be utilized. Each chain forms one half of the humanized L243 diabody. In the case of triabodies, the three chains comprising VH polypeptide of the humanized L243 MAb connected to the VK polypeptide of the humanized L243 MAb by no linker are utilized. Each chain forms one third of the hL243 triabody.

In another embodiment, the immunoconjugates and compositions disclosed herein may also include functional bispecific single-chain antibodies (bscAb) (See, e.g., Mack et al., *Proc. Natl. Acad. Sci. USA,* 92:7021-7025, 1995, incorporated herein by reference). For example, bscAb can be produced by joining two single-chain Fv fragments via a glycine-serine linker using recombinant methods. The V light-chain (VL) and V heavy-chain (VH) domains of two antibodies of interest can be isolated using standard PCR methods. The VL and VH cDNA's obtained from each hybridoma may be joined to form a single-chain fragment in a two-step fusion PCR. In one example, the first PCR step introduces the (Gly4-Serl)3 linker, and the second step joins the VL and VH amplicons. Each single chain molecule can be cloned into a bacterial expression vector. Following amplification, one of the single-chain molecules can be excised and sub-cloned into the other vector, containing the second single-chain molecule of interest. Then the bscAb fragment can be subcloned into a eukaryotic expression vector. Functional protein expression can be obtained by transfecting the vector into Chinese Hamster Ovary cells. Other bispecific fusion proteins are prepared in a similar manner. Bispecific single-chain antibodies and bispecific fusion proteins may be used to prepare the drug carriers.

In addition, one embodiment may include a tetravalent tandem diabody (termed tandab) with dual specificity (Cochlovius et al., Cancer Research (2000) 60: 4336-4341). A bispecific tandab is a dimer of two identical polypeptides, each containing four variable domains of two different antibodies (VH1, VL1, VH2, VL2) linked in an orientation to facilitate the formation of two potential binding sites for each of the two different specificities upon self-association.

In another embodiment, a conjugated multivalent L243 antibody may be used to prepare the immunoconjugate or composition. Additional amino acid residues may be added to either the N- or C-terminus of the first or the second polypeptide. The additional amino acid residues may comprise a peptide tag, a signal peptide, a cytokine, an enzyme (for example, a pro-drug activating enzyme), a hormone, an oligonucleotide, an interference RNA, a peptide toxin, such as pseudomonas exotoxin, a peptide drug, a cytotoxic protein or other functional proteins. As used herein, a functional protein is a protein that has a biological function.

In yet another embodiment, the hL243 antibody, or fragments thereof, may be used to prepare a polyvalent protein complex, a novel antibody fusion protein comprising three or four antigen binding sites. In accordance with these embodiments, one or more antigen binding sites may be composed of the hL243 variable domains, and one or more of the remaining antigen binding sites may include variable domains of other antigen-specific antibodies as desired. Such polyvalent protein complexes are described in PCT Publication WO04094613A2 (Rossi et al., 2004). When combined with an appropriate antigen specific antibody variable chain, a polyvalent protein complex comprising a hL243 variable domain may be used to treat a variety of neoplastic, infectious, metabolic, neurodegenerative, autoimmune, or immune dysregulation disorders.

In one embodiment of the present invention, drugs, toxins, radioactive compounds, enzymes, hormones, cytotoxic proteins, oligonucleotides, interfering RNAs (e.g. RNAi molecules), chelates, cytokines and other functional agents may be conjugated to a multivalent target binding protein. In accordance with these embodiments, covalent attachments to the side chains of the amino acid residues of the multivalent target binding protein may be used, for example amine, carboxyl, phenyl, thiol or hydroxyl groups. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the multivalent protein preferably does not significantly affect the protein's binding specificity or affinity to its target. As used herein, a functional agent is an agent which has a biological function. A preferred functional agent is a cytotoxic agent.

In still other embodiments, bispecific antibody-directed delivery of therapeutics or prodrug polymers to in vivo targets can be combined with bispecific antibody delivery of radionuclides, such that combination chemotherapy and radioimmunotherapy is achieved. Each therapeutic agent can be conjugated to a targetable conjugate and administered simultaneously, or the nuclide can be given as part of a first targetable conjugate and the drug given in a later step as part of a second targetable conjugate. Suitable targetable conjugates and drugs are known in the art.

In another embodiment, cytotoxic agents may be conjugated to a polymeric carrier, and the polymeric carrier may subsequently be conjugated to the multivalent target binding protein. For this method, see Ryser et al, *Proc. Natl. Acad. Sci. USA,* 75:3867-3870,1978, U.S. Pat. Nos. 4,699,784 and 4,046,722, which are incorporated herein by reference. Conjugation preferably does not significantly affect the binding specificity or affinity of the multivalent binding protein.

Humanized, Chimeric and Human Antibodies Use for Treatment and Diagnosis

Humanized, chimeric and human monoclonal antibodies described herein, are suitable for use in the therapeutic methods and diagnostic methods which utilize immunoconjugates and compositions as described herein. Accordingly, the immunoconjugates or compositions may include naked humanized, chimeric and human antibodies or antibodies, which may be conjugated to a carrier, a therapeutic agent, or a diagnostic agent. The immunoconjugates may be administered as a multimodal therapy. For example, additional therapeutic or diagnostic agents may be administered before, simultaneously, or after administration of the immunoconjugate or composition. The efficacy of the immunoconjugates or compositions may be enhanced by supplementing the humanized, chimeric and human L243 immunoconjugates or compositions with one or more other binding molecules (i.e., mAbs to specific antigens, such as CD4, CDS, CD8, CD14, CD15, CD19, CD21, CD22, CD23, CD25, CD30, CD33, CD37, CD38, CD40, CD40L, CD46, CD52, CD54, CD74, CD80, CD126, CCD138, CD154, B7, MUC1, MUC2, MUC3, MUC4, MUC16, NCA66, necrosis antigens, PAM-4, KS-1, Le(y), MAGE, la, IL-2, IL-6, tenascin, HM1.24, VEGF, EGFR, EGP-1, EGP-2, folate receptor, human chorionic gonadotropin, colon-specific antigen-p (CSAp), insulin-like growth factor (ILGF), placental growth factor (PIGF), prostatic acid phosphatase, PSA, PSMA, T101, TAG, TAG-72, Her2/neu, carbonic anhydrase IX, IL-6, S100, alpha-fetoprotein, A3, CA125, carcinoembryonic antigen (CEA), nonspecific cross-reacting antigens such as CD66 (a,b,c,d), MART-1, TRP-1, TRP-2, gp100, amyloid, with hL243 antibodies, or immunoconjugates thereof, or antibodies to these recited antigens). Preferred B-cell-associated antigens include those equivalent to human CD 19, CD20, CD21, CD22, CD23, CD46, CD52, CD74, CD80, and CDS antigens. Preferred T-cell antigens include those equivalent to human CD4, CDS and CD25 (the IL-2 receptor) antigens.

Alternatively, substitute molecule for an HLA-DR antigen may be used in treatment of both B-cell and T-cell disorders. In one particular embodiment, B-cell antigens can be equivalent to human CD 19, CD22, CD21, CD23, CD74, CD80, and HLA-DR antigens. In another particular embodiment, T-cell antigens equivalents to human CD4, CDS and CD25 antigens can be used. Alternatively, CD46 and CD59 antigens on the surface of cancer cells that block complement-dependent lysis (CDC) may be used. In one embodiment, malignant melanoma associated antigens such as equivalent to MART-1, TRP-1, TRP-2 and gp100 may be used. Further, in one particular embodiment, multiple myeloma-associated antigens are those equivalent to MUC1, CD38, and CD74.

In one example, the supplemental binding molecule may be naked or conjugated with a carrier, a therapeutic agent, or a diagnostic agent, including lipids, polyers, drugs, toxins, immunomodulators, hormones, enzymes, oligonucleotides, interference RNAs, and therapeutic radionuclides, etc. In accordance with this embodiment, the supplemental binding molecule may be administered concurrently, sequentially, or according to a prescribed dosing regimen, with the humanized, chimeric and human L243 immunoconjugates or compositions.

Further, the administration of an immunoconjugate or composition for diagnostic and therapeutic uses in B-cell lymphomas, T-cell lymphomas, and other diseases or disorders is contemplated herein. An immunoconjugate, as described herein, may be a molecule including a binding molecule conjugated to a carrier. In accordance with this embodiment, the immunoconjugate may be used to form a composition that further includes a therapeutic or diagnostic agent, which may include a peptide that may bear the diagnostic or therapeutic agent. An immunoconjugate retains the immunoreactivity of the binding molecule (i.e., the antibody moiety has about the same or slightly reduced ability to bind the cognate antigen after conjugation as before conjugation). Immunoconjugates may include binding molecules conjugated to any suitable second molecule (e.g., lipids, proteins, carbohydrates, which may form higher-ordered structures, or higher-ordered structures themselves, such as liposomes, micelles, and/or nanoparticles). To facilitate delivery of certain effectors, it may be desirable to conjugate the hL243 antibody to one or more molecules that are capable of forming higher-ordered structures (e.g., amphiphilic lipids). Amphiphilic molecules may also be desirable to facilitate delivery of effectors that demonstrate limited solubility in aqueous solution.

In another embodiment, a wide variety of diagnostic and therapeutic reagents can be used to form the immunoconjugates and compositions as described herein. Therapeutic agents include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and apoptotic agents, particularly doxorubicin, methotrexate, taxol, CPT-11, camptothecans, and others from these and other classes of anticancer agents, and the like. Other useful cancer chemotherapeutic drugs for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, and the like. Suitable chemotherapeutic agents are described in Remington's Pharmaceutical Sciences, 19th Ed. (Mack Publishing Co. 1995), and in Goodman and Oilman's The pharmacological Basis of Therapeutics, 7th Ed. (MacMillan Publishing Co. 1985), as well as revised editions of these publications. Other suitable chemotherapeutic agents, such as experimental drugs, may be used and are known in the art.

Additionally, in another embodiment, a chelator such as DTPA, DOTA, TETA, or NOTA may be conjugated to one or more components of the compositions as described herein. Alternatively, a suitable peptide including a detectable label, (e.g., a fluorescent molecule), or a cytotoxic agent, (e.g., a heavy metal or radionuclide), can be covalently, non-covalently, or otherwise associated with more components of the compositions as described herein. For example, one therapeutically useful immunoconjugate may be obtained by incorporating a photoactive agent or dye in the composition as described herein. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, Chem. Britain 22:430 (1986)). Moreover, monoclonal antibodies have been coupled with photoactivated dyes for achieving phototherapy. Mew et al., J. Immunol. 130:1473 (1983); idem., Cancer Res. 45:4380 (1985); Oseroffet al., Proc. Natl. Acad. Sci. USA 83:8744 (1986); idem., Photochem. Photobiol. 46:83 (1987); Hasan et al., Prog. Clin. Biol. Res. 288:471 (1989); Tatsuta et al., Lasers Surg. Med. 9:422 (1989); Pelegrin et al., Cancer 67:2529 (1991). Endoscopic applications are also contemplated. Endoscopic methods of detection and therapy are described in U.S. Pat. Nos. 4,932,412; 5,525,338; 5,716,595; 5,736,119; 5,922,302; 6,096,289; and 6,387,350, which are incorporated herein by reference in their entirety.

In one embodiment, it is contemplated herein that the therapeutic use of hL243 immunoconjugate compositions comprising photoactive agents or dyes, and the present diagnostic/therapeutic methods may include the diagnostic or therapeutic use of hL423 immunoconjugate compositions comprising photoactive agents or dyes. The immunoconjugate may also contain ultrasound agents of the types discussed above. Also contemplated is the use of radioactive and non-radioactive agents as diagnostic agents in the humanized, chimeric and human L423 immunoconjugate compositions as described herein. A suitable non-radioactive diagnostic agent is a contrast agent suitable for magnetic resonance imaging, computed tomography or ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies described herein. (See U.S. Ser. No. 09/921,290 filed on Oct. 10, 2001, which is incorporated in its entirety by reference).

In another embodiment, a humanized, chimeric and human L423 immunoconjugate composition may include a radioisotope or a positron-emitter useful for diagnostic imaging. Suitable radioisotopes may include those in the energy range of 60 to 4,000 keV. Suitable radioisotopes may include 18-F, 52-Fe, 62-Cu, 64-Cu, 67-Cu, 67-Ga, 68-Ga, 86-Y, 89-Zr, 94-Tc, 94m-Tc, 99m-Tc, 111-In, 123-I, 124-I, 125-I, 131-I, and the like. (See, e.g., U.S. Patent Application entitled "Labeling Targeting Agents with Gallium-68"—Inventors G. L. Griffiths and W. J. McBride (U.S. Provisional Application No. 60/342,104), which discloses positron emitters, such as 18-F, 68-Ga, 94m-Tc. and the like, for imaging purposes and which is incorporated in its entirety by reference).

In another embodiment of the present invention, a toxin, such as *Pseudomonas* exotoxin, may be present in the humanized, chimeric and human L243 antibodies, or immunoconjugates or compositions therof, as described herein. For example, the toxin may be complexed to or form the therapeutic agent portion of an antibody fusion protein of an the hL243 antibody described herein. Other toxins include ricin, abrin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin. (See, e.g., Pastan et al., Cell 47:641 (1986), and Goldenberg, CA-A Cancer Journal for Clinicians 44:43 (1994). Additional toxins suitable for use herein are known to those of skill in the art and are disclosed in U.S. Pat. No. 6,077,499, which is incorporated in its entirety by reference).

Alternatively, an immunomodulator, such as a cytokine may also be present in the administered hL423 mmunoconjugate compositions as described herein. For example, an immunomodulator may be conjugated to, or form the therapeutic agent portion of an antibody fusion protein or be administered as part of the humanized, chimeric and human L423 immunoconjugate compositions as described herein. Suitable cytokines include, but are not limited to, interferons and interleukins, as described below.

In one embodiment, a humanized L243 antibody can be used as part of pretargeting, a non-immunogenic, highly selective alternative for diagnostic and therapeutic applications, in which a bi-specific antibody is employed that co-recognizes a tumor antigen and one or more haptens on a carrier molecule, where the carrier molecule may include an effector molecule. Bispecific antibodies (bsAb) have the advantage of being capable of being engineered as a relatively non-immunogenic humanized protein. The binding affinity of a bsAb may dependent on the binding affinity of the primary targeting agent. By using a divalent peptide, an affinity enhancement may be achieved, which can greatly improve the binding of the peptide to the target site compared to a monovalent peptide. See, for example, U.S. Pat. No. 5,256, 395, the contents of which are incorporated herein in their entirety.

In one embodiment, pretargeting with an hL243 bsAb may include one arm of the bsAb derived from the variable regions of an hL243 antibody as herein described, and the second arm of the antibody recognizing a moiety that contains a diagnostic or therapeutic agent (e.g., a carrier with a diagnostic or therapeutic agent together as a "targetable construct"). Suitable targetable constructs and methods of use are described in U.S.Patent Application 20050002945, the contents of which are hereby incorporated by reference in their entirety. The targetable construct may be, for example, (i) DOTA-Phe-Lys (HSG)-D-Tyr-Lys(HSG)-NH$_2$; (ii) DOTA-Phe-Lys(HSG)-Tyr-Lys-(HSG)-NH$_2$; or (iii) Ac-Lys(HSG)D-Tyr-Lys(HSG)-Lys(Tsc$_g$-Cys)-NH$_2$, although the skilled artisan will appreciate that other targetable constructs may be used. In other systems, the targetable construct comprises a haptenic moiety that is recognized by the second arm of the antibody and a therapeutic or diagnostic agent. For example, a therapeutic agent can be a chemotherapeutic agent or a toxin, such as those described above.

One particular embodiment includes a pretargeting system described by Janevik-Ivanovska et al. that uses an antibody directed against a histamine derivative, histamine-succinyl-glycl (HSG), as the recognition system on which a variety of effector substances could be prepared. Humanized L243 antibodies of the present invention may be used in such a system. This pretargeting system represents a significant advantage over other pretargeting systems in that it can be used with a variety of different imaging or therapeutic agents. In one example, this system may be based on use of an antibody directed against DTPA or HSG and the development of peptides containing the DTPA or HSG residue. DTPA-containing and/or HSG-containing peptides can be synthesized, and where the peptide contains DTPA, the peptide may be labeled with chelated nuclides, such as In, Y, or Lu, which may be useful in therapy or diagnosis. Antibodies have been generated against the DTPA- In moiety. In other embodiments, the system includes peptides of haptens and/or chelators such as DTPA, and which may be suitable for radiolabeling with $^{90}$Y, $^{111}$in, and $^{177}$Lu, as well as $^{99m}$Tc.

Preparation of Immunoconjugates

The immunoconjugates described herein may be prepared by known methods of linking antibodies with lipids, carbohydrates, protein, or other atoms and molecules. For example, the binding molecules described herein can be conjugated with one or more of the carriers described herein (e.g., lipids, polymers, liposomes, micelles, or nanoparticles) to form an immunoconjugate, and the immunoconjugate can incorporate a therapeutic or diagnostic agent either covalently, non-covalently, or otherwise. Further, any of the binding molecules described herein can be conjugated with one or more therapeutic or diagnostic agents described herein, or additional carriers. Generally, one therapeutic or diagnostic agent may be attached to each binding molecule but more than one therapeutic agent or diagnostic agent can be attached to the same binding molecule. In one embodiment, the antibody fusion proteins contemplated herein may include two or more antibodies or fragments thereof and each of the antibodies that include this fusion protein may be conjugated with one or more of the carriers described herein. Additionally, one or more of the antibodies of the antibody fusion protein may have one or more therapeutic of diagnostic agent attached. Further, the therapeutic do not need to be the same but can be different therapeutic agents. For example, the compositions described herein may include a drug and a radioisotope.

In one example, an IgG maybe radiolabeled with 131-I and conjugated to a lipid, such that the IgG-lipid conjugate can form a liposome. In accordance with this example, the liposome may incorporate one or more therapeutic or diagnostic agents, (e.g., a drug such as FUdR-dO). Alternatively, in addition to the carrier, the IgG may be conjugated to 131-I (e.g., at a tyrosine residue) and a drug (e.g., at the epsilon amino group of a lysine residue), and the carrier may incorporate an additional therapeutic or diagnostic agent. Therapeutic and diagnostic agents may be covalently associated with the binding molecule, (e.g., conjugated to reduced disulfide groups, carbohydrate sidechains, or any other reactive group on the binding molecule.

In another embodiment, a carrier, therapeutic agent, or diagnostic agent may be attached at the hinge region of a reduced antibody component via disulfide bond formation. As an alternative, peptides can be attached to an antibody component using a heterobifunctional cross-linker, such as N-succinyl 3-(2-pyridyldithio)proprionate (SPDP). Yu et al., Int. J. Cancer 56: 244 (1994). General techniques for such conjugation are well known in the art. (See, e.g., Wong, Chemistry of Protein Conjugation and Cross-linking (CRC Press 1991); Upeslacis et al., "Modification of Antibodies by Chemical Methods," in Monoclonal Antibodies Principles and Applications, Birch et al. (eds.), pages 187D230 (Wiley-Liss, Inc. 1995); Price, "Production and Characterization of Synthetic Peptide-Derived Antibodies," in Moniclonal Antibodies: Production, Engineerting and Clinical Application, Ritter et al. (eds.), pages 60D84 (Cambridge University Press 1995)). Alternatively, the carrier, therapeutic agent, or diagnostic agent can be conjugated via a carbohydrate moiety in the Fc region of an antibody. The carbohydrate group can be used to increase the loading of the same peptide that is bound to a thiol group, or the carbohydrate moiety can be used to bind a different peptide.

Method for conjugating peptides to antibody components via an antibody carbohydrate moiety are well known to those of skill in the art. (See, e.g., Shih et al., Int. J. Cancer 41: 832 (1988); Shih et al., Int. J. Cancer 46: 1101 (1990); and Shih etal., U.S. Pat. No. 5,057,313, all of which are incorporated in their entirety by reference). Similar chemistry may be used to conjugate one or more hL243 antibodies, or components thereof, to one or more carriers, therapeutic agents, or diagnostic agents. In one embodiment, one general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

In one embodiment, the Fc region may be absent, for example, if the hL423 binding molecule is an antibody fragment. Alternatively, a carbohydrate moiety may be introduced into the light chain variable region of a full-length antibody or antibody fragment. (See, e.g., Leung et al., J. Immunol. 154: 5919 (1995); Hansen etal., U.S. Pat. No. 5,443,953 (1995), Leung etal., U.S. Pat. No. 6,254,868, all of which are incorporated in their entirety by reference). In accordance with these embodiments, the engineered carbohydrate moiety may be used to attach a carrier, a therapeutic or diagnostic agent.

Carriers (Lipids, Liposomes, Micelles, Polymers, and Nanoparticles)

Any methods for formation of liposomes and micelles may be use and are known in the art. (See, e.g., Wrobel et al., Biochimica et Biophysica Acta, 1235:296 (1995); Lundberg et al., J. Pharm. Pharmacol., 51:1099-1105 (1999); Lundberg et al., Int. J. Pharm., 205:101-108 (2000); Lundberg, J. Pharm. Sci., 83:72-75 (1994); Xu et al., Molec. Cancer Then, 1:337-346 (2002); Torchilin et al., Proc. Nat'l. Acad. Sci. USA, 100:6039-6044 (2003); U.S. Pat. Nos. 5,565,215; 6,379,698; and U.S. 2003/0082154). Nanoparticles or nanocapsules formed from polymers, silica, or metals, which are contemplated herein for drug delivery or imaging, have been described. (See, e.g., West et al., Applications of Nanotechnology to Biotechnology, 11:215-217 (2000); U.S. Pat. Nos. 5,620,708; 5,702,727; and 6,530,944).

Immunoliposomes

Some methods to conjugate antibodies or binding molecules to liposomes to form a targeted carrier for therapeutic or diagnostic agents has been described. (See, e.g., Bendas, Biodrugs, 15:215-224 (2001); Xu et al., Molec. Cancer Ther., 1:337-346 (2002); Torchilin et al., Proc. Nat'l. Acad. Sci., 100:6039-6044 (2003); Bally, et al., J. Liposome Res., 8:299-335 (1998); Lundberg, Int. J. Pharm., 109:73-81 (1994); Lundberg, J. Pharm. Pharmacol., 49:16-21 (1997);Lundberg, Anti-cancer Drug Design, 13:453-461 (1998)). See also U.S. Pat. No. 6,306,393; U.S. Ser. Nos. 10/350,096; 09/590,284, and U.S. Ser. No. 60/138,284, filed Jun. 9, 1999. All these references are incorporated herein by reference.

Pharmaceutically Acceptable Excipients

In one embodiment, the immunoconjugates or compositions may include one or more pharmaceutically suitable excipients, one or more additional ingredients, or combination thereof.

In another embodiment, the immunoconjugate or compositions disclosed herein may be formulated according to known methods to prepare pharmaceutically useful compositions, whereby the immunoconjugate or compositions are combined in a mixture with a pharmaceutically suitable excipient. Sterile phosphate-buffered saline is one example of a pharmaceutically suitable excipient. Other suitable excipients are well known to those in the art. (See, e.g., Ansel et al., Pharmaceutical Dosage Forms and Drug Delivery Systems, 5th (Lea & Febiger 1990), and Gennaro (ed), Remington's Pharmaceutical Sciences, 18th Edition (Mack Publishing Company 1990), and revised editions thereof.

In another embodiment, the immunoconjugate or compositions disclosed herein can be formulated for intravenous administration via, for example, bolus injection or continuous infusion.

Formulations for injection may be presented for example in unit dosage form, e.g., in ampules or in multi-dose containers, with an added preservative. The compositions may take such forms as suspensions, solutions or emulsions in oily or aqueous vehicles, and can contain formulatory agents such as suspending, stabilizing and/or dispersing agents. Alternatively, the active ingredient may be in powder form for constitution with a suitable vehicle, e.g., sterile pyrogen-free water, before use. Additional pharmaceutical methods may be employed to control the duration of action of the therapeutic, diagnostic conjugate or naked antibody. For example, control release preparations may be prepared through the use of polymers to complex or adsorb the immunoconjugate or naked antibody. In one example, biocompatible polymers include matrices of poly(ethylene-co-vinyl acetate) and matrices of a polyanhydride copolymer of a stearic acid dimer and sebacic acid. Sherwood et al., Bio/Technology 10: 1446 (1992). Some of the rates of release of an immunoconjugate or antibody from such a matrix depends upon the molecular weight of the immunoconjugate or antibody, the amount of immunoconjugate, antibody within the matrix, and the size of dispersed particles. Saltzman et al., Biophys. J. 55: 163 (1989); Sherwood et al., supra. Other solid dosage forms are described in Ansel et al., Pharmaceutical Dosage Forms and Drug Delivery Systems, 5th Edition (Lea & Febiger 1990), and Gennaro (ed.), Remington's Pharmaceutical Sciences, 18th Edition (Mack Publishing Company 1990), and revised editions thereof.

In one embodiment, the immunoconjugate or compositions may also be administered to a mammal subcutaneously or even by other parenteral routes. Moreover, the administration may be by continuous infusion or by single or multiple boluses. In one example, the dosage of an administered immunoconjugate, fusion protein or naked antibody for humans will vary depending upon such factors as the patient's age, weight, height, sex, general medical condition and previous medical history etc. In a particular embodiment, the recipient may be administered a dosage of immunoconjugate or composition including the immunoconjugate that is in the range of from about 1 mg/kg to mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

In one embodiment, for purposes of therapy, the immunoconjugate, or composition including the immunoconjugate, is administered to a mammal in a therapeutically effective amount. A suitable subject for the therapeutic and diagnostic methods disclosed herein may be a human, although a non-human animal subject is also contemplated.

In one example an antibody preparation is said to be administered in a "therapeutically effective amount" if the amount administered is physiologically significant. An agent is physiologically significant if its presence results in a detectable change in the physiology of a recipient mammal. In particular, an antibody preparation is physiologically significant if its presence invokes an antitumor response or mitigates the signs and symptoms of an autoimmune disease state. A physiologically significant effect could also be the evocation of a humoral and/or cellular immune response in the recipient mammal.

Methods of Treatment Using Compositions Including Humanized, Chimeric and Human L243 Antibodies In one embodiment, immunological diseases which may be treated with the antibodies of the present invention may include, for example, joint diseases such as ankylosing spondylitis, juvenile rheumatoid arthritis, rheumatoid arthritis; neurological disease such as multiple sclerosis and myasthenia gravis; pancreatic disease such as diabetes, especially juvenile onset diabetes; gastrointestinal tract disease such as chronic active hepatitis, celiac disease, ulcerative colitis, Crohn's disease, pernicious anemia; skin diseases such as psoriasis or scleroderma; allergic diseases such as asthma and in transplantation related conditions such as graft versus host disease and allograft rejection.

In another embodiment of the present invention, compositions and methods are provided that may include the antibodies disclosed herein, or immunoconjugates thereof, for treating an autoimmune disease or disorder. Immunotherapy of autoimmune disorders using antibodies which target B-cells is described in PCT Application Publication No.WO 00/74718, which claims priority to U.S. Provisional Application Ser. No. 60/138,284, the contents of each of which is incorporated herein in its entirety. Exemplary autoimmune diseases include but are not limited to acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, parnphigus vulgaris, Wegener's granulomatosis, membranous nephropathy, amyotrophic lateral sclerosis, tabes dorsalis, giant cell arteritis/polymyalgia, perniciousanemia, rapidly progressive glomerulonephritis, psoriasis, and fibrosing alveolitis.

In another embodiment of the present invention compositions and methods are provide for treating a disorder selected from the group consisting of a carcinoma, a sarcoma, a glioma, a lymphoma, a leukemia, or a skin cancer. The carcinoma may be selected from the group consisting of a skin, an esophageal, a gastric, a colonic, a rectal, a pancreatic, a lung, a breast, an ovarian, a urinary bladder, an endometrial, a cervical, a testicular, a renal, an adrenal or a liver cancer. The B-cell related disease may be an indolent form of B-cell lymphoma, an aggressive form of B-cell lymphoma, non-Hodgkin's lymphoma, a chronic lymphocytic leukemia, an acute lymphocytic leukemia, a Waldenstrom's macroglobulinemia, or a multiple myeloma. In addition, the B-cell related disease can be a human or a veterinary type of disease. On the other hand, a T cell related disease may include a human or other mammalian T-cell leukemia or lymphoma, skin psoriasis, psoriatic arthritis or mycosis fungoides. In one example, the metabolic disease may be an amyloidosis. In one example, the neurodegenerative disease may be Alzheimer's disease.

Also, contemplated herein in one embodiment of the invention is the use of the antibodies, including immunoconjugates, as a composition for treatment of any of the following diseases or disorders, where the disease or disorder is selected from the group consisting of an immune dysregulation disease, an autoimmune disease, organ graft rejection, graft versus host disease, metabolic disease (e.g., amyloidosis), and neurodegenerative disease (e.g., Alzheimer's disease). The malignant disease or disorder is selected from the group consisting of a solid tumor, a hematopoietic tumor (lymphoma, leukemia, myeloma and the like). The solid tumor is selected from the group consisting of a melanoma, carcinoma and sarcoma and the carcinoma is selected from the group consisting of a renal carcinoma, breast carcinoma, lung carcinoma, gastrointestinal carcinoma, and urogenital carcinoma. The B-cell malignancy is selected from the group consisting of indolent forms of B-cell lymphomas, aggressive forms of B-cell lymphomas, chronic lymphatic leukemias, acute lymphatic leukemias, Waldenstrom's macroglobulinemia, and multiple myeloma. There are also non-malignant B-cell disorders and related diseases, such as many autoimmune and immune dysregulatory diseases, including septicemia and septic shock among immune dysregulatory diseases (a list of immune dysregulatory diseases may be found more comprehensively in U.S. Provisional Application No. 60/634,076 filed on Dec. 8, 2004, by Goldenberg and Hansen,and incorporated herein in its entirety). In particular, the compositions described herein are particularly useful for treatment of various autoimmune dieases, as well as indolent forms of B-cell lymphomas, aggressive forms of B-cell lymphomas, chronic lymphatic leukemias, acute lymphatic leukemias, multiple myeloma, and Waldenstrom's macroglobulinemia, as well as other hematopoietic malignancies, such as acute and chronic myeloid leukemias and T-cell leukemias and lymphomas. For example, the hL243 antibody components and immunoconjugates can be used preferably to treat both indolent and aggressive forms of non-Hodgkin's lymphoma and lymphoid leukemias.

In another embodiment, the humanized, chimeric and human L243 antibodies of the present invention may be used to treat the aforementioned diseases and disorders, as appropriate, in all mammals, including humans, and domestic mammals, including, but not limited to, dogs, cats, horses, and cattle.

In one particular embodiment, the method for treating a B-cell malignancy may include administering to a subject with a B-cell related malignancy, a therapeutic composition including a pharmaceutically acceptable carrier, a therapeutic agent, and an immunoconjugate including a L243 antibody, or component thereof (e.g., a humanized, chimeric, or human L243 antibody or fragment thereof or antibody fusion protein thereof), wherein the B-cell malignancy is a lymphoma or leukemia. More specifically, the B-cell malignancy is indolent forms of B-cell lymphomas, aggressive forms of B-cell lymphomas, multiple myeloma, chronic lymphatic leukemias, or acute lymphatic leukemias. In a more particular embodiment, an immunoconjugate or composition including the immunoconjugate may be administered intravenously or intramuscularly at a dose of about 20-2000 mg. that further includes administering the immunoconjugate or composition before, simultaneously, or after the administration of at least one additional therapeutic agent or diagnostic agent used to detect or treat the B-cell malignancy. For example, an additional agent may include an additional immunoconjugate as described herein, including a therapeutic or diagnostic agent. In accordance with these embodiments, a therapeutic agent may include a naked antibody, an immunomodulator, a hormone, a cytotoxic agent, an enzyme, and/or an antibody conjugated to at least one immunomodulator, radioactive label, hormone, enzyme, oligonucleotde, interference RNA, or cytotoxic agent, or a combination thereof. In one particular example, an immunomodulator may be a cytokine and the cytotoxic agent may be a drug or toxin. In a more particular embodiment, an antibody that may be administered in combination as a naked antibody or as a supplemental immunoconjugate preferably reacts with CD4, CDS, CDS, CD14, CD15, CD19, CD21, CD22, CD23, CD25, CD30, CD33, CD37, CD38, CD40, CD40L, CD46, CD52, CD54, CD74, CD80, CD126, CD138, CD154, B7, MUC1, MUC2, MUC3, MUC4, MUC16, NCA66, necrosis antigens, PAM-4, KS-1, 90 Le($\gamma$), MAGE, la, IL-2, IL-6, tenascin, HM1.24, VEGF, EGFR, EGP-1, EGP-2, folate receptor, human corionic gonadotropin, CEA, colon specific antigen-p (CSAp), insulin-like growth factor (ILGF), placental growth factor (PlGF), prostatic acid phosphatase, PSA, PSMA, T101, TAG, TAG-72, Her2/neu, carbonic anhydrase IX, IL-6, S100, alpha fetoprotein, A3, CA125, carcinoembryonic antigen (CEA), nonspecific cross-reacting antigens such as CD66 (a,b,c,d), MART-1, TRP-1, TRP-2, amyloid, or gp100.

It is also contemplated herein that a treatment of a malignancy may include administering to a subject with a malignancy other than lymphoma or leukemia, a therapeutic composition that may include: (1) a hL243 antibody, or immunoconjugate thereof, and a carrier; (2) an effector; and (3) a pharmaceutically acceptable excipient. The composition may be administered intravenously or intramuscularly at a dose of 20-2000 mg. Further, the composition may be administered before, simultaneously, or after the administration of at least one additional therapeutic agent or diagnostic agent.

Therapeutic agents, as described above and throughout the specification, may include an immunomodulator, a hormone, a cytotoxic agent, or a binding molecule (either naked or conjugated to at least one immunomodulator, radioactive label, enzyme, hormone, cytotoxic agent, antisense oligonucleotide, interference RNA, or a combination thereof, where the immunomodulator preferably is a cytokine and the cytotoxic agent preferably is a drug or toxin). A therapeutic agent or diagnostic agent may include the compositions or immunoconjugates as disclosed herein. In a particular embosiment, an antibody may be administered in combination with the therapeutic and/or diagnostic composition to treat a malignancy that is not a B-cell malignancy, but is likely reactive with a marker other than that recognized by the hL243 antibody, which is expressed by the cells that comprise the malignancy that is treated, and the antibody should be formulated in a pharmaceutically acceptable vehicle. Examples of antibodies that may be administered for malignant melanoma associated antigens are those antibodies reactive with MART-1, TRP-1, TRP-2 and gp100. Further, preferred antibodies to multiple myeloma-associated antigens include those reactive with MUC1, CD74, and CD38. The compositions for treatment may contain the WL243 antibody, or immunoconjugates thereof, alone or in combination with other antibodies, such as other humanized, chimeric, or human antibodies.

In one example, compositions may include an immunomodulator as an effector. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GMDCSF)), interferons (e.g., interferons-$\alpha,\beta$, and $\gamma$), the stem cell growth factor designated "SI factor," erythropoietin, thrombopoietin or a combination thereof. Examples of suitable immunomodulator moieties include IL-1, IL-2, IL-3, IL-6, IL-10, IL-12, IL-18, IL-21, and a combination thereof, and interferon-$\alpha$, $\beta$, and $\gamma$, TNF-$\alpha$ and $\beta$, and the like. In one embodiment, the immunomodulator may be present in the composition, or alternatively, the imnmunomodulator can be administered before, simultaneously, or after administration of the therapeutic and/or diagnostic compositions. In one particular embodiment, the hL243 antibody may also be conjugated to the immunomodulator. The immunomodulator may also be conjugated to a hybrid antibody consisting of one or more antibodies binding to different antigens.

In one example, multimodal therapies contemplated herein may include immunotherapy with immunoconjugates such as hL243 antibody supplemented with administration of additional binding molecules (e.g., anti-CD22, anti-CD19, anti-CD21, anti-CD20, anti-CD80, anti-CD23, anti-CD46 or HLA-DR, preferably the mature HLA-DR dimer antibodies in the form of naked antibodies, fusion proteins, or as immunoconjugates). Further, a micelle, liposome, or nanoparticle, as described herein, may include binding molecules in addition to hL243 antibodies. For example, antibodies may be polyclonal, monoclonal, chimeric, human or humanized antibodies that recognize at least one epitope on the above-noted antigenie determinants. In addition, anti-CD 19 and anti-CD22 antibodies are known in the art. (See, e.g., Ghetie et al., Cancer Res. 48:2610 (1988); Hekman et al., Cancer Immunol. Immunother. 32 :364 (1991); Longo, Curr. Opin. Oncol. 8:353 (1996) and U.S. Pat. Nos. 5,798,554 and 6,187,287, incorporated in their entirety by reference.)

In one particular example, another form of multimodal therapy may be where subjects receive hL243 immunoconjugates in conjunction with standard cancer chemotherapy. For example, "CVB" (1.5 g/m²cyclophosphamide, 200-400 mg/m² etoposide, and 150-200 mg/m² carmustine) is a regimen used to treat non-Hodgkin's lymphoma. Patti et al., Eur. J. Haematol. 51:18 (1993). Other suitable combination chemotherapeutic regimens are well known to those of skill in the art. (See, e.g., Freedman et al., "Non-Hodgkin's Lymphomas," in Cancer Medicine, Volume 2, 3rd Edition, Holland et al. (eds.), pages 2028-2068 (Lea & Febiger 1993)). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). In one particular embodiment of the present invention, second-generation chemotherapeutic regimen may be m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional therapeutics may include phenyl butyrate and bryostatin- 1. In a preferred multimodal therapy, both chemotherapeutic drugs and cytokines may be co-administered with an antibody, immunoconjugate or fusion protein. The cytokines, chemotherapeutic drugs and antibody or immunoconjugate cmay be administered in any order, or simultaneusly.

In a particular embodiment, NHL may be treated with 4 weekly infusions of the hL243 immunoconjugate (e.g., a therapeutic composition) at a dose of 25-700 mg/m² weekly for 4 consecutive weeks or every-other week (iv over 2-8 hours), repeated as needed over next months/yrs, more preferably at a dose of 100-400 mg/m² weekly for 4 consecutive weeks or every-other week (iv over 2-8 hours), repeated as needed over next months/yrs. In addition, NHL may be treated with 4 semi-monthly infusions as above, but combined with epratuzumab (anti-CD22 humanized antibody) on the same days, at a dose of 360 mg/m², given as an iv infusion over 1 hour, either before, during or after the hL243 antibody immunoconjugate infusion. Alternatively, HL may be treated with 4 weekly infusions of the hL243 antibody immunoconjugate as above, combined with one or more injections of CD22 mAb radiolabeled with a therapeutic isotope such as yttrium-90 (at dose of 90-Y between 5 and 35 mCi/meter-square as one or more injections over a period of weeks or months. In one example, when used in patients with lower responses to CD20 antibodies, WL243 may be combined with such CD20 antibodies as rituximab or hA20. In accordance with this example, the latter combination may be given sequentially or contemporaneously, either during the same day or week, and at varying doses, such as 375 mg/m² once weekly by i.v. infusion for rituximab or hA20 and 250 mg/m² for hL243 also given once weekly by i.v. infusion. In all the aforementioned cases, the doses may be fractionated, administered as continuous infusions, or by parenteral routes known in the art. They may also be administered by other routes, such as subcutaneously.

In addition, in one embodiment a therapeutic composition as disclosed herein may contain a mixture of or hybrid molecules of hL243 immunoconjugates directed to different, non-blocking epitopes recognized by the hL243 antibody. According to this embodiment, therapeutic compositions may include a mixture of hL243 immunoconjugates that bind at least two epitopes recognized by the hL243 antibody. Also, the immunoconjugates described herein may contain a mixture of hL243 antibodies with varying CDR sequences.

In one embodiment of the present invention, the hL243 antibodies, or immunoconjugates thereof, may be used for treating B cell lymphoma and leukemia, and other B cell diseases or disorders as well as other malignancies in which affected or associated malignant cells are reactive with epitopes recognized by the hL243 antibody. For example, hL243 antibodies, or immunoconjugates thereof, may be used to treat immune dysregulation disease and related autoimmune diseases, including but not limited to Class-III autoimmune diseases such as immune-mediated thrombocytopenias, such as acute idiopathic thrombocytopenic purpura and chronic idiopathic thrombocytopenic purpura, dermatomyositis, Sjogren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis obliterans, primary biliary cirrhosis, Hashimoto's thyroiditis, thyrotoxicosis, sclerodema, chronic active hepatitis, polymyositis/dermatomyositis, polychondritis, pamphigus *vulgaris,* Wegener's granulomatosis, membranous nephropathy, amyotrophic lateral sclerosis, tabes dorsalis, giant cell arteritis/polymyalgia, pernicious anemia, rapidly progressive glomerulonephritis, and fibrosing alveolitis.

In a more particular embodiment, hL243 antibodies, or immunoconjugates or fragments thereof or antibody fusion proteins thereof, may be administered to a subject with one or more of these autoimmune diseases. The hL243 antibodies disclosed herein are particularly useful in the method of treating autoimmune disorders, disclosed in pending U.S. Ser. No. 09/590,284 filed on Jun. 9, 2000 entitled "Immunotherapy of Autoimmune Disorders using Antibodies that Target B-Cells," which is incorporated in its entirety by reference. In one particular embodiment, the hL243 antibodies may be administered intravenously or intramuscularly at a dose of 20-2000 mg. Further, the hL243 antibodies may be administered before, during or after the administration of at least one therapeutic agent or diagnostic agent. In a more particular embodiment, the therapeutic agent, as described herein, may include an antibody, an immunomodulator, a hormone, an enzyme, a cytotoxic agent, an antibody conjugated to at least one immunomodulator, radioactive label, hormone, enzyme, or cytotoxic agent, antisense oligonucleotide, an interference RNA, or a combination thereof, where the immunomodulator is a cytokine and said cytotoxic agent is a drug or toxin. For example, the therapeutic agent may include an immunoconjugate as described herein. In one particular embodiment, antibodies that may be administered in combination as a naked antibody or as a supplemental immunoconjugate include antibodies that react with i.e., mAbs to specific antigens, such as CD4, CDS, CDS, CD14, CD15, CD19, CD21, CD22, CD23, CD25, CD30, CD33, CD37, CD38, CD40, CD40L, CD46, CD52, CD54, CD74, CD80, CD126, CCD138, CD154, B7, MUC1, MUC2, MUC3, MUC4, MUC16, NCA66, necrosis antigens, PAM-4, KS-1, Le(y), MAGE, la, IL-2, IL-6, tenascin, HM1.24, VEGF, EGFR, EGP-1, EGP-2, folate receptor, human corionic gonadotropin, colon-specific antigen-p (CSAp), insulin-like growth factor (ILGF), placental growth factor (PlGF), prostatic acid phosphatase, PSA, PSMA, T101, TAG, TAG-72, Her2/neu, carbonic anhydrase IX, IL-6, S100, alpha fetoprotein, A3, CA125, carcinoembryonic antigen (CEA), nonspecific cross-reacting antigens such as CD66 (a,b,c,d), MART-1, TRP-1, TRP-2, amyloid, and gplOO, formulated in a pharmaceutically acceptable vehicle.

As used herein a "pharmaceutical composition" refers to a composition including a drug wherein the carrier is a pharmaceutically acceptable carrier, while a "veterinary composition" is one wherein the carrier is a veterinarily acceptable carrier. The term "pharmaceutically acceptable carrier" or "veterinarily acceptable carrier" can include any medium or material that is not biologically or otherwise undesirable, i.e, the carrier may be administered to an organism along with a composition or compound of the present invention without causing any undesirable biological effects or interacting in a deleterious manner with the complex or any of its components or the organism. Examples of pharmaceutically acceptable reagents are provided in The United States Pharmacopeia, The National Formulary, United States Pharmacopeial Convention, Inc., Rockville, Md. 1990, hereby incorporated in its entirety by reference herein into the present application, as is *Pharmaceutical Dosage Forms & Drug Delivery Systems*, 7th Edition, Ansel et a/., editors, Lippincott Williams & Wilkins, 1999.

A drug (i.e., targetable construct or complex) can be included in the pharmaceutical composition in an amount sufficient to produce the desired effect upon the patient. The pharmaceutical compositions of the present invention can further comprise other chemical components, such as diluents and excipients. A "diluent" is a chemical compound diluted in a solvent, preferably an aqueous solvent, that facilitates dissolution of the drug in the solvent, and it may also serve to stabilize the biologically active form of the drug or one or more of its components. Salts dissolved in buffered solutions are utilized as diluents in the art. For example, preferred diluents are buffered solutions containing one or more different salts. A preferred buffered solution is phosphate buffered saline (particularly in conjunction with compositions intended for pharmaceutical administration), as it mimics the salt conditions of human blood. Since buffer-salts can control the pH of a solution at low concentrations, a buffered diluent rarely modifies the biological activity of a biologically active peptide.

In one embodiment of the present invention, the pharmaceutical compositions facilitate administration of humanized antibodies to an organism, preferably an animal, preferably a mammal. Particular mammals include bovine, canine, equine, feline, ovine, and porcine animals, and non-human primates. Humans are particularly preferred. Multiple techniques of administering or delivering a compound exist in the art include but are not limited to, oral, rectal (e.g., an enema or suppository) aerosol (e.g., for nasal or pulmonary delivery), parenteral (e.g., i.v., i.m., s.c.), and topical administration. Preferably, sufficient quantities of the composition or compound may be delivered to achieve the intended effect. The particular amount of composition or compound to be delivered will depend on many factors, including the effect to be achieved, the type of organism to which the composition is delivered, delivery route, dosage regimen, and the age, health, and sex of the organism. As such, the particular dosage of a composition or compound of embodiment disclosed herein in a given formulation is left to the ordinarily skilled artisan's discretion (e.g. the health provider's discretion).

Those skilled in the art will appreciate that when the pharmaceutical compositions of the present invention are administered as agents to achieve a particular desired biological result, which may include a therapeutic or protective effect(s) (including vaccination), it may be necessary to combine the composition or compounds disclosed herein with a suitable pharmaceutical carrier. The choice of pharmaceutical carrier and the preparation of the composition or compound as a therapeutic or protective agent will depend on the intended use and mode of administration. Suitable formulations and methods of administration of therapeutic agents include, but are not limited to, those for oral, pulmonary, nasal, buccal, ocular, dermal, rectal, or vaginal delivery.

Depending on the mode of delivery employed, the context-dependent functional entity can be delivered in a variety of pharmaceutically acceptable forms. For example, the context-dependent functional entity can be delivered in the form of a solid, solution, emulsion, dispersion, micelle, liposome, and the like, incorporated into a pill, capsule, tablet, suppository, areosol, droplet, or spray. Pills, tablets, suppositories, areosols, powders, droplets, and sprays may have complex, multilayer structures and have a large range of sizes. Aerosols, powders, droplets, and sprays may range from small (approximately 1 micron) to large (approximately 200 micron) in size.

Pharmaceutical compositions disclosed herein may be used in the form of a solid, a lyophilized powder, a solution, an emulsion, a dispersion, a micelle, a liposome, and the like, wherein the resulting composition contains one or more of the targetable constructs or complexes of embodiments of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Examples of a stabilizing dry agent includes triulose, preferably at concentrations of 0. 1% or greater (See, e.g., U.S. Pat. No. 5,314,695).

Although individual needs may vary, determination of optimal ranges for effective amounts of pharmaceutical compositions is within the skill of the art. Human doses may be extrapolated from animal studies (Katocs et al., Chapter 27 In: *Remington's Pharmaceutical Sciences*, 18th Ed., Gennaro, ed., Mack Publishing Co., Easton, Pa., 1990). Generally, the dosage required to provide an effective amount of a pharmaceutical composition, which may be adjusted by one skilled in the art, will vary depending on the age, health, physical condition, weight, type and extent of the disease or disorder of the recipient, frequency of treatment, the nature of concurrent therapy (if any) and the nature and scope of the desired effect(s). See, for example, Nies et al., Chapter 3 In: *Goodman & Oilman's The Pharmacological Basis of Therapeutics*, 9th Ed., Hardman et al., eds., McGraw-Hill, New York, N.Y., 1996).

Dosing of therapeutic compositions is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The term "patient" is intended to encompass animals (e.g., cats, dogs and horses) as well as humans. Persons of ordinary skill can easily determine optimum dosages, dosing methodologies and repetition rates. Optimum dosages may vary depending on the relative potency of individual therapeutic agents, and can generally be estimated based on ECso found to be effective in in vitro and in vivo animal models.

The range of doses (the amount of targetable construct or complex administered) is broad, since in general the efficacy of a therapeutic effect for different mammals varies widely with doses typically being 20, 30 or even 40 times smaller (per unit body weight) in man than in the rat. In general, dosage is from 0.01 µg to 100 mg per kg of body weight, preferably 0.01 µg to 10 mg/kg of body weight, 0.01 µg to 50 µg/kg of body weight, 0.01 µg to 100 mg/kg of body weight, 0.01 µg to 10 mg/kg of body weight, 0.01 µg to 1 mg/kg of body weight, 0.01 µg to 100 µg/kg of body weight, 0.01 µg to 10 µg/kg of body weight, 0.01 µg to 1 µg/kg of body weight, 0.01 µg to 10 µg/kg of body weight, 0.01 µg to 1 µg/kg of body weight, 0.01 µg to 0.1 µg/kg of body weight, and ranges based on the boundaries of the preceding ranges of concentrations. Thus, for example, the preceding description of dosages encompasses dosages within the range of 10 mg to 100 mg per kg of body weight, 1.0 mg to 100 mg/kg of body weight, 0.1 mg to 100 mg/kg of body weight, etc.

In one embodiment, doses may be given once or more daily, weekly, monthly or yearly, or even once every 2 to 5 or more years. Persons of ordinary skill in the art may estimate repetition rates for dosing based on measured residence times and concentrations of the targetable construct or complex in bodily fluids or tissues. Following successful treatment, it may be desirable to have the patient undergo maintenance therapy to prevent the recurrence of the disease state, wherein the therapeutic agent is administered in maintenance doses, ranging from 0.01 µg to 100 mg per kg of body weight, once or more daily, to once every 5 years.

In one embodiment, a particular dose may be calculated according to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data.

In one embodiment, an individual patient's dosage may be adjusted as the progress of the disease is monitored. Blood levels of the targetable construct or complex in a patient may be measured to see if the dosage needs to be adjusted to attain desired results.

In one example, pharmacogenomics may be used to determine which targetable constructs and/or complexes, and dosages thereof, are most likely to be effective for a given individual (Schmitz et al., *Clinica ChimicaActa* 308: 43-53, 2001; Steimer et al, *Clinica ChimicaActa* 308: 33-41, 2001).

Administration of the humanized antibodies disclosed herein may be parenteral, including intravenous, intraarterial, intraperitoneal, intramuscular, subcutaneous, intrapleural, intrathecal, intracavitary, by perfusion through a catheter or by direct intralesional injection. In accordance with this administration the antibodies may be administered once or more times daily, once or more times weekly, once or more times monthly, and once or more times annually.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

Embodiments illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present invention claimed. Thus, it should be understood that although the present invention has been specifically disclosed by preferred embodiments and optional features, modification and variations embodied herein disclosed may be resorted to by those skilled in the art, and that such modifications and variations are considered to be within the scope of this invention.

Embodiments of the present invention have been described broadly and generically herein. Each of the narrower species and subgeneric groupings falling within the generic disclosure may also form part of the invention. This includes the generic description herein with a proviso or negative limitation removing any subject matter from the genus, regardless of whether or not the excised material is specifically recited herein.

In addition, where features or aspects are described in terms of Markush groups, those skilled in the art will recognize that the embodiments also thereby described in terms of any individual member or subgroup of members of the Markush group.

The embodiments are further illustrated by the following examples and detailed protocols. However, the examples are merely intended to illustrate embodiments and are not to be construed to limit the scope herein. The contents of all references and published patents and patent applications cited throughout this application are hereby incorporated by reference.

EXAMPLES

Example 1

Construction of a Humanized L243 Antibody

Molecular Cloning of L243 Vk and VH Genes

In one exemplary method, the hybridoma cell clone producing the mAb mL243 was cultured in HSFM medium (Life Technologies, Inc.,) supplemented with 10% FBS (Hyclone). The genes encoding the VK (VK1BACK/CK3') and VH (VH1BACK/VH1FOR) of mL243 were cloned by RT-PCR and the sequences were determined by DNA sequencing. Multiple independent clones were sequenced to eliminate possible errors resulting from the PCR reaction. Sequence design of hL243 V genes In one example, by searching the human VK and VH sequences in the Kabat database, the FRs of mL243 VK and VH were found to exhibit the highest degree of sequence homology to human REI VK and RF-TS3 VH, respectively. One exception is the FR4 of mL243VH, which showed the highest sequence homology with that of NEWM VH. Therefore, in one example human REI framework sequences were used as the scaffold for grafting the CDRs of mL243VK (FIG. 5), and a combination of RF-TS3 and NEWM framework sequences were used for hL243Vn (FIG. 6). In fact, hL243 VH has the same human VH frameworks as that of another humanized Ab, hRS7 (Govindan et al, Breast Cancer Res. Treat. 84,173-182, 2004). There are a number of amino acid changes in each chain outside of the CDR regions when compared to the starting human antibody frameworks. Several amino acid residues in murine FRs that flank the putative CDRs were maintained in the reshaped hL243 Fv based on the guideline previously established (Qu et al., Clin. Cancer Res. (1999) 5 3095s-3100s). These residues are R37, K39, V48, F49, and G100 of mL243Vk and F27, K38, K46, A68, and F91 of mL243VH (FIG. 3 and 4 respectively). Also see SEQ. ID. 3 and 4 respectively for the sequence of hL243 VL and hL243VH respectively.

Construction of hL243 V Sequences

A modified strategy as described by Leung et al. (Mol. Immunol. (1995) 32 1413-1427) was used to construct the designed VK and VH genes for hL243 using a combination of long oligonucleotide systheses and PCR as illustrated in FIG. 4. For the construction of the hL243 VH domain, two long oligonucleotides, hL243VHA (175-mer) and hL243VHB (168-mer) were synthesized on an automated DNA synthesizer (Applied Biosystem).

hL243VHA represents nt 23 to 197 of the HL243VH domain.
5'-GGTCTGAGTT GAAGAAGCCT GGGGCCTCAG TGAAGGTTTC CTGCAAGGCT TCTGGATTTA CCT-TCACAAA CTATGGAATG AACTGGGTGA AGCAG-GCCCC TGGACAAGGG CTTAAGTGGA TGGGCTG-GAT AAACACCTAC ACTAGAGAGC CAA CATATGCTGATGACTTCAAGGG-3' (SEQ ID NO:16)
hL243VHB represents the minus strand of the hL243VH domain complementary to nt 176 to 343.
5'-ACCCTTGGCC CCAGTAGTCA AAACCCGTAG GTA-CAACCGC AGTAATATCT CTTGCACAGA AATA-CACGGC AGTGTCGTCA GCCTTTAGGC TGCT-GATCTG GAGATATGCC GTGCTGACAG AGGTGTCCAA GGAGAAGGCA AACCGT CCCTTGAAGTCATCAGCATATG-3' (SEQ Id NO:17)

The 3'-terminal sequences (22 nt residues) of hL243VHA and B are complementary to each other, as underlined in above sequences. In one example, under defined PCR conditions, 3'-ends of hL243VHA and B anneal to form a short double stranded DNA flanked by the rest of the long oligonucleotides. Each annealed end serves as a primer for the replication of the single stranded DNA in a PCR reaction, resulting in a double strand DNA composed of the nt 23 to 343 of hL243VH. This DNA was further amplified in the presence of a short oligonucleotide primer pair, hRS7VHBACK and hL243VHFOR, to form the full-length hL243VH. Because of the sequence identity between hRS7VH and hL243VH in is region, hRS7VHBACK, previously designed and used for hRS7 Ab, was used here.

hRS7VHBACK
(SEQ ID NO:18)
5'-GTGGTGCTGC AGCAATCTGG GTCTGAGTTG AAGAAGCC-3' hL243VHFOR
(SEQ ID NO:19)
5'-TGAGGAGACG GTGACCAGGG ACCCTTGGCC CCAGTAGT-3'

In this example a minimum amount of hL243VHA and B (determined empirically) was amplified in the presence of 10 ul of 10× PCR Buffer (500 mM KCl 100 mM Tris.HCL buffer, pH 8.3, 15 mM MgCl$_2$), 2 umol of hRS7VHBACK and hL243VHFOR, and 2.5 units of Taq DNA polymerase (Perkin Elmer Cetus, Norwalk, Conn.). This reaction mixture was subjected to 3 cycle of PCR reaction consisting of denaturation at 94° C. for 1 minute, annealing at 45° C. for 1 minute, and polymerization at 72° C. for 1.5 minutes, and followed by 27 cycles of PCR reaction consisting of denaturation at 94° C. for 1 minute, annealing at 55° C. for 1 minute, and polymerization at 72° C. for 1 minute. Double-stranded PCR-amplified product for hL243VH was gel-purified,restriction-digested with PstI and BstEII and cloned into the complementary PstI/BstEII sites of the heavy chain staging vector, VHpBS4.

In one example, for constructing the full length DNA of the humanized VK sequence, hL243 VKA (155-mer) and hL243VKB (155-mer) were synthesized as described above. hL243VKA and B were amplified by two short oligonucleotides hlmmu31VKBACK and hlmmu31VKFOR as described above. hlmmuS 1VKBACK and hlmmuS1 VKFOR were designed and used previously for a humanized anti-AFP Ab (Qu et al, Clin. Cancer Res. (1999) 5 3095-3100).

hL243VKA represents nt 21 to 175 of the hL243VD domain.
5'-TCCATCATCT CTGAGCGCAT CTGTTGGAGA TAGGGTCACT ATCACTTGTC GAGCAAGTGA GAATATTTAC AGTAATTTAG CATGGTATCG TCA-GAAACCA GGGAAAGCAC CTAAACTGCT GGTCTTTGCT GCATCAAACT TAGCAGATGG TGTGC-3' (SEQ ID NO:20)

hL243VKB represents the minus strand of the hL243VK domain complementary to nt 154 to 312.

(SEQ ID NO:21)
5'-CAGCTTGGTC CCTCCACCGA ACGCCCACGG AGTAGTCCAA
AAATGTTGAC AATAATATGT TGCAATGTCT TCTGGTTGAA
GAGAGCTGAT GGTGAAAGTA TAATCTGTCC CAGATCCGCT
GCCAGAGAAT CGCGAAGGCA CACCATCTGC TAAGTTTGA-3' hImmu31VKBACK
(SEQ ID NO:22)
5'-GACATTCAGC TGACCCAGTC TCCATCATCT CTGAGCGC-3' hImmu31VKFOR
(SEQ ID NO:23)
5'-CCGGCAGATC TGCAGCTTGG TCCCTCCACC G-3'

Gel-purified PCR products for hL243VK in this example were restriction-digested with PvuII and BglHI and cloned into the complementary PvuI/BclI sites of the light chain staging vector, VKpBR2. The final expression vector hL243pdHL2 was constructed by sequentially subcloning the XbaI-BamHI and XhoI/NotI fragments of hL243Vic and VH, respectively, into pdHL2 as described above.

Construction of the Expression Vectors for hL243 Antibodies

In one example, a final expression vector hL243pdHL2 was constructed by sequentially subcloning the XbaI-BamHI and XhoI/NotI fragments of hL243Vx and VH, respectively, into pdHL2 as described previously (Losman et al. *Cancer,* 80:2660 (1997)). The expression vector pdHL2, as described by Gilles et al. (*J. Immunol. Methods* 125:191 (1989), contains the genomic sequence of the human γl chain, therefore, the hL243 is an IgG1/K isotype.

In one exemplary method, to construct the expression vector for hL243 of other isotype, such as IgG4/K, the genomic sequence of human γ1 chain was replaced with that of γ4 chain, which was obtained by PCR amplification. The template used was the genomic DNA extracted from ATCC CRL-11397 cell and the primer pair was P-SacII (5'-CCGCGGT-CACATGGCACCA CCTCTCTTGCAGCTTCCACCA AGGGCCC-3') (SEQ ID NO:24) and P-EagI (5'-CCGGC-CGTCG CACTCAT TTA CCCAGAGACA GGG-3') (SEQ ID NO:25) The amplified PCR product was cloned into TOPO-TA sequencing vector (Invitrogen) and the sequence was confirmed by DNA sequencing.

A point mutation, Ser241 Pro (based on Kabat numbering) was introduced into the hinge region of the γ4 sequence to avoid formation of half-molecules when the IgG4 Ab is expressed in mammalian cell cultures (Schuurman et al, *Mol. Immunol.* 38:1 (2001)). The human γ4 hinge region sequence between PstI and StuI restriction sites (56 bp) was replaced with a synthetic DNA fragment with substitution of the TCA codon for Ser241 to CCG for Pro. The human γ1 genomic sequence in hL243pdHL2 was substituted with the mutated γ4 sequence, resulting in the final expression vector, designated as hL243γ4PpdHL2, for the IgG4 isotype hL243.

Transfection and Expression of hL243 Antibodies

In one exemplary method, approximately 30 µg of the expression vector for hL243 or hL243γ4P was linearized by digestion with SaiI and transfected into Sp2/0-Ag14 cells by electroporation (450V and 25 uF). The transfected cells were plated into 96-well plates for 2 days and then selected for drug-resistance by adding MTX into the medium at a final concentration of 0.025 pM. MTX-resistant colonies emerged in the wells 2-3 weeks. Supernatants from colonies surviving selection were screened for human Ab secretion by ELISA assay. Briefly, 100 ul supernatants were added into the wells of a microtiter plate precoated with GAH-IgG, F(ab')2 fragment-specific Ab and incubated for 1 h at room temperature. Unbound proteins were removed by washing three times with wash buffer (PBS containing 0.05% polysorbate 20). HRP-conjugated GAH-IgG, Fc fragment-specific Ab was added to the wells. Following an incubation of 1 h, the plate was washed. The bound HRP-conjugated Ab was revealed by reading $A_{490}$ nm after the addition of a substrate solution containing 4 mM OPD and 0.04% $H_2O_2$. Positive cell clones were expanded and hL243 and hL243γ4P were purified from cell culture supernatant by affinity chromatography on a Protein A column.

The Ag-binding Specificity of hL243.

In one example, Ag-binding activity and specificity of HL243 was shown by a cell surface binding assay. Raji cells were incubated in PBS/BSA (1%) containing saturate concentration of purified hL243 (20 µg/ml) for 1 h at 4° C. After washing, cell surface-bound hL243 was detected by incubating the Raji cells in the buffer containing a PE-conjugated $2^{nd}$ antibody (goat anti-human IgG, Fc fragment specific) and counting in a Guave PCA system (Guava Technologies, Inc., Hayword, Calif.). As shown in FIG. 7, hL243 bound to an antigen on Raji cells recognized by mL243 because the binding is specifically blocked by preincubation of the cells with mL243, indicating the Ag-binding specificity of mL243 is preserved in the humanized version.

The Ag-binding Activity of hL243γ4P.

In one exemplary method, a competition cell-binding assay was carried out to assess the immunoreactivity of hL243γ4P relative to the parent mL243. A constant amount of $^{125}$I-labeled murine L243 or hL243γ4P (100,000 cpm, ~10 uCi/ug) was incubated with human lymphoma cells (Raji, Daudi or Ramos) in the presence of varying concentrations (0.2-700 nM) of purified hL243γ4P or murine L243 at 4° C. for 1-2 h. Unbound Abs were removed by washing the cells in PBS. The radioactivity associated with cells was determined after washing. As shown in FIG. 8, murine L243 and hL243γ4P mAbs competed with each other for the binding to the cell surface antigen, indicating they recognize same antigenic determinant. hL243γ4P showed an apparent ~2-fold stronger binding avidity than mL243 because it competed better than mL243 (ECso of ~7 vs. ~16.5 nM).

Figure 9:
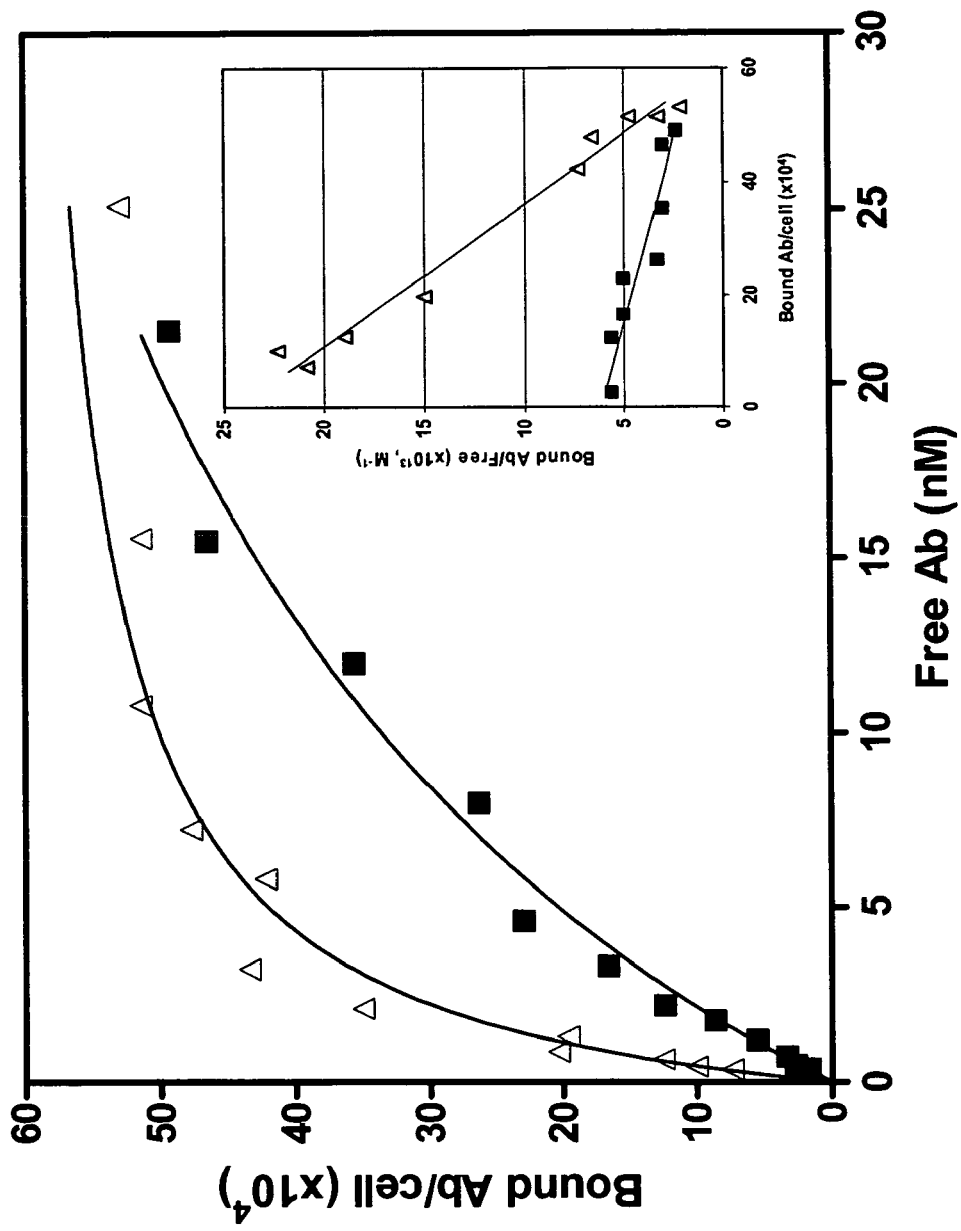
FIG. 9 illustrates an exemplary Ag-binding affinities of hL243γ4P and mL243 determinated by direct cell surface saturation binding and Scachard plot analysis. Varying concentrations of $^{125}$I-labeled mL234 (>>) or hL243γ4P (A) were incubated with 2×10$^5$ Daudi human lymphoma cells at 4° C. for 2 h, and unbound radioactivity was removed from cell suspensions by washing. The cell-associated radioactivity was counted, specific binding of radiolabeled antibody to the cell surface antigen calculated, and Scatchard plot analysis was then applied to determine the maximum number of binding sites per cell and the apparent antigen-binding affinity constant: The maximum binding of mL234 or hL243γ4P to Daudi cell surface was 6×10$^6$ molecules/cell; The dissociation constants determined for mL234 or hL243γ4P were 14 and 2.6 nM, respectively.

The antigen-binding affinity constant of hL243γ4P was determined by direct cell surface binding assay of the radio-labeled antibodies and Scatchard plot analysis. To measure specific cell surface antigen binding, two sets of cells were prepared and used in the binding assay to estimate the non-specific and total binding of radioactivities, respectively. The cells for non-specific binding were pre-incubated with excess amount of unlabled Ab to block all surface antigen sites prior to adding the radiolabeled antibody, while those for total binding were pre-incubated in PBS. After pre-incubation, varying amounts of either $^{125}$I-hL243γ4P or $^{125}$I-mL243 were added and incubated with $2 \times 10^5$ human lymphoma cells (Raji, Daudi or Ramos) at 4° C. for 2 h and unbound antibodies were removed by washing. The cell-associated radioactivity was counted. The specific cell surface binding of the radiolabeled antibody at a given concentration of radiolabeled antibody was calculated as: the counts of total binding subtracts the counts of non-specific binding. Scatchard plot analysis was then performed to determine the maximum number of hL243γ4P and mL243 binding sites per cell and the apparent dissociation constants of the equilibrium binding. As shown in FIG. 9, the maximum binding of hL243γ4P and mL243 to Daudi cells was virtually same, ~6×1 $O^5$ molecules/cell, indicating they bound to the same Ag. The apparent dissociation constant values for hL243γ4P and mL243 were calculated to be 2.6 and 14 nM, respectively. Similar results were obtained with Raji and Ramos cells (data not shown).

Example 2 hL243γ4P Functional Studies

In one exemplary method in vitro cell-based studies were conducted to determine whether hL243γ4P had retained its antiproliferative effect and whether effector cell and complement binding functions have been abrogated. In this example study described below indicate that the antiproliferative effect had been maintained, while effector cell and complement binding functions had been abrogated.

Effector Cell Assay

The goal of replacing the Fc region of hL243 with an IgG4 isotype Fc region was to abrogate effector cell functions through Fcγ-receptor and complement-binding. CDC and ADCC assays were performed to assess these functions by hL243γ4P.

CDC

Daudi cells were incubated with serial dilutions of the antibodies hL243, hL243γ4P, hA20 (as another positive control) and hMN14 (negative control) in the presence of human complement for 2 h. This was followed by the addition of resazurin to assess cell viability. Both untreated and maximum lysis controls were included. Fluorescence readings were obtained 5 hours after resazurin addition. The fluorescence level obtained is directly correlated to the amount of viable cells. % viable cells was calculated by the formula (Test−maximum lysis)/(untreated control−maximum lysis)× 100. The results indicate that hL243γ4P does not produce any complement-mediated cytotoxic effect on cells compared to hL243 ($EC_{50}$=2.6 nM) and hA20 ($EC_{50}$=0.66 nM). See FIG. 10.

ADCC

Figure 11:
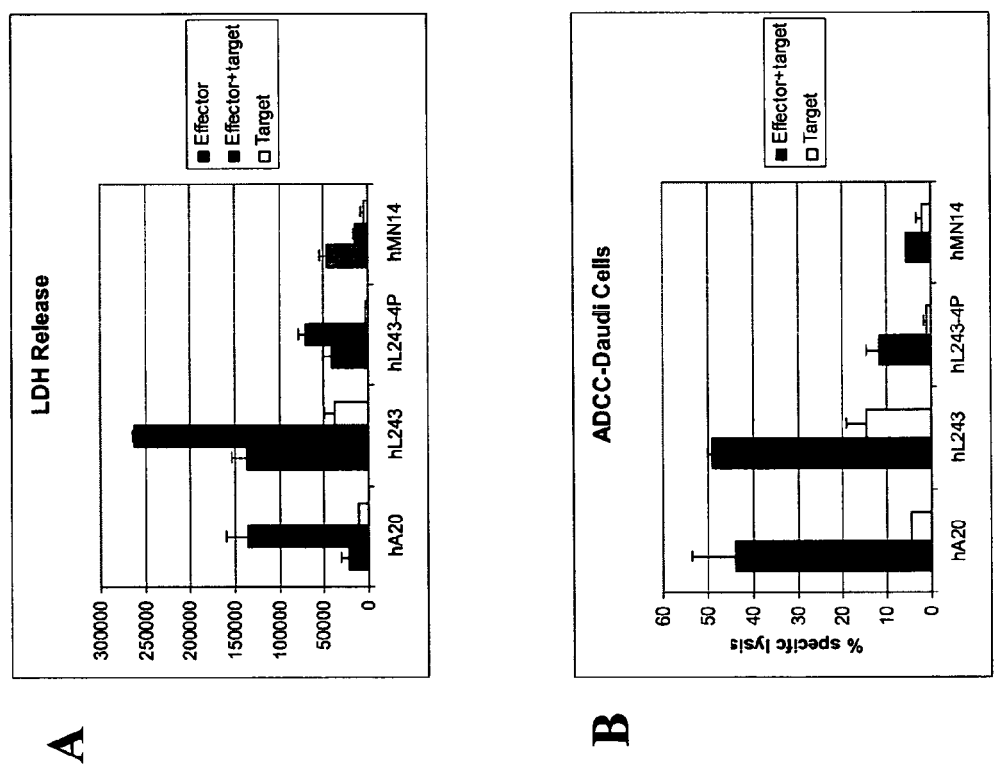
FIGS. 11A and 11B illustrate an exemplary LDH release (FIG. 11A) and % cell lysis (FIG. 11B) by ADCC as observed for hL243, hL243γ4P, hA20 (positive control) and 1 hMN-14 (negative control).

Daudi cells were incubated with hA20, hL243, hL243γ4P and hMN-14 at 5 μg/ml. Effector cells were added at a ratio of 50:1 After 4 hours cell lysis was assayed by LDH release (FIG. 11A) and cell lysis (FIG. 1 IB).

In these results where the effects of antibody alone on effector cells are shown it can be seen that the KL243 induced significant lysis of effector cells while hL243γ4P did not. When the specifc lysis figures are corrected for the effect on effector cells hL243γ4P shows much reduced lysis of target cells compared to hL243 (12% vs 48%).

In Vitro Proliferation Assays

A multiplex colorimetric assays utilizing both MTS bioreduction (for determination of the number of viable cells) and BrdU (for quantification of cell proliferation based on the measurement of BrdU incorporation during DNA synthesis) were performed. Daudi and Raji cells were incubated with serial dilutions of hL243γ4P for 2 and 3 days. mL243 and hMN-14 were used as positive and negative controls respectively. After incubation, BrdU and MTS assays were performed. Results of the MTS assays are shown below. BrdU assays gave similar results.

Figure 12:
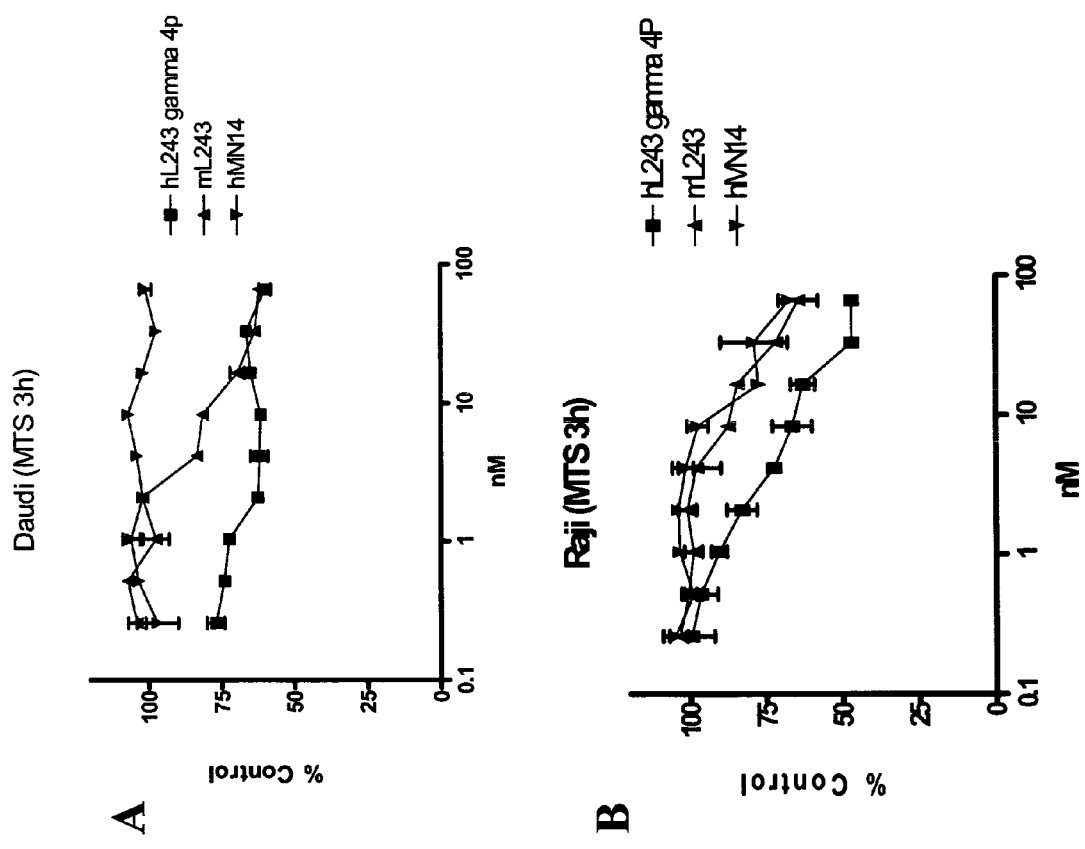
FIGS. 12A and 12B illustrate an exemplary in vitro proliferative assays on Daudi (FIG. 12A) and Raji (FIG. 12A) cell lines at the end of 2 days.
Figure 13:
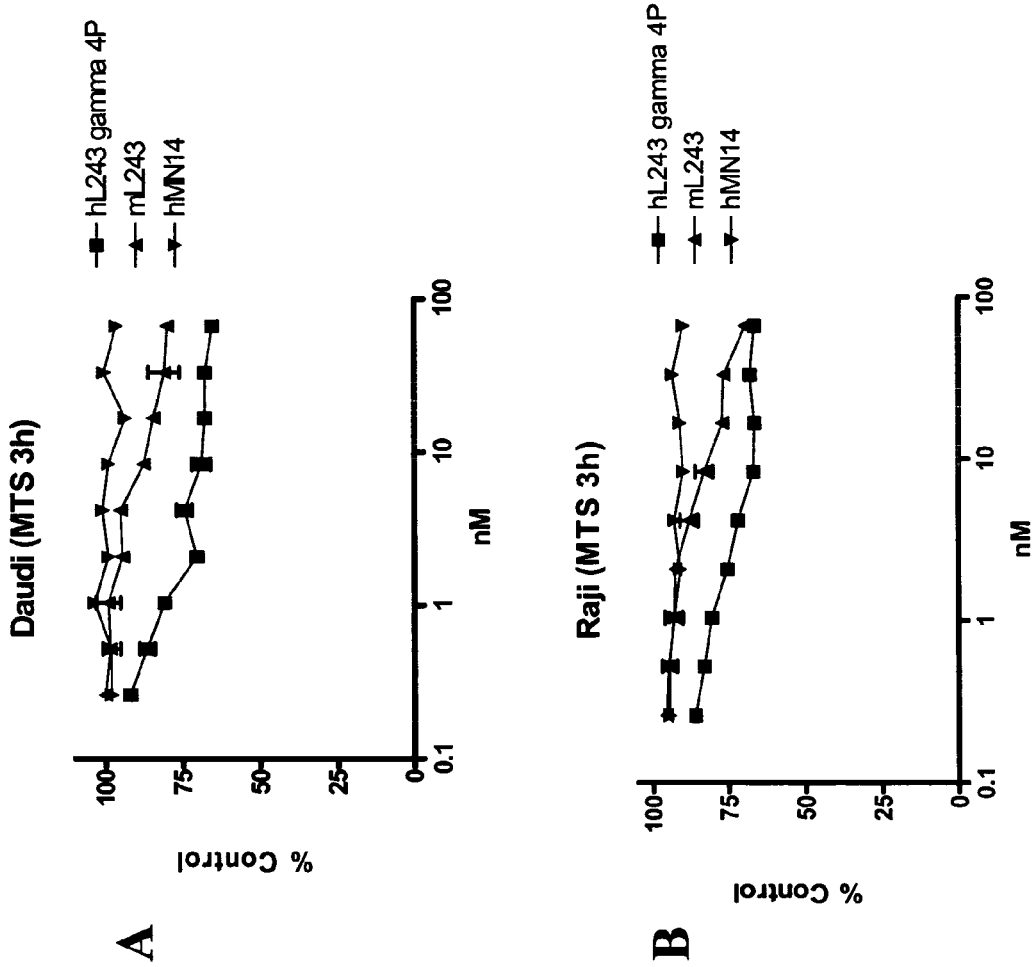
FIGS. 13A and 13B illustrate an exemplary in vitro proliferative assays on Daudi (FIG. 13A) and Raji (FIG. 13B) cell lines at the end of 3 days.

In one exemplary method, multiplex calorimetric assays utilizing both MTS bioreduction (for determination of the number of viable cells) and BrdU (for quantification of cell proliferation based on the measurement of BrdU incorporation during DNA synthesis) were performed. Daudi and Raji cells were incubated with serial dilutions of hL243γ4P for 2 and 3 days. Murine L243 and hMN14 were used as positive and negative controls, respectively. After incubation, BrdU and MTS assays were performed. Results of the MTS assays are shown in FIGS. 12 and 13. BRDU assays gave similar results (not shown). These results indicate hL243γ4P inhibits proliferation of Raji and Daudi cell lines. However in similar experiments in the EBV negative cell line Ramos, inhibition of proliferation was only observed in the presence of a crosslinking anti Fc $(Fab)_2$.

Example 3

Comparison of in Vivo Efficacy of hL243γ4P and mL243 (IgG2a) in a Xenograft Model of Human Non-Hodgkin's Lymphoma In one exemplary method, a therapeutic study was performed to compare the in vivo efficacy of humanized L243-IgG4 and murine L243-IgG2a monoclonal antibody isotypes, in a xenograft model of human non-Hodgkin's lymphoma (Raji). Prior In vitro studies have shown that replacing the Fc region of L243-IgG1 with an IgG4 isotype abrogates the effector cell functions of the antibody (ADCC and CDC), while retaining the antiproliferative effects. Prior studies using fully human anti-HLA-DR antibodies engineered as an IgG4 isotype have also been shown to minimize side effects due to Fc-portion-mediated effector functions while providing excellent tumoricidal activity in vitro, and in vivo in xenograft models of non-Hodgkins lymphoma and animal models (cynomologus monkeys) with no long-lasting hematological effects. See Nagy et al., Nature Medicine, 8:801 (2002). Thus, this study aimed to determine if hL243-IgG4 could maintain significant antitumor efficacy in a xenograft model. In the absence of sufficient quantity of hL243-IgG1, mL243 IgG2a was used (murine IgG2a is the equivalent of human IgG1 in complement fixation, and effecting ADCC).

Figure 14:
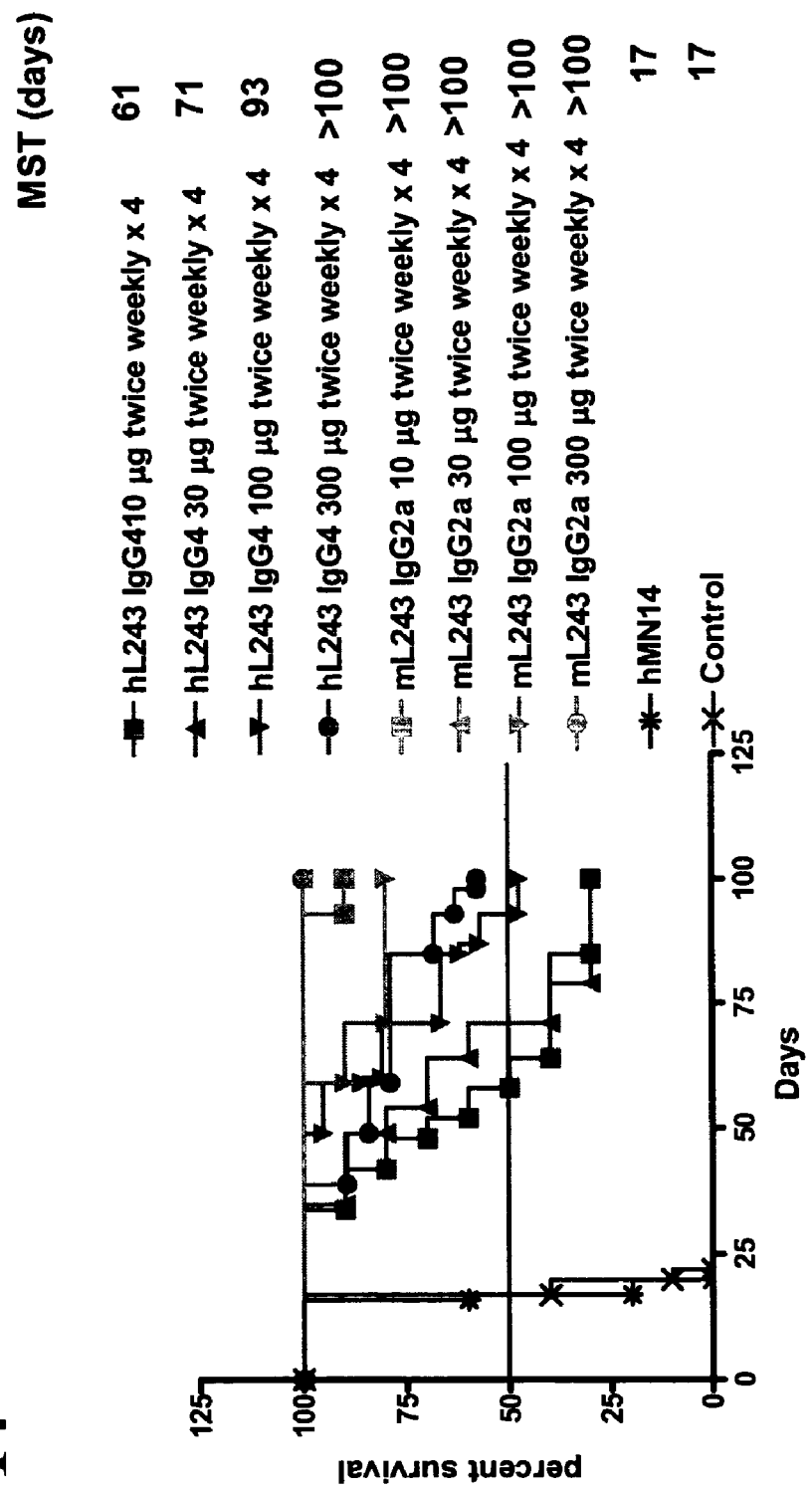
FIG. 14 illustrates an exemplary median survival times for tumor-bearing SCID mice injected with hL243γ4P.

SCID mice were injected with 2.5 million Raji cells. Therapy with hL243-IgG4 or mL243-IgG2a was initiated 1 daypost tumor cell administration. Both groups of mice injected with saline or with non-specific control antibody, hMN-14, had a median survival time (MST) of 17 days. All the groups of mice treated with either humanized or murine L243 had significantly improved life span compared to mice injected with saline or hMN-14 (PO.0001). Treatment with various doses of hL243 IgG4 resulted in a dose-response relationship, with mice receiving higher doses having better survival times. In the group of animals treated with various doses of mL243 IgG2a, the cure rate was in the range of 80-100%. See FIG. 14.

This study showed the concurrent retention of antitumor efficacy and removal of complement binding activity of the IgG4 construct of L243. Although, this study was performed in mice, significant therapeutic benefits using the aforementioned constructs may be achieved in all mammals suffering from autoimmune diseases, lymphomas, or leukemias. In particular, the aforementioned constructs can effectively be used in (i) domestic animals, especially cats, dogs, and horses, to treat autoimmune diseases and lymphomas/leukemias; and (ii) humans, for the treatment of autoimmune diseases, lymphomas, and leukemias, as well as immune dysregulatory, metabolic, and neurodegenerative diseases involving HLA-DR expression.

Example 4

In Vitro Comparison of hL243 with L243 and anti-B Cell MAbs in the Treatment of Human and Canine Lymphomas A 0.5 mg sample of hL243 (IgG4 isotype) was tested for reactivity with lymphoma cell lines and a dog B-cell lymphoma aspirate in comparison to the murine L243 as well as in comparison to other anti-B cell MAbs. Two functional studies were also done. The ability of the hL243 to induce apoptosis in the dog lymphoma aspirate was determined, and the anti-proliferative activity of the hL243 was tested against Namalwa, a human lymphoma cell line reported to be resistant to rituximab.

The binding of humanized or chimeric MAbs on human B-cell lymphomas were measured by flow cytometry using a Fluorescence-Activated Cell Sorter (FACS) in which the following MAbs-hMN-14, hLL 1, hLL2, hA20, Rituxan, and hL243 were stained with FITC goat anti-human(GAH) IgG Fc. The cell lines chosen were Namalwa (a rituximab resistant human B-cell lymphoma cell lin), SU-DHL-6 (a human B-cell non-Hodgkin lymphoma), WSU-FSCCL (an EBV-negative low-grade human B-cell lymphoma cell line), Raji, Daudi, and Ramos cells: As shown in Table 2, hL243 bound to all the aforementioned cell lines. In particular, hL243 bound to the Namalwa cells that are CD20-unresponsive, showing greater binding than other humanized MAbs. See Table 1. Furthermore, hL243 demonstrated anti-proliferative activity in the rituximab resistant human B-cell lymphoma cell line, Namalwa, as measured by a 3-H-thymidine uptake assay. The other CD20 antibody, humanized A20 (hA20), developed by Immunomedics, Inc., showed similar results to rituximab, a chimeric anti-CD20 known as Rituxan®. See Stein et al. (2004) Clin. Cancer Res. 10: 2868-2878.

Figure 16:
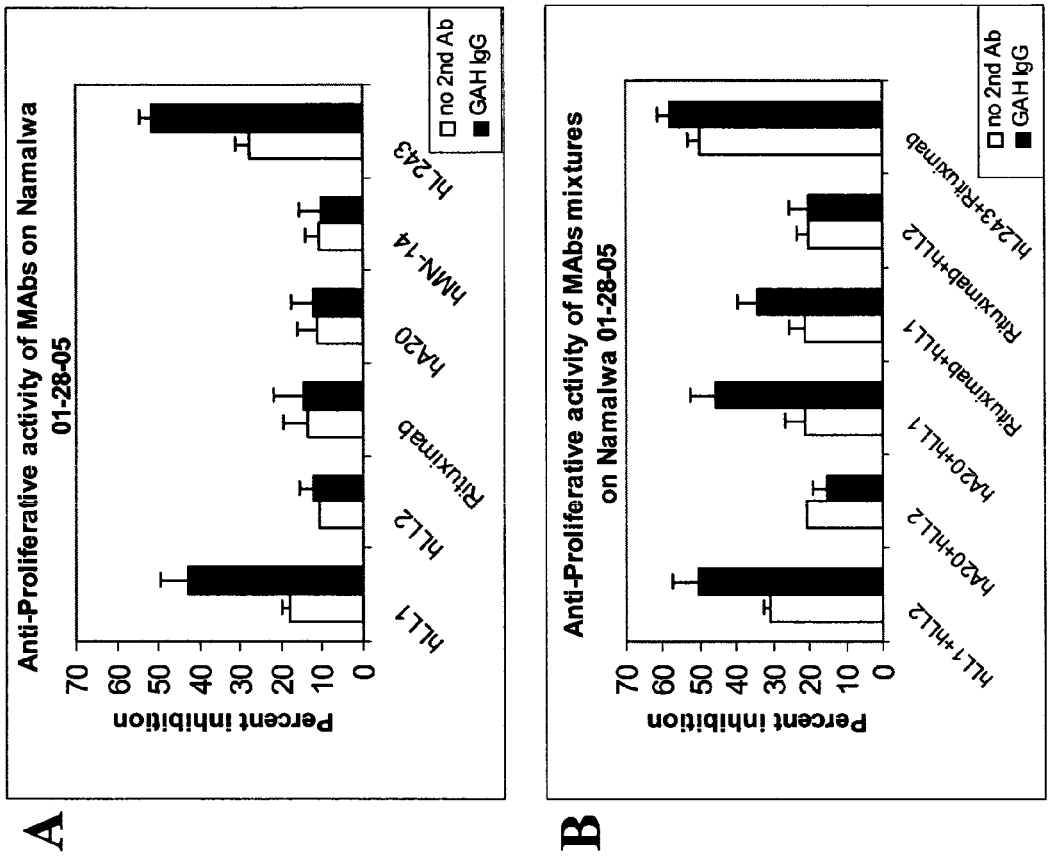
FIGS. 16A and 16B illustrate an exemplary anti-proliferative effects of humanized antibodies (hLL1, hLL2, Rituximab, hA20, hMN-14 and hL243 (IgG4 isotype), with and without goat anti-human IgG (GAH)) on Namalwa human B-cell lymphoma cell line as determined by a $^3$H-thymidine uptake assay.

As shown in FIG. 16A-B, the hL243 yielded 28% inhibition of proliferation when given alone; this was increased to 51% when hL243 was given in combination with anti-human IgG second antibody. When used in combination with rituximab the activity was increased to a level greater than that of either MAb alone. See FIG. 16-B.

Figure 15:
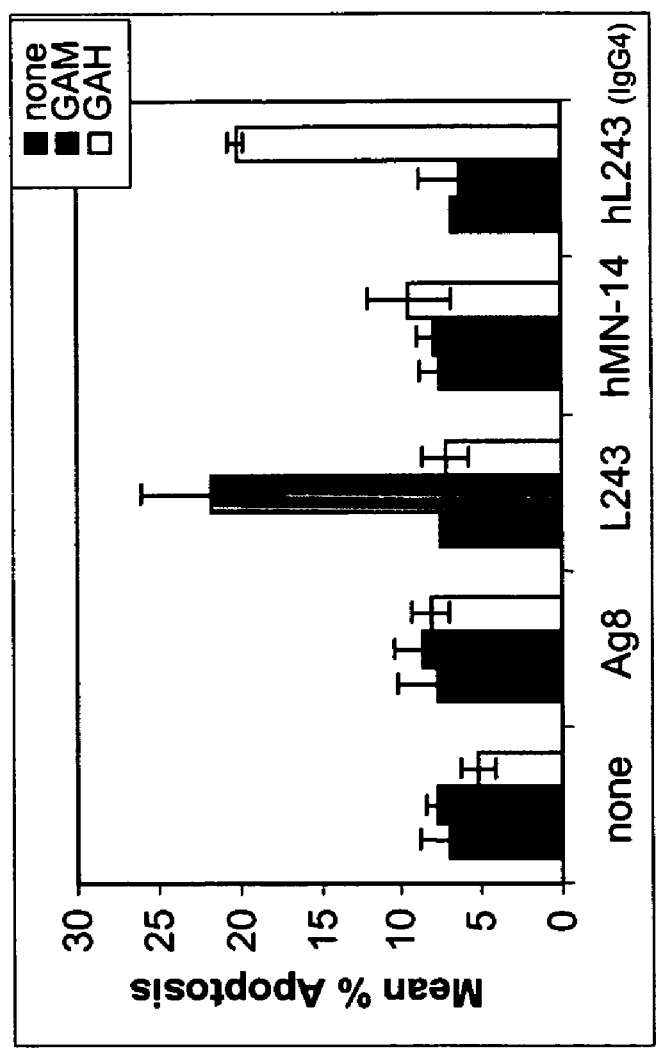
FIG. 15 illustrates an exemplary comparative induction of apoptosis in dog lymphoma cells (measured as % cells with a sub G0/G1 phase DNA content) caused by L243, hL243 (IgG4 isotype), hMN-14 (humanized MN-14 IgG), and Ag8 (murine myeloma derived mAb). L243 and hL243 caused apoptosis when crosslinked with goat anti-mouse (GAM) and goat-anti human (GAH) antibodies respectively.

The studies also demonstrated that hL243 has a greater binding affinity to the dog lymphoma cells than other humanized MAbs. See Table 3. In addition, KL243 was able to induce apoptosis in the dog lymphoma cells when crosslinked with an anti-human IgG second antibody, measured as % cells with a sub G0/G1 phase DNA content. See FIG. 15.

Example 5 hL243 Antibody Combinations and Their Effects
Methods

Antibodies

In one exemplary method, the hybridoma cell clone producing the anti-HLA-DR monoclonal antibody, L243, was obtained from ATCC (ATCC number HB-55). Cells were cultured in HSFM medium (Life Technologies, Inc. ) supplemented with 10% FBS (Hyclone). The genes encoding the Vκ and VH genes of L243 were cloned by RT-PCR. The humanized L243 (IgG1/κ isotype), hL243γ1, was generated similarly, as described previously (Leung et al., Hybridoma 13:469 (1994); Leung et al., Mol. Immunol. 32:1413 (1995); Stein et al., Blood 104:3705 (2004); Govindan et al., Breast Cancer Res. Treat. 84:173 (2004)).

The IgG4/κ isotype of hL243, hL243γ4p, can be constructed by replacing the heavy chain constant region coding sequence for the human γ1 chain with that of γ4 chain. A point mutation, Ser241 Pro (based on Kabat numbering) was introduced into the hinge region of the γ4 sequence in order to avoid formation of half-molecules when the antibody is expressed and produced in mammalian cell cultures (Schuurman et al. Mol Immunol. 38:1 (2001)). Other MAbs used in the studies were rituximab, purchased from for example IDEC Pharmaceuticals Corp. (San Diego, Calif.), and hMN-14, or labetuzumab (humanized anti-carcinoembryonic antigen IgG1), provided by Immunomedics, Inc. The construction and characterization of hMN-14, used here as a negative isotype control, have been described previously.

Cells

Exemplary cell lines were used in several studies. For example, the Burkitt lymphoma lines, Daudi, Raji, and Ramos, were purchased from the American Type Culture Collection (Manassas, Va.). Non-Burkitt lymphoma cell lines were obtained as follows. RL and SU-DHL-6, which contain the chromosomal translocation t(14;18), were obtained from Dr. John Gribben (Dana-Farber Cancer Institute, Boston, Mass.) and Dr. Alan Epstein (University of Southern California, Los Angeles, Calif.), respectively. Cell lines SU-DHL-4, SU-DHL-10, and Karpas422 were provided by Dr. Myron Czuczman (Roswell Park Cancer Institute, Buffalo, N.Y.), and WSU-FCCL and DoHH2 cell lines were obtained from Dr. Mitchell Smith (Fox Chase Cancer Center, Philadelphia, Pa.). The cells were grown as suspension cultures in DMEM (Life Technologies, Gaithersburg, Md.), supplemented with 10% fetal bovine serum, penicillin (100 U/ml), streptomycin (100 μg/ml), and L-glutamine (2 mM) (complete media).

The Antigen-binding Specificity of hL243 MAbs

Antigen-binding activity and specificity of hL243γ1 was shown by a cell surface binding assay. Raji cells were incubated in PBS/BSA (1%) containing a saturating concentration of purified hL243 (20 μg/ml) for 1 h at 4° C. After washing, cell surface-bound hL243γ1 was detected by incubating the Raji cells in the buffer containing a PE-conjugated 2nd antibody (goat anti-human IgG, Fc fragment specific) and counting in for example, a Guave PCA system (Guava Technologies, Inc., Hayward, Calif.).

A competition cell-binding assay was carried out to assess the reactivity of hL243γ4P relative to the parent mL243. A constant amount of $^{125}$I-labeled murine L243 or hL243γ4P (100,000 cpm, ~10 μCi/μg) was incubated with human lymphoma cells (Raji, Daudi or Ramos) in the presence of varying concentrations (0.2-700 nM) of purified hL243γ4P or murine L243 at 4° C. for 1-2 h. Unbound MAbs were removed by washing the cells in PBS. The radioactivity associated with cells was determined after washing.

In one example, the antigen-binding affinity constant of hL243γ4P was determined by direct cell surface binding assay of the radiolabeled antibodies and Scatchard plot analysis. To measure cell surface antigen binding, two sets of cells were prepared and used in the binding assay to estimate the non-specific and total binding of radioactivities, respectively. The cells for non-specific binding were pre-incubated with excess amount of unlabeled MAb to block all surface antigen sites prior to adding the radiolabeled antibody, while those for total binding were pre-incubated in PBS. After pre-incubation, varying amounts of either $^{125}$I-hL243γ4P or $^{125}$I-mL243were added and incubated with $2 \times 10^5$ human lymphoma cells (Raji, Daudi or Ramos) at 4° C. for 2 h and unbound antibodies were removed by washing. The cell-associated radioactivity was counted. The specific cell surface binding of the radiolabeled antibody at a given concentration of radiolabeled antibody was calculated as: the counts of total binding subtracts the counts of non-specific binding.

Flow Cytometric Assays.

Immunophenotyping: Indirect immunofluorescence assays were performed with the panel of cell lines described above, using FITC-goat anti-human IgG (Tago, Inc., Burlingame, Calif.) essentially as described previously, and analyzed by flow cytometry using a FACSCaliber (Becton Dickinson, San Jose, Calif.).

Example Analysis of apoptosis: Flow cytometric analysis of cellular DNA was performed following propidium iodide staining. Cells were placed in 24-well plates ($5 \times 10^5$ cells/well) and subsequently treated with MAbs (5 μg/ml). Three wells were prepared with each MAb to study the effects of crosslinking with goat anti-mouse or goat anti-human second antibodies. Following a 20-min incubation with the primary MAbs (37° C., 5% $CO_2$), F(ab')$_2$ goat anti-mouse IgG Fcγ-specific second antibody (Jackson Laboratories, West Grove, Pa.) was added to one well from each primary MAb to adjust the second antibody concentration to 20 pg/ml. F(ab')$_2$ goat anti-human IgG Fcγ-specific (Jackson Laboratories) was similarly added to the second well from each primary MAb, and the volume of the third set was equalized by addition of medium. Following a 48-h incubation (37° C., 5% $CO_2$), cells were transferred to test tubes, washed with PBS, and then resuspended in hypotonic propidium iodide solution (50 mg/ml propidium iodide in 0.1% sodium citrate, 0.1% Triton X-100). Samples were analyzed by flow cytometry using a FACSCaliber. Percent apoptotic cells was defined as the percent of cells with DNA staining before G0/G1 peak (hypodiploid).

Construction and Characterization of hL243.

Figure 17:
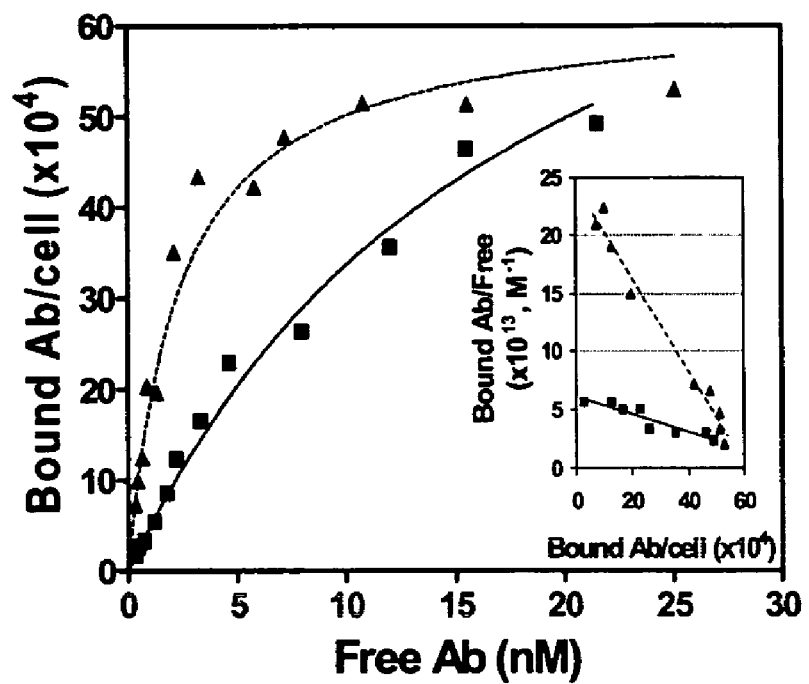
FIG. 17 illustrates binding characteristics of hL243γ4P relative to the parental murine L243.

In one exemplary method, two humanized anti-DR MAbs were generated. hL243γ1 was designed to have human IgG 1/κ constant regions, and hL243γ4p was constructed by replacing the heavy chain constant region coding sequence for the human γ1 chain with that of the human γ4 chain. A point mutation, Ser241 Pro, was introduced into the hinge region of the γ4 sequence in order to reduce formation of half-molecules when the antibody is expressed and produced in mammalian cell cultures (Schuurman et al. Mol Immunol. 38:1 (2001)). The ability of the two humanized L243 antibodies, γ1 and γ4P, to bind to Raji cells is shown in FIG. 7, 8 and 17. In FIG. 7, hL243γ1 binding to Raji cells is specifically blocked by pre-incubation of the cells with the parental murine L243 (mL243), indicating that the antigen-binding specificity of mL243 is preserved in the humanized version.

In one example, the reactivity of hL243γ4P relative to the parent mL243 was assessed and a competition cell-binding assay was carried out. A constant amount of $^{125}$I-labeled mL243 or hL243γ4P was incubated with human lymphoma cells (Raji, Daudi or Ramos) in the presence of varying concentrations of purified hL243γ4P or mL243. As shown in FIG. 8, mL243 and hL243γ4P MAbs competed with each other for the binding to the cell surface antigen, indicating recognition of a common antigenic determinant. hL243γ4P had an apparent approximately 2-fold stronger binding avidity than mL243 ($EC_{50}$ of ~7 vs. ~16.5 nM). The maximum number of hL243γ4P and mL243 binding sites per cell and the apparent dissociation constants of the equilibrium binding were determined by Scatchard plot analysis. As shown in FIG. 17, the maximum binding of hL243γ4P and mL243 to Daudi cells was virtually the identical, approximately $6 \times 10^5$ molecules/cell, consistent with binding a common antigen. The apparent dissociation constant values for hL243γ4P and mL243 were calculated to be 2.6 nM and 14 nM, respectively. Similar results were obtained with Raji and Ramos cells (data not shown).

Antigen Expression of Cultured Lymphoma Cell.

In one exemplary method, flow cytometry analysis was performed using indirect immunofluorescent staining to show that hL243γ4P binds to a panel of cultured human B-cell lymphomas. A comparison to other surface antigens is shown. As seen in Table 4, the hL243γ4P MAb binds to all the tested cell lines. A stronger expression was observed on Daudi and Raji, but the level of fluorescence staining is strong on all the cell lines. Binding was compared to that of humanized MAbs against other B-cell antigens (CD74, CD22, CD20), the murine-human chimeric anti-CD20 MAb rituximab, and a humanized anti-CEA MAb (negative control). The staining with hL243γ4P is markedly greater than that of CD22 and CD74 on all seven cell lines. CD20 staining was more variable, as shown by reactivity with the humanized (hA20) and chimeric (rituximab) MAbs. The Burkitt's lines, Daudi, Raji, and Ramos, express intermediate levels of CD20, whereas the follicular and diffuse large B-cell lymphoma lines assessed varied. In comparison to HLA-DR expression measured by hL243γ4P binding, SU-DHL-6 has higher CD20 expression, Namalwa, and WSU-FSCCL lower CD20 expression, and RL approximately equal expression of both antigens.

Effector Cell Assays

In one example, the Fc region of hL43 was replaced with an IgG4 isotype Fc region to abrogate effector cell functions through Fc-receptor and complement-binding. CDC and ADCC assays were performed to assess these functions.

Figure 10:
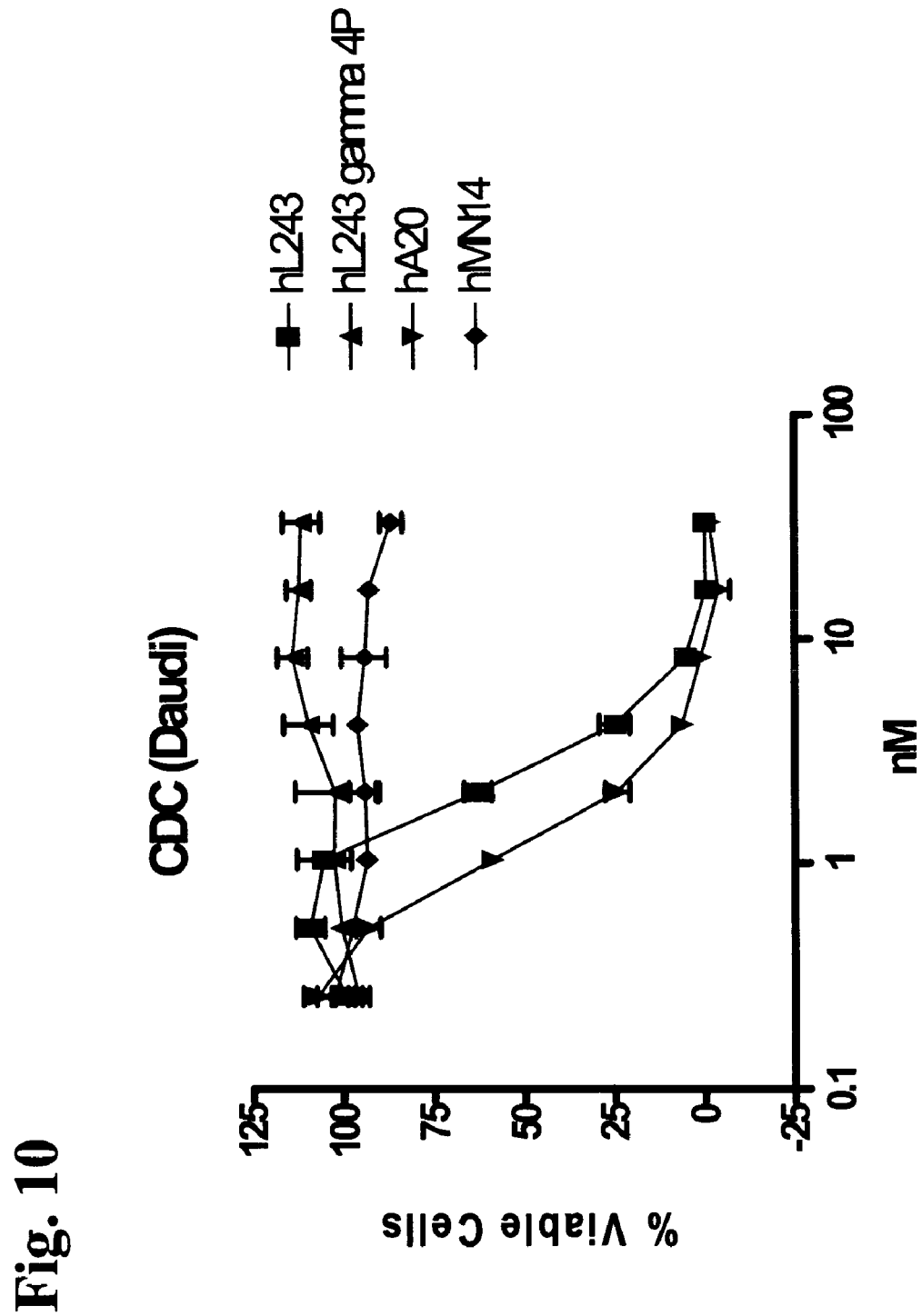
FIG. 10 illustrates an exemplary h243 is effective in killing target cells in the presence of human serum complement: Daudi cells were incubated with hL 243, hL243γ4P, hA20 (a positive control), and hMN-14 (a negative control) in the presence of human serum complement. hL243γ4P was shown not to produce any complement-induced cytotoxicity.
Figure 18:
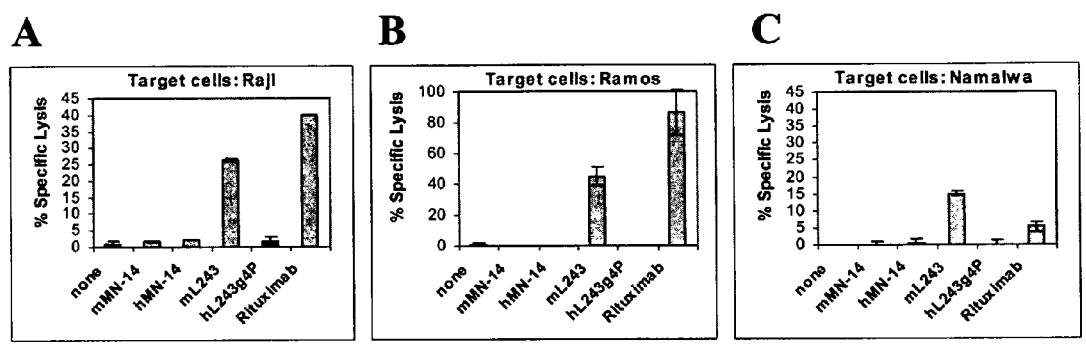
FIGS. 18A, 18B and 18C illustrate CDC assays in Raji (FIG. 18A), Ramos (FIG. 18B) and Namalwa (FIG. 18C) cell lines when exposed to various antibodies disclosed herein.

In another exemplary method, CDC Daudi cells were incubated with serial dilutions of the antibodies hL243γ1, hL243γ4P, hA20 (as another positive control) and hMN14 (anti-CEA, negative control) in the presence of human complement for 2 h. This was followed by the addition of resazurin to assess cell viability. Both untreated and maximum lysis controls were included. Fluorescence readings were obtained 5 h after resazurin addition. The fluorescence level obtained is directly correlated to the number of viable cells. The results here indicate that hL243γ4P does not produce a complement-mediated cytotoxic effect on cells compared to hL243γ1 ($EC_{50}$=2.6 nM) and hA20 ($EC_{50=0.66}$ nM) where CMC was observed (FIG. 10 and 18).

Figure 19:
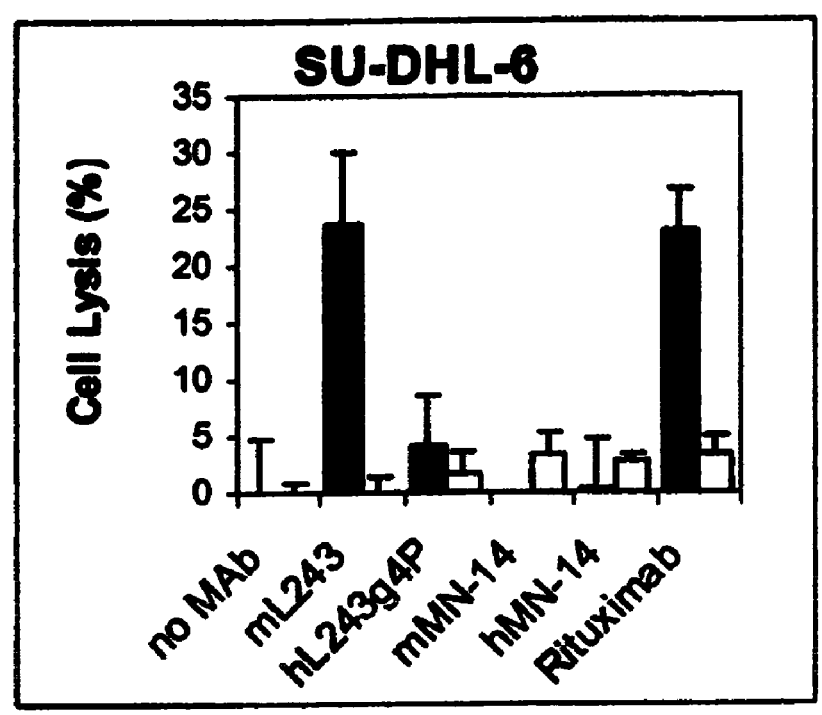
FIG. 19 illustrates ADCC assays and calcein AM release when SU-DHL-6 cells are exposed to various antibodies disclosed herein.

Induction of ADCC was also measured in Raji, Daudi, and SU-DHL-6 by calcein AM release. The activity of hL243γ4P was compared to that of the murine L243 and rituximab, as a positive control. As expected, rituximab and the murine L243 induced significantly more cell lysis than the negative controls (no MAb and murine and humanized MN-14) and hL243γ4P did not (FIG. 19).

In Vitro Anti-proliferative Effects.

In one example, the effect of hL243 on cellular proliferation was assessed using the $^3$H-thymidine uptake assay on Raji, FSCCL, and Namalwa (FIG. 20B and Table 5). The effect of hL243γ4P was compared to that of rituximab and to rituximab combined with hL243γ4P, in the presence or absence of a crosslinking anti Fc antibody. In FSCCL, previously shown to be relatively insensitive to rituximab, hL243γ4P yielded significantly greater inhibition of proliferation than rituximab. In Ramos, hL243 and rituximab activity were similar, and the combination was more effective than either alone. The combination may have a synergistic effect. Cross-linking with an anti-human Fc antibody is required for significant anti-proliferative activity to be seen in Ramos. In Namalwa, as with FSCCL, hL243γ4P yielded significantly greater inhibition of proliferation than rituximab and the combination of rituximab and hL243γ4P yielded significantly more inhibition of proliferation than either MAb alone.

Assessment of Apoptosis Induction

In one exemplary method, the mechanism of hL243 γ4P-induced cell death assays was evaluated by measuring various markers of apoptosis were performed. These included induction of DNA fragmentation, Annexin V/7-AAD staining, measurement of activated caspase-3, loss of mitochondrial membrane potential and activation of the AKT survival pathway.

In another example, DNA fragmentation was evaluated by flow cytometry in SU-DHL-6 and Namalwa. Cells were cultured with the MAbs for 48 h with or without a second MAb for crosslinking, followed by DNA staining with propidium iodide. Cells were analyzed by flow cytometry, and positive florescence below the G1 region represents DNA fragmentation and is a measure of apoptosis. Activity of hL243γ4P was compared to that of humanized MAbs against other B-cell antigens, including anti-CD74 (hLL1), anti CD22 (hLL2, epratuzumab), anti-CD20 (hA20), as well as the murine-human chimeric MAb rituximab. Controls included no first MAb and the negative control humanized anti-CEA MAb, hMN-14. hL243γ4P induced apoptosis in both cell lines, at levels similar to or greater than the other anti-B cell MAbs (FIG. 21A and 21B).

In one particular embodiment, a kit was used (e.g. the Guava Nexin™ kit) to discriminate between apoptotic and nonapoptotic dead cells in Daudi cells. In this example, the kit utilizes Annexin-V-PE to detect phosphatidylserine (PS) on the external membrane of apoptotic cells and a cell impermeant dye 7-AAD as an indicator of membrane structural integrity. 7-AAD is excluded from live, healthy cells and early apoptotic cells, but permeates late stage apoptotic and dead cells. As shown in FIG. 21B the results of this study indicated that hL243γ4P induced apoptosis similar to mL243 following both 4 h and 24 h treatment. In contrast, the anti-CD20 MAb did not induce measurable apoptosis in Daudi. Therefore, hypercrosslinking by a secondary agent, such as anti-human IgG or protein A may be used for induction of apoptosis by anti-CD20 MAbs in many cell lines including Daudi.

Figure 22:
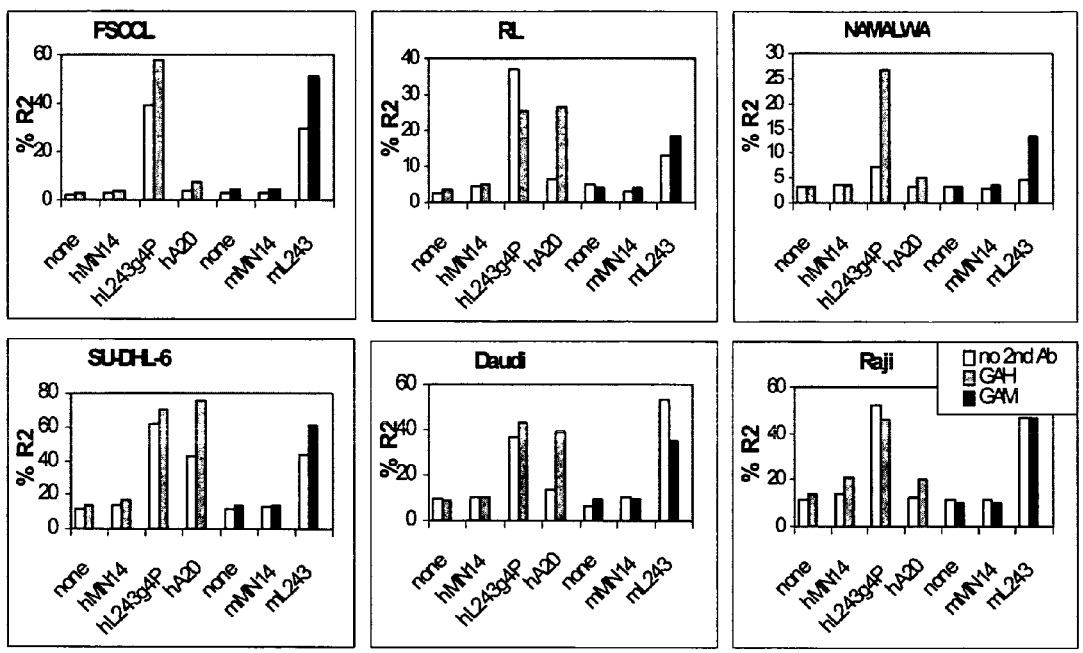
FIG. 22 illustrates mitochondrial membrane potential using a JC-1 assay in several cell lines.

In another example, effects of humanized and murine L243 on mitochondrial potential was studied in different cells, namely, SU-DHL-6, Daudi, Raji, WSU-FSCCL, RL, and Namalwa. Results are represented in FIG. 22 indicating apoptotic changes in the mitochondrial membrane potential were observed with both murine and humanized L243 MAbs. Crosslinking with a second antibody may not be needed, but can increase the effect in 2 of 6 cell lines evaluated, FSCCL and Namalwa. The loss of mitochondrial membrane potential induced by hL243γ4P was greater than that of the anti-CD20 MAb (hA20), without a crosslinking agent. With crosslinking the hA20 levels are increased to those of hL243γ4P in 3 of the 6 cell lines (RL, SU-DHL-6, and Daudi.).

In one example, induction of activated caspase-3 by humanized and murine L243 was assayed by flow cytometry in a panel of lymphoma cell lines. Result summarized in Table 6 represent both the murine and humanized L243 induce activation of caspase-3, at similar levels, in the absence of crosslinking with second antibody. The induction of activated caspase-3 with the L243 MAbs is greater in all cell lines than that of hA20. With a second antibody these levels are increased and the effect of hA20 is similar to that of the hL243γ4P, except in Namalwa and FSCCL, two cell lines which we routinely observe to be relatively insensitive to anti-CD20 MAbs. Cleaved caspase-3 was also assayed in Daudi over a 2 day time course (FIG. 23A). The activity continues to increase for approximately 2 days of L243γ4P incubation. Time points less than 1 h were not done.

In one example, the involvement of AKT in the mechanism of action of L243 was assayed in 6 cell lines by flow cytometry. Cells were incubated with various MAbs for 2 days, then assayed for phospho-AKT. The results listed in Table 7 show that L243 activates AKT in all cell lines. Phospho-AKT levels in anti-CD20, hA20, treated cells, as well as anti-CD74 and anti-CD22 treated cells (not shown), are similar to untreated cells on all cell lines. To determine the time course of P-AKT activation Daudi cells were incubated with MAbs for various times, MAbs were removed (by centrifugation) at time points from 0 min to around 2 days (FIG. 23B). These results represent activation of AKT by L243 can occur faster than can be measured by this assay, because even at the 0 time point P-AKT levels are equal to the 2 day time point.

murine L243 had significantly improved life span compared to mice injected with saline or hMN14 ($P<0.0001$). Treatment with various doses of hL243γ4P resulted in a dose-response relationship, with mice receiving higher doses having better survival times. In the group of animals treated with various doses of mL243 IgG2a, the cure rate was in the range of 80-100%.

TABLE 1

Comparison of binding of humanized and murine MAbs on Namalwa

| Humanized MAbs | GEO MEAN Fluorescence 2nd Ab: FITC GAH | Murine MAbs | GEO MEAN Fluorescence 2nd Ab: FITC GAM |
|---|---|---|---|
| none | 2.52 | none | 2.91 |
| HMN14 | 2.49 | Ag8 | 3.64 |
| hRS7 | 2.47 | MN14 | 3.32 |
| hLL1 | 10.06 | RS7 | 3.39 |
| hLL2 | 6.76 | LL1 | 17.31 |
| hA20 | 6.28 | LL2 | 10.46 |
| Rituximab | 7.33 | 1F5 | 3.83 |
| HL243 | 324.16 | m2B8 | 6.16 |
|  |  | L243 | 594.96 |

[Rituximab is not a humanized, but a chimeric MAb.]

TABLE 2

Phenotyping cell lines (Binding of humanized or chimeric MAbs on B-cell lines by FACS Assay).
Indirect assay using FITC-GAH Fc 2nd Ab staining

| | Geometric Mean Fluorescence | | | | | |
|---|---|---|---|---|---|---|
| | none | hMN14 | hLL1 | hA20 | Rituximab | HL243 |
| Namalwa | 2.5 | 2.36 | 7.81 | 6.4 | 10.11 | 14.12 | 260.8 |
| SU-DHL-6 | 4.6 | 4.94 | 17.29 | 11. | 1199.34 | 1308.89 | 572.2 |
| WSU-FSCCL | 2.6 | 2.66 | 8.66 | 4.1 | 8.91 | 12.45 | 466.7 |
| Raji | 6.8 | 6.96 | 95.10 | 22. | 267.09 | 394.57 | 971.9 |
| Daudi | 3.1 | 3.16 | 48.77 | 51. | 240.96 | 380.45 | 937.4 |
| Ramos | 3.1 | 3.13 | 23.25 | 14. | 203.65 | 374.98 | 277.5 |

In Vivo Therapeutic Efficacy of hL243 in a Xenograft Model of Non-Hodgkin's Lymphoma (Raji)

Figure 24:
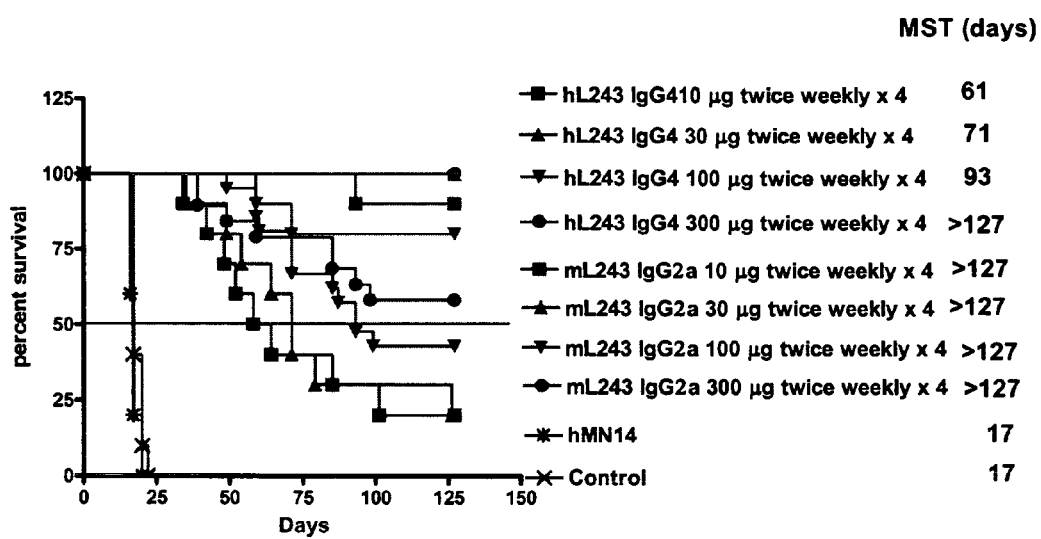
FIG. 24 illustrates therapy of Raji-bearing SCID mice with murine L243 and L243 γ4P.

In one exemplary method, a therapeutic study was performed to compare the in vivo efficacy of hL243γ4P and mL243 (IgG2a isotype) monoclonal antibodies, in a xenograft model of human non-Hodgkin's lymphoma (Raji). The aim of this study was to determine if hL243γ4P can maintain significant antitumor efficacy in a xenograft model. SCID mice were injected with $2.5 \times 10^6$ Raji cells. Therapy with hL243γ4P or mL243 was initiated 1 day-post tumor cell administration. Results are shown in FIG. 24. Both groups of mice injected with saline or with non-specific control antibody, hMN14, had a median survival time (MST) of 17 days. All the groups of mice treated with either humanized or

TABLE 3

Phenotyping dog lymphoma aspirate

| | Murine MAbs | | | Humanized MAbs | |
|---|---|---|---|---|---|
| | % | Mean FL | | % | Mean FL |
| none | 3.85 | 3.37 | none | 4.48 | 3.24 |
| Ag8 | 2.81 | 3.04 | hMN-14 | 4.63 | 3.24 |
| L243 | 77.77 | 10.41 | hL243 | 26.33 | 5.47 |
| m2B8 | 2.61 | 3.11 | hA20 | 3.96 | 3.25 |
| LL1 | 6.69 | 4.01 | hLL1 | 4.71 | 3.33 |
| LL2 | 5.05 | 3.73 | hLL2 | 4.85 | 3.37 |

TABLE 4

Binding of humanized or chimeric MAbs on B-cell lines. An indirect flow cytometry assay was performed using FITC-GAH Fc specific 2nd antibody staining.

| | Geometric Mean Fluorescence | | | | | |
|---|---|---|---|---|---|---|
| | none | anti-CEA (hMN14) | anti-CD74 (hLL1) | anti-CD22 (hLL2) | anti-CD20 (hA20) | anti-CD20 (Rituximab) | anti-HLA-DR (hL243γ4P) |
| Daudi | 3.2 | 3.2 | 48.8 | 51.7 | 241.0 | 380.5 | 937.4 |
| Namalwa | 2.6 | 2.4 | 7.8 | 6.4 | 10.1 | 14.1 | 260.9 |
| Raji | 6.9 | 7.0 | 95.1 | 22.6 | 267.1 | 394.6 | 972.0 |
| Ramos | 3.1 | 3.1 | 23.3 | 14.6 | 203.7 | 375.0 | 277.6 |
| RL | 2.4 | 2.8 | 7.9 | 5.1 | 127.5 | 147.8 | 112.2 |
| SU-DHL-6 | 4.6 | 4.9 | 17.3 | 11.0 | 1199.3 | 1308.9 | 572.3 |
| WSU-FSCCL | 2.7 | 2.7 | 8.7 | 4.2 | 8.9 | 12.5 | 466.8 |

TABLE 5

Summary of antiproliferative activity of MAbs with and without crosslinking (% Inhibition of 3-H-Thymidine uptake)

| | Rituximab + hL243 | Rituximab | hL243γ4P |
|---|---|---|---|
| Antiproliferative activity of MAbs without crosslinking | | | |
| Ramos | 18.2 ± 4.9 | −7.9 ± 3.6 (0.0001)[a] | 10.1 ± 11.9 (0.3619) |
| FSCCL | 75.9 ± 10.2 | 13.4 ± 12.3 (0.0028) | 78.9 ± 1.7 (0.6611) |
| Namalwa | 50.1 ± 1.1 | 13.8 ± 5.6 (0.0061) | 27.8 ± 3.3 (0.0038) |
| Antiproliferative activity of MAbs in the presence of anti-human 2$^{nd}$ Ab | | | |
| Ramos | 69.0 ± 7.0 | 50.5 ± 9.4 (0.0519) | 56.8 ± 0.8 (0.0073) |
| FSCCL | 94.5 ± 0.9 | 28.1 ± 9.6 (0.0067) | 94.5 ± 0.8 (0.9984) |
| Namalwa | 58.1 ± 2.1 | 14.7 ± 7.0 (0.0050) | 51.5 ± 3.0 (0.0416) |

[a]Numbers in parentheses represent P values of the single MAbs in comparison to the combination of rituximab + hL243γ4P.

TABLE 6

Cleaved Caspase-3 assay

Cleaved caspase-3 (% above no MAb control)

| | Humanized MAbs | | | murine MAbs | |
|---|---|---|---|---|---|
| | hL243g4P | hA20 | hMN-14 | mL243 | mMN-14 |
| No crosslinking | | | | | |
| Ramos | 26.9 | 3.2 | 0.8 | 15.8 | 3.9 |
| Namalwa | 18.4 | −0.1 | 0.2 | 9.4 | 0.5 |
| FSCCL | 46.4 | 0.7 | 0.3 | 26.2 | −0.7 |
| Daudi | 48.1 | 7.9 | 0.9 | 45.8 | 1.0 |
| RL | 22.5 | 1.5 | −0.1 | 18.2 | −0.3 |
| SU-DHL-6 | 52.2 | 30.9 | 2.3 | 46.5 | 0.2 |
| Raji | 22.5 | 1.5 | −0.1 | 18.2 | −0.3 |
| with 2nd Ab | | | | | |
| Ramos | 71.7 | 67.8 | 7.3 | 40.3 | 3.0 |
| Namalwa | 72.2 | 20.4 | 7.9 | 25.2 | −0.3 |
| FSCCL | 86.7 | 20.0 | 8.4 | 55.0 | 1.5 |
| Daudi | 68.9 | 72.0 | 2.9 | 51.2 | 0.0 |
| RL | 37.3 | 24.2 | 4.0 | 4.0 | 0.7 |
| SU-DHL-6 | 72.1 | 75.8 | 5.5 | 51.4 | −0.9 |
| Raji | 59.8 | 37.4 | 2.8 | 20.4 | −0.3 |

TABLE 7

P-AKT assay

% above no MAb control

| | humanized MAbs | | | murine MAbs | |
|---|---|---|---|---|---|
| | hL243g4P | hA20 | hMN-14 | mL243 | mMN-14 |
| Namalwa | 8.4 | −2.8 | 1.3 | 3.5 | −4.4 |
| FSCCL | 25.1 | −1.4 | 3.9 | 16.3 | −1.7 |
| Daudi | 34.9 | 1.0 | −1.4 | 24.5 | −2.1 |
| RL | 5.9 | 1.8 | 0.0 | 1.3 | 1.3 |
| SU-DHL-6 | 29.8 | 0.2 | 1.2 | 26.1 | −0.5 |
| Raji | 5.1 | −0.9 | −1.6 | 17.2 | −4.2 |

All of the COMPOSITIONS and/or METHODS and/or APPARATUS disclosed and claimed herein can be made and executed without undue experimentation in light of the present disclosure. While the compositions and methods of this invention have been described in terms of preferred embodiments, it will be apparent to those of skill in the art that variation may be applied to the COMPOSITIONS and/or METHODS and/or APPARATUS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A humanized L243 antibody or antigen-binding fragment thereof, comprising heavy chain variable domain complementarity determining region (CDR) sequences CDR1 (NYGMN, residues 31 to 35 of SEQ ID NO: 4), CDR2 (WINTYTREPTYADDFKG, residues 50 to 66 of SEQ ID NO:4), and CDR3 (DITAVVPTGFDY, residues 99 to 110 of SEQ ID NO:4) and heavy chain framework residues F27, K38, K46, A68, and F91 and light chain variable domain CDR sequences CDR1 (RASENIYSNLA, residues 24 to 34 of SEQ ID NO:2), CDR2 (AASNLAD, residues 50 to 56 of SEQ ID NO:2), and CDR3 (QHFWTTPWA, residues 89 to 98 of SEQ ID NO:2) and light chain framework residues R37, K39, V48 and F49, wherein the remainder of the humanized L243 antibody framework region and constant region sequences are from one or more human antibodies, wherein the humanized L243 antibody has the ability to bind to HLA-DR on HLA-DR+ cells, and wherein said humanized L243 antibody induces apoptosis of said HLA-DR+ cells without inducing complement-mediated cytotoxicity (CDC) or antibody-dependent cell mediated cytotoxicity (ADCC).

2. The humanized L243 antibody or antigen-binding fragment thereof of claim 1, wherein the humanized L243 antibody or fragment comprises human IgG4 constant region sequences.

3. The humanized L243 antibody or antigen-binding fragment thereof of claim 2, further comprising a Ser241 Pro point mutation in the hinge region of the antibody or fragment thereof.

4. The humanized L243 antibody or antigen-binding fragment thereof of claim 1, wherein humanized L243 antibody comprises the hL243VK amino acid sequence SEQ ID NO:6 and the hL243VH amino acid sequence SEQ ID NO:8.

5. The humanized L243 antibody or antigen-binding fragment thereof of claim 1, wherein the humanized L243 antibody has a lower dissociation constant for HLA-DR+ cells than the murine L243 antibody.

6. The humanized L243 antibody or antigen-binding fragment thereof of claim 1, wherein the humanized L243 antibody or fragment thereof is a naked antibody or fragment thereof.

7. The humanized L243 antibody or antigen-binding fragment thereof of claim 1, wherein the humanized L243 antibody or fragment thereof is conjugated to at least one therapeutic or diagnostic agent.

8. The humanized L243 antibody or antigen-binding fragment thereof of claim 7, wherein the therapeutic agent is selected from the group consisting of antibodies, antibody fragments, drugs, chemotherapeutic agents, toxins, enzymes, nucleases, hormones, hormone antagonists, immunomodulators, cytokines, oligonucleotides, interference RNA, chelators, boron compounds, photoactive agents, dyes and radioisotopes.

9. The humanized L243 antibody or antigen-binding fragment thereof of claim 8, wherein the chemotherapeutic agent is a taxane, a nitrogen mustard, an ethylenimine, an alkyl sulfonate, a nitrosourea, a triazene, a folic acid analog, a pyrimidine analog, a purine analog, an antisense oligonucleotide, an interference RNA, an antibiotic, a platinum coordination complex, a COX-2 inhibitor, an apoptotic agent, a substituted urea, a methyl hydrazine, a steroid, a progestin, an estrogen, an antiestrogen, an androgen, actinomycin, azaribine, anastrozole, azacytidine, bleomycin, bryostatin-1, busulfan, carmustine, Celebrex, chlorambucil, cisplatin, irinotecan (CPT-11), carboplatin, cladribine, cyclophosphamide, cytarabine, dacarbazine, docetaxel, dacarbazine, dactinomycin, daunorubicin, dexamethasone, diethyistilbestrol, doxorubicin, ethinyl estradiol, estramustine, etoposide, floxuridine, fludarabine, flutamide, 5-fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, methotrexate, mitoxantrone, mitomycin, mitotane, oxaliplatin, phenyl butyrate, prednisone, procarbazine, paclitaxel, pentostatin, semustine, streptozocin, SN-38, tamoxifen, taxanes, taxol, testosterone propionate, thalidomide, thioguanine, thiotepa, teniposide, topotecan, uracil mustard, vinblastine, vinorelbine or vincristine.

10. The humanized L243 antibody or antigen-binding fragment thereof of claim 8, wherein the toxin is ricin, abrin, ribonuclease, DNase I, Staphylococcal enterotoxin-A, pokeweed antiviral protein, gelonin, diphtheria toxin, Pseudomonas exotoxin, or Pseudomonas endotoxin.

11. The humanized L243 antibody or antigen-binding fragment thereof of claim 8, wherein the immunomodulator is a cytokine, a stem cell growth factor, a lymphotoxin, a tumor necrosis factor (TNF), TNF-α, a hematopoietic factor, an interleukin, IL-1, IL-2, IL-3, IL-6, IL-10, IL-12, IL-18, IL-21, a colony stimulating factor, G-CSF, GM-CSF, interferon-α, -β or -γ, the stem cell growth factor designated "S1 factor", erythropoietin or thrombopoietin.

12. The humanized L243 antibody or antigen-binding fragment thereof of claim 11, wherein the cytokine is interferon-α, interferon-β, interferon-γ or GM-CSF.

13. The humanized L243 antibody or antigen-binding fragment thereof of claim 8, wherein the radioisotope is In-111, Lu-177, Bi-212, Bi-213, At-211, Cu-62, Cu-64, Cu-67, Y-90, I-125, I-131, P-32, P-33, Sc-47, Ag-111, Ga-67, Pr-142, Sm-153, Th-161, Dy-166, Ho-166, Re-186, Re-188, Re-189, Pb-212, Ra-223, Ac-225, Fe-59, Se-75, As-77, Sr-89, Mo-99, Rh-105, Pd-109, Pr-143, Pm-149, Er-169, Ir-194, Au-198, Au-199, Ac-225 or Pb-211.

14. A bispecific antibody or antigen-binding fragment thereof comprising at least one first antibody or fragment thereof according to claim 1 and at least one second antibody or fragment thereof.

15. The bispecific antibody or fragment thereof of claim 14, wherein the second antibody or second antibody fragment binds to a tumor-associated antigen.

16. The bispecific antibody or fragment thereof of claim 15, wherein the tumor-associated antigen is selected from the group consisting of A3, antigen specific for A33 antibody, BrE3-antigen, CD1, CD1a, CD3, CD5, CD15, CD19, CD20, CD21, CD22, CD23, CD25, CD30, CD45, CD74, CD79a, CD80, HLA-DR, NCA95, NCA90, HCG, CEA (CEACAM-5), CEACAM-6, CSAp, EGFR, EGP-1, EGP-2, Ep-CAM, Ba 733, HER2/neu, hypoxia inducible factor (HIF), KC4-antigen, KS-1 antigen, KS 1-4, Le-Y, macrophage inhibition factor (MIF), MAGE, MUC1, MUC2, MUC3, MUC4, MUC16, PAM-4-antigen, PSA, PSMA, RS5, S100, TAG-72, p53, tenascin, IL-6, IL-8, insulin growth factor-1 (IGF-1), Tn antigen, Thomson-Friedenreich antigens, tumor necrosis antigens, VEGF, 17-1 A-antigen, an angiogenesis marker, ED-B fibronectin, an oncogene marker, an oncogene product, Ia, HM1.24, VEGF, ILGF, placental growth factor and carbonic anhydrase IX.

17. The bispecific antibody or fragment thereof of claim 14, wherein the second antibody or second antibody fragment binds to a targetable conjugate that comprises at least one hapten moiety and at least one therapeutic agent.

18. The humanized L243 antibody or antigen-binding fragment thereof of claim 1, wherein the antibody or fragment induces apoptosis in cancer cell lines that are resistant to anti-CD20 antibodies.

19. The humanized L243 antibody or antigen-binding fragment thereof of claim 18, wherein the antibody or fragment induces apoptosis in the Namalwa human lymphoma cell line.

20. A pharmaceutical composition comprising a humanized L243 antibody or antigen-binding fragment thereof according to claim 1.

21. The composition of claim 20, wherein the humanized L243 antibody or fragment thereof is conjugated to one or more peptides, lipids, polymeric carriers, micelles, nanoparticles, or a combination thereof.

22. The composition of claim 20, further comprising at least one therapeutic agent.

23. The composition of claim 22, wherein the therapeutic agent is a drug, a prodrug, a toxin, an enzyme, a radioisotope, an immunomodulator, a cytokine, a hormone, a second antibody or antigen binding fragment thereof, an oligonucleotide, an interference RNA, a photodynamic agent, or a combination thereof.

24. The composition of claim 20, wherein the humanized L243 antibody or antigen-binding fragment thereof is conjugated to a chelator selected from the group consisting of NOTA, DOTA, DTPA, TETA, Tscg-Cys, Tsca-Cys, or a combination thereof.

25. A kit comprising a composition according to claim 22.

* * * * *

UNITED STATES PATENT AND TRADEMARK OFFICE
CERTIFICATE OF CORRECTION

PATENT NO.      : 7,612,180 B2                                          Page 1 of 1
APPLICATION NO. : 11/368296
DATED           : November 3, 2009
INVENTOR(S)     : Goldenberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 498 days.

Signed and Sealed this

Nineteenth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,612,180 B2 | Page 1 of 1 |
| APPLICATION NO. | : 11/368296 | |
| DATED | : November 3, 2009 | |
| INVENTOR(S) | : David M. Goldenberg et al. | |

It is certified that error appears in the above-identified patent and that said Letters Patent is hereby corrected as shown below:

IN THE CLAIMS:
In Column 76, line 60, claim 1,
change "OHFWTTPWA, residues 89 to 98" to --QHFWTTPWA, residues 89 to 97--

Signed and Sealed this
Nineteenth Day of April, 2011

David J. Kappos
*Director of the United States Patent and Trademark Office*